(12) United States Patent
Takahaski et al.

(10) Patent No.: US 6,291,429 B1
(45) Date of Patent: Sep. 18, 2001

(54) CLOCK GENE AND GENE PRODUCT

(75) Inventors: Joseph S. Takahaski, Wilmette; Fred Turek, Chicago; Lawrence H. Pinto, Evanston, all of IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 09/496,672

(22) Filed: Feb. 3, 2000

Related U.S. Application Data

(62) Division of application No. 08/885,291, filed on Jun. 30, 1997, now Pat. No. 6,057,125.

(51) Int. Cl.$^7$ .................................................. C07K 14/00
(52) U.S. Cl. ........................................ 514/12; 530/350
(58) Field of Search ................................. 514/2; 530/350

(56) References Cited

PUBLICATIONS

Albertsson–Wikland and Rosberg, 1988, J. Clin. Endocrinol. Metab 67:493–500.
Aldrich, 1994, In: Principles and Practice of Sleep Medicine, Kryger et al., eds., Philadelphia, W.B. Saunders Co., pp. 783–789.
Altschul et al., 1990, J. Mol. Biol. 215:403–410.
Aronson et al., 1994, Science 263:1578–1584.
Baylies et al., 1987, Nature 326:390–392.
Benca, 1994. In: Principles and Practice of Sleep Medicine, Kryger et al., eds., Philadelphia, W.B. Saunders Co., pp. 899–913.
Benca and Casper, 1994. In: Principles and Practice of Sleep Medicine, Kryger et al., eds., Philadelphia, W.B. Saunders Co., pp. 927–933.
Bliwise, 1994. In: Principle and Practice of Sleep Medicine, Kryger et al., eds., Philadelphia, W.B. Saunders Co., pp. 790–800.
Borbèly, 1994. In: Principles and Practice of Sleep Medicine, Kryger et al., eds., Philadelphia, W.B. Saunders Co., pp. 309–320.
Burbach et al., 1992, Proc. Natl. Acad. Sci USA 89:8185–8189.
Calvo et al., 1995, J. Pineal Res. 18:119–126.
Card and Moore, 1991. In: Suprachiasmatic Nucleus: The Mind's Clock, Klein et al., eds., New York, Oxford University Press, pp. 51–76.
Cohen and Muller, 1992, Cardiovascular Res. 26:831–838.
Colantonio et al., 1989, Life Sciences 45:631–635.
Constantinescu, 1995, Med Hypotheses 45:455–458.
Crosthwaite et al., 1995, Cell 81:1003–1012.
de Graaf et al., 1993, Intl. J. Obesity 17:521–526.
Decker et al., 1995, Cell Tissue Res. 282:473–480.
Douglas, 1994. In: Principles and Practice of Sleep Medicine, Kryger et al., eds., Philadelphia, W.B. Saunders Co., pp. 204–211.
Dunlap, 1993, Annu. Rev. Physiol. 55:683–728.
Dunlap, 1996, Annu. Rev. Gen. 30:579–601.
Edery et al., 1994, proc. Natl. Acad. Sci. 91:2260–2264.
Favello et al., 1995, In: Methods in Cell Biology, Epstein and Shakes eds., pp. 551–569, San Diego: Academic Press.
Feldman and Hoyle, 1973, *Neurospora crassa*. Genetics 75:605–613.
Feldman, 1982, Ann. Rev. Plant Physiol. 33:583–608.
Fields and Song, 1989, Nature 340:245–246.
Garcia–Pagaan et al., 1994, Hepatology 19:595–601.
Geissler et al., 1988, Cell 55:185–192.
Gekakis et al., 1995, Science 270:811–815.
George, 1994. In: Principles and Practice of Sleep Medicine, Kryger et al., eds., Philadelphia, W.B. Saunders Co., pp. 835–846.
Gillis and Flemons, 1994. In: Principles and Practice of Sleep Medicine, Kryger et al., eds., Philadelphia, W.B. Saunders Co., pp. 847–860.
Graeber, 1994. In: Principles and Practice of Sleep Medicine, Kryger et al., eds., Philadelphia, W.B. Saunders Co., pp. 463–470.
Hall, 1990, Annu. Rev. Genet. 24:659–697.
Hall and Kyriacou, 1990, Drosophila. Adv. Insect Physiol. 22:221–297.
Hallonquist et al., 1986, Can. J. Psychiatry 31:259–271.
Hardin et al., 1990, Nature, 343:536–540.
Hardin et al., 1992, Proc. Natl. Acad. Sci USA 89:11711–11715.
Hartmann, 1994. In: Principles and Practice of Sleep Medicine, Kryger et al., eds., Philadelphia, W.B. Saunders Co., pp. 598–601.
Hineno et al., 1992, Brain Res. 580:92–99.
Hoffman et al., 1991, Science 252:954–958.
Hokken–Koelegal et al., 1990, J. Clin. Endocrinol. Metabl. 71:688–695.
Huang et al., 1993, Nature 364:259–262.
Hunter–Ensor et al., 1996, Cell 84:677–685.
Hyde et al., 1995, Psychiatry Research 56:52–57.
Jacobshagen and Johnson, 1994, European J. Cell Biol. 64:142–152.
Kohler et al., 1975, Nature 256:495–497.
Konopka and Benzer, 1971, Proc. Natl. Acad. Sci. USA 68:2112–2116.
Krawczak et al., 1992, Human Genetics 90:41–54.
Krumlauf, 1993, Trends Genet. 9:106–112.

(List continued on next page.)

*Primary Examiner*—Karen Cochrane Carlson
(74) *Attorney, Agent, or Firm*—Morgan, Lewis & Bockius, L.L.P.

(57) ABSTRACT

The present invention provides isolated and purified polypeptide components of the mammalian circadian clock, polynucleotides that encode those polypeptides, expression vectors containing those polynucleotides, host cells transformed with those expression vectors, a process of making the polypeptide components using those polynucleotides and vectors, and processes using those polypeptides and polynucleotides.

6 Claims, 57 Drawing Sheets

OTHER PUBLICATIONS

Kryger et al., 1994. In: Principles and Practice of Sleep Medicine, Kryger et al., eds., Philadelphia, W.B. Saunders Co., pp. 301–308.
Kusumi et al., 1993, Mammalian Genome 4:391–392.
Larsen et al., 1993, Digestive Diseases and Sciences 38:1435–1440.
Larsen et al., 1991, J. Surgical Res. 51:275–280.
Lausson et al., 1989, J. Endocrinol. 122:527–534.
Lee et al., 1996, Science 271:1740–1744.
Lisitsyn et al., 1993, Science 259:946–951.
Liu et al., 1992, Drosophila. J. Neurosci. 12:2735–2744.
Loros et al., 1989, Science 243:385–388.
Lugaresi and Montagna, 1994, In: Principles and Practice of Sleep Medicine, Kryger et al., eds., Phildelphia, W.B. Saunders Co., pp. 547–548.
Lyon et al., 1984, Genetical Research 44:161–168.
Mann et al., 1986, British Med. J. 293:1265–1267.
Marchuk and Collins, 1994. In: Yac Libraries: A User's Guide, Nelson and Brownstein eds., pp. 113–126. New York, W.H. Freeman and Co.
Matsui et al., 1993, Neurosci. Lett. 163:189–192.
McClung et al., 1989, Nature 339:558–562.
Meijer, 1991, In: Suprachiasmatic Nucleus: The Mind's Clock, Klein et al., eds., New York, Oxford University Press, pp. 107–119.
Millar and Kay, 1991, The Plant Cell 3:541:550.
Monk, 1994, In: Principles and Practice of Sleep Medicine, Kryger et al., eds., Philadelphia, W.B. Saunders Co., pp. 471–476.
Myers et al., 1996, Science 1972:1736–1740.
Myers et al., 1995, Science 270:805–808.
Nambu et al., 1991, Cell 67:1157–1167.
Orem, 1994, In: Principles and Practice of Sleep Medicine, Kryger et al., eds., Philadelphia, W.B. Saunders Co., pp. 177–193.
Orr, 1994, In: Principles and Practice of Sleep Medicine, Kryger et al., eds., Philadelphia, W.B. Saunders Co., pp. 252–259.
Park and Horvitz, 1986, Genetics 113:821–852.
Pittendrigh and Daan, 1976, J. Comp. Physiol. 106:223–252.
Ralph and Menaker, 1988, Science 241:1225–1227.
Ralph and Lehman, 1991, Trends Neurosci. 14:362–366.
Reppert et al., 1994, *Antheraea pernyi*. Neuron. 13:1167–1176.
Roehrs and Roth, 1994, In: Principles and Practice of Sleep Medicine, Kryger et al., eds., Philadelphia, W. B. Saunders Co., pp. 477–481.
Rosbash and Hall, 1989, Neuron. 3:387–398.
Roth et al., 1994, In: Principles and Practice of Sleep Medicine, Kryger et al., eds., Philadelphia, W.B. Saunders Co., pp. 40–49.
Rusak and Zucker, 1975, Ann. Rev. Psychol. 26:137–171.
Sack et al., 1992, J. Clin. Endocrinol. and Metab. 75:127–134.
Schwartz and Zimmerman, 1990, J. Neurosci. 10:3685–3694.
Sehgal et al., 1994, Science 263:1603–1606.
Shin et al., 1985, Nature 317:445–448.
Siwicki et al., 1988, Neuron. 1:141–150.
Siwicki et al., 1992, J. Neurogenetics 8:33–42.
Smith and Konopka, 1981, Mol. Gen. Genet., 183:243–251.
Smith et al., 1994, Lancet 344:1137–1139.
Spallone et al., 1993, Diabetes 42:1745–1752.
Takahashi, 1995, Annu. Rev. Neurosci. 18:531–553.
Takahashi, et al., 1994, Science 264:1724–1733.
Terman, 1994, In: Principles and Practice of Sleep Medicine, Kryger et al., eds., Philadelphia, W.B. Saunders Co., pp. 1012–1029.
Tornatzky and Miczek, 1993, Physiol. Behav. 53:983–993.
Turek, 1994, In: Recent Progress in Hormone Research, Bardin, eds., New York, Academic Press, pp. 43–90.
Turek and Van Cauter, 1994, In: Physiology of Reproduction, New York, Knobil and Neill, eds., Raven Press, pp. 487–540.
Turek and Van Reeth, 1996, In: Handbook of Physiology: Chapter 4—Environmental Physiology, Fregly and Blatteis, eds., Oxford University Press, pp. 1329–1360.
Van Reeth et al., 1994, Am. J. Physiol. 266:E964–E974.
Van Cauter and Turek, 1995, In: Endocrinology, DeGroot, eds., Philadephia, W.B. Saunders, pp. 2487–2548.
Van Cauter and Turek, 1986, Perspecct. Biol. Med. 29:510–519.
Vignau et al., 1993, In: Light and Biological Rhythms in Man, Wetterberg ed., pp. 261–271. Oxford: Pergamon Press.
Vitaterna et al., 1994, Science 264:719–725.
Vogelbaum and Menaker, 1992, J. Neurosci. 12:3619–3627.
Vosshall et al., 1994, Science 263:1606–1609.
Wehr et al., 1979, Science 206:710–713.
Wehr and Rosenthal, 1989, Am. J. Psychiatry 146:829–839.
Wehr et al., 1983, Federation Proc. 42:2809–2814.
Weltzin et al., 1991, Biol. Psychiatry 30:1093–1110.
Wetterberg, 1994, J. Internal Medicine 235:5–19.
Young, 1980, Neurochemistry 1:123–142.
Yu et al., 1987, Proc. Natl. Acad. Sci. USA 84:784–788.
Zeng et al., 1996, Nature 380:129–135.
Zerr et al., 1990, J. Neurosci. 10:2749–2762.

Fig. 8A

```
GGGGAGGAGC GCGGCGGTAG CGGTGAATTT TGAGGGGTGG GTCGGGGGCG CGCACTCGCC    60
GCCCCTGGTG CTGCCGGCTC CCGGAGCCTC GGCGTGTCCC GGCGTGTCGC GCTCGGCTGT   120
CGCGAGCCGC CGCGGGCAGA GTCCCGGGCG GGGAGGGAG GAAGCCGGAG CCTCAGGCAC    180
GTGAAAGAAA AGCACAAGAA GAAACTTTTA CAGGCGTTGT TGATTGGACT AGGGCAACGA   240
TTCCAAAAT CACCAGCAAG AGTTCTGATG GTCAGTCACA CAGAAGACGG CCTTGCGTCT    300
GTGGGTGTTG GAGACTCCAT TCTAAAGATA TAAAAGTGA AAGAGGAGAA GTACAAATGT    360
CTACCACAAG ACGAAAACAT AATGTGTT ATG GTG TTT ACC GTA AGC TGT AGT      412
                                Met Val Phe Thr Val Ser Cys Ser
                                  1               5

AAA ATG AGC TCA ATT GTT GAC AGA GAT GAC AGT AGT ATT TTT GAT GGA    460
Lys Met Ser Ser Ile Val Asp Arg Asp Asp Ser Ser Ile Phe Asp Gly
         10                  15                  20

TTG GTG GAA GAA GAT GAC AAG GAC AAA GCA AAA AGA GTA TCT AGA AAC    508
Leu Val Glu Glu Asp Asp Lys Asp Lys Ala Lys Arg Val Ser Arg Asn
 25                  30                  35                  40

AAA TCA GAA AAG AAA CGT AGA GAT CAG TTC AAT GTC CTC ATT AAG GAG    556
Lys Ser Glu Lys Lys Arg Arg Asp Gln Phe Asn Val Leu Ile Lys Glu
         45                  50                  55

CTG GGG TCT ATG CTT CCT GGT AAC GCG AGA AAG ATG GAC AAG TCT ACT    604
Leu Gly Ser Met Leu Pro Gly Asn Ala Arg Lys Met Asp Lys Ser Thr
 60                  65                  70
```

Fig. 8B

```
GTT CTA CAG AAG AGC ATT GAT TTT TTG CGC AAA CAT AAA GAG ACC ACT    652
Val Leu Gln Lys Ser Ile Asp Phe Leu Arg Lys His Lys Glu Thr Thr
              75                  80                  85

GCA CAG TCA GAT GCT AGT GAG ATT CGA CAG GAC TGG AAA CCC ACA TTC    700
Ala Gln Ser Asp Ala Ser Glu Ile Arg Gln Asp Trp Lys Pro Thr Phe
         90                  95                 100

CTT AGT AAT GAA GAG TTT ACA CAG TTA ATG TTA GAG GCT CTT GAT GGT    748
Leu Ser Asn Glu Glu Phe Thr Gln Leu Met Leu Glu Ala Leu Asp Gly
105                 110                 115                 120

TTT TTT TTA GCG ATC ATG ACA GAT GGA AGT ATA TAT GTA TCT GAG        796
Phe Phe Leu Ala Ile Met Thr Asp Gly Ser Ile Ile Tyr Val Ser Glu
                125                 130                 135

AGT GTA ACT TCG TTA CTT GAA CAT TTA CCA TCT GAT CTT GTG GAT CAA    844
Ser Val Thr Ser Leu Leu Glu His Leu Pro Ser Asp Leu Val Asp Gln
        140                 145                 150

AGT ATA TTT AAT TTT ATC CCA GAG GGA GAA CAT TCA GAG GTT TAT AAG    892
Ser Ile Phe Asn Phe Ile Pro Glu Gly Glu His Ser Glu Val Tyr Lys
    155                 160                 165
```

Fig. 8C

```
ATA CTC TCT ACT CAT CTG CTG GAA AGT GAC TCA TTA ACC CCT GAG TAC   940
Ile Leu Ser Thr His Leu Leu Glu Ser Asp Ser Leu Thr Pro Glu Tyr
        170                 175                 180

TTA AAA TCA AAA AAT CAG TTA GAA TTC TGT TGT CAC ATG CTT CGA GGA   988
Leu Lys Ser Lys Asn Gln Leu Glu Phe Cys Cys His Met Leu Arg Gly
    185                 190                 195                 200

ACA ATA GAC CCA AAG GAG CCA TCC ACC TAT GAA TAT GTG AGA TTT ATA  1036
Thr Ile Asp Pro Lys Glu Pro Ser Thr Tyr Glu Tyr Val Arg Phe Ile
            205                 210                 215

GGA AAT TTT AAA TCT TTA ACC AGT GTA TCA ACT TCA ACA CAC AAT GGT  1084
Gly Asn Phe Lys Ser Leu Thr Ser Val Ser Thr Ser Thr His Asn Gly
        220                 225                 230

TTT GAA GGA ACT ATA CAA CGC ACA CAT AGG CCT TCT TAT GAA GAT AGA  1132
Phe Glu Gly Thr Ile Gln Arg Thr His Arg Pro Ser Tyr Glu Asp Arg
    235                 240                 245

GTT TGT TTT GTA GCT ACT GTC AGA TTA GCT ACA CCT CAG TTC ATC AAG  1180
Val Cys Phe Val Ala Thr Val Arg Leu Ala Thr Pro Gln Phe Ile Lys
            250                 255                 260
```

Fig. 8D

```
GAA ATG TGT ACT GTT GAA GAA CCA AAT GAA GAG TTT ACA TCT AGA CAC      1228
Glu Met Cys Thr Val Glu Glu Pro Asn Glu Glu Phe Thr Ser Arg His
265                 270                 275                 280

AGT TTA GAA TGG AAG TTT CTA TTT TTA GAT CAC AGG GCA CCA CCA ATA      1276
Ser Leu Glu Trp Lys Phe Leu Phe Leu Asp His Arg Ala Pro Pro Ile
        285                 290                 295

ATA GGC TAT TTG CCA TTT GAA GTC TTG GGA ACA TCA GGC TAT GAT TAC      1324
Ile Gly Tyr Leu Pro Phe Glu Val Leu Gly Thr Ser Gly Tyr Asp Tyr
    300                 305                 310

TAT CAT GTG GAT GAC CTA GAA AAT CTG GCA AAA TGT CAC GAG CAC TTA      1372
Tyr His Val Asp Asp Leu Glu Asn Leu Ala Lys Cys His Glu His Leu
315                 320                 325

ATG CAA TAT GGA AAA GGC AAA GGG AAG TCG TGT TAC TAT AGA TTC CTG ACC AAA  1420
Met Gln Tyr Gly Lys Gly Lys Lys Ser Cys Tyr Tyr Arg Phe Leu Thr Lys
330                 335                 340

GGC CAG CAG TGG ATA TGG CTT CAG ACT CAT TAT ATT ACT TAC CAT          1468
Gly Gln Gln Trp Ile Trp Leu Gln Thr His Tyr Tyr Ile Thr Tyr His
345                 350                 355                 360
```

Fig. 8E

```
CAG TGG AAT TCA AGG CCA GAG TTC ATT GTT TGT ACT CAC ACT GTA GTA   1516
Gln Trp Asn Ser Arg Pro Glu Phe Ile Val Cys Thr His Thr Val Val
        365                     370                     375

AGT TAT GCA GAA GTT AGG GCT GAA CGG CGA GAA CTT GGC ATT GAA       1564
Ser Tyr Ala Glu Val Arg Ala Glu Arg Arg Glu Leu Gly Ile Glu
        380                     385                     390

GAG TCT CTT CCT GAG ACA GCT GCT GAC AAA AGC CAA GAT TCT GGG TCT   1612
Glu Ser Leu Pro Glu Thr Ala Ala Asp Lys Ser Gln Asp Ser Gly Ser
        395                     400                     405

GAC AAT CGT ATC AAC ACA GTG AGT CTC AAG GAA GCA CTG GAA AGG TTT   1660
Asp Asn Arg Ile Asn Thr Val Ser Leu Lys Glu Ala Leu Glu Arg Phe
        410                     415                     420

GAT CAC AGC CCA ACT CCT TCT GCC TCC TCT AGA AGC TCA CGA AAG TCA   1708
Asp His Ser Pro Thr Pro Ser Ala Ser Ser Arg Ser Ser Arg Lys Ser
        425                     430                     435                     440

TCT CAC ACC GCA GTC TCA GAC CCT TCC TCC ACA AAG ATC CCT           1756
Ser His Thr Ala Val Ser Asp Pro Ser Ser Thr Lys Ile Pro
        445                     450                     455
```

Fig. 8F

```
ACT GAT ACT AGC ACT CCT CCC AGA CAG CAT TTG CCA GCT CAT GAA AAG    1804
Thr Asp Thr Ser Thr Pro Pro Arg Gln His Leu Pro Ala His Glu Lys
        460                 465                 470

ATG ACA CAG CGG AGG TCG TCC TTC AGC AGT CAG TCC ATA AAC TCC CAG    1852
Met Thr Gln Arg Arg Ser Ser Phe Ser Ser Gln Ser Ile Asn Ser Gln
        475                 480                 485

TCA GTT GGT CCA TCA TTA ACA CAG CCA GCG ATG TCT CAA GCT GCA AAT    1900
Ser Val Gly Pro Ser Leu Thr Gln Pro Ala Met Ser Gln Ala Ala Asn
        490                 495                 500

TTA CCA ATT CCA CAA GGC ATG TCA CAG TTT CAG TTT TCA GCT CAG TTA    1948
Leu Pro Ile Pro Gln Gly Met Ser Gln Phe Gln Phe Ser Ala Gln Leu
505                 510                 515                 520

GGA GCC ATG CAG CAT CTA AAA GAC CAG CTA GAG CAG CGG ACA CGG ATG    1996
Gly Ala Met Gln His Leu Lys Asp Gln Leu Glu Gln Arg Thr Arg Met
                525                 530                 535

ATA GAG GCA AAT ATT CAT CGG CAG CAA GAA CTA AGG AAA ATT CAA        2044
Ile Glu Ala Asn Ile His Arg Gln Gln Glu Leu Arg Lys Ile Gln
        540                 545                 550
```

Fig. 8G

```
GAG CAA CTT CAG ATG GTC CAT GGT CAA GGG CTA CAG ATG TTT TTG CAG    2092
Glu Gln Leu Gln Met Val His Gly Gln Gly Leu Gln Met Phe Leu Gln
555                 560                 565

CAA TCA AAC CCT GGA TTG AAT TTT GGT TCT GTT CAA CTT TCC TCT GGA    2140
Gln Ser Asn Pro Gly Leu Asn Phe Gly Ser Val Gln Leu Ser Ser Gly
        570                 575                 580

AAT TCT AAT ATC CAG CAG CTC ACA CCT GTA AAT ATG CAA GGC CAG GTT    2188
Asn Ser Asn Ile Gln Gln Leu Thr Pro Val Asn Met Gln Gly Gln Val
585                 590                 595                 600

GTC CCT GCT AAC CAG GTT CAG AGT GGA CAT ATC AGC ACA GGC CAG CAC    2236
Val Pro Ala Asn Gln Val Gln Ser Gly His Ile Ser Thr Gly Gln His
        605                 610                 615

ATG ATA CAG CAA CAG ACT TTA CAA AGT ACA ACT CAG CAG CAG AGT CAA    2284
Met Ile Gln Gln Gln Thr Leu Gln Ser Thr Thr Gln Gln Gln Ser Gln
620                 625                 630

CAG AGT GTA ATG AGT GGA CAC AGT CAG CAG ACG TCT CTT CCA AGT CAG    2332
Gln Ser Val Met Ser Gly His Ser Gln Gln Thr Ser Leu Pro Ser Gln
        635                 640                 645
```

Fig. 8H

```
ACA CCG AGC ACT CTC ACA GCC CCA CTG TAC AAT ACG ATG GTG ATT TCC    2380
Thr Pro Ser Thr Leu Thr Ala Pro Leu Tyr Asn Thr Met Val Ile Ser
        650                     655                     660

CAG CCT GCA GCT GGG AGC ATG GTC CAG ATT CCA TCC AGT ATG CCA CAG    2428
Gln Pro Ala Ala Gly Ser Met Val Gln Ile Pro Ser Ser Met Pro Gln
        665                     670                     675                 680

AAC AGT ACC CAG AGT GCT ACA GTC ACT ACG TTC ACT CAG GAC AGA CAG    2476
Asn Ser Thr Gln Ser Ala Thr Val Thr Thr Phe Thr Gln Asp Arg Gln
                685                     690                     695

ATA AGA TTT TCT CAA GGT CAG CAA CTT GTG ACC AAA TTA GTG ACT GCT    2524
Ile Arg Phe Ser Gln Gly Gln Gln Leu Val Thr Lys Leu Val Thr Ala
        700                     705                     710

CCT GTA GCT TGT GGG GCC GTC ATG GTA CCA AGT ACC ATG CTT ATG GGT    2572
Pro Val Ala Cys Gly Ala Val Met Val Pro Ser Thr Met Leu Met Gly
        715                     720                     725

CAG GTG GTG ACT GCC TAT CCT ACC TTC GCC ACA CAA CAG CAG CAG GCA    2620
Gln Val Val Thr Ala Tyr Pro Thr Phe Ala Thr Gln Gln Gln Gln Ala
        730                     735                     740
```

Fig. 8I

```
CAG ACA TTA TCG GTA ACA CAA CAG CAG CAG CAG CAG CAG CAG CCA    2668
Gln Thr Leu Ser Val Thr Gln Gln Gln Gln Gln Gln Gln Gln Pro
745                 750                 755                 760

CCA CAG CAA CAG CAA CAA CAG CAG CAG CAG AGT TCC CAG GAA CAG CTT    2716
Pro Gln Gln Gln Gln Gln Gln Gln Gln Gln Ser Ser Gln Glu Gln Leu
        765                 770                 775

CCT TCA GTT CAG CAG CCA GCT CAG GCC CAG CTG GGC CAG CCA CCA CAG    2764
Pro Ser Val Gln Gln Pro Ala Gln Ala Gln Leu Gly Gln Pro Pro Gln
    780                 785                 790

CAG TTC TTA CAG ACA TCT AGG TTG CTC CAC GGG AAT CCT TCG ACA CAG    2812
Gln Phe Leu Gln Thr Ser Arg Leu Leu His Gly Asn Pro Ser Thr Gln
795                 800                 805

CTC ATC CTC TCT GCT GCC TTT CCA CTA CAA CAG AGC ACT TTC CCT CCT    2860
Leu Ile Leu Ser Ala Ala Phe Pro Leu Gln Gln Ser Thr Phe Pro Pro
        810                 815                 820

TCG CAC CAC CAG CAA CAC CAG CCT CAG CAA CAG CAG CTT CCT CGG    2908
Ser His His Gln Gln His Gln Pro Gln Gln Gln Gln Leu Pro Arg
825                 830                 835                 840
```

Fig. 8J

```
CAC AGG ACT GAC AGC CTG ACT GAC CCT TCC AAG GTC CAG CCA CAG T    2954
His Arg Thr Asp Ser Leu Thr Asp Pro Ser Lys Val Gln Pro Gln
              845                 850                 855

AGCACACACA CTTCCTCTCT GACATGCGAG AGGAAGGGGA TGGCCAGAAA GAATCGCTCA   3014
GTTGGCATGC GGTCAGAAGT TGAACAGTTT CACGAGGGTG GTCTTGAGTG TTCAGTCCCT   3074
TGATGAGACG GTAGGGAAGT GCTGCCCAGT GCTTCAGATG TCCATTAAAT ACCAGCCAGT   3134
GGGAAATGGT CATAGGGACA CAGCCAATTC TGACAGTTTC TTTGCCCAGG TATTTTTTGA   3194
TAGAAAGAGT ATATTGCCAA ATGCTAACAA GCTCAGCTAT CAACCAGATC TTTACTGAAT   3254
CCGAAGAGCA CTAACAGTGT TGGTAGCTTT AGTGGGTCTG TGCCTGCATC AAATATTACA   3314
GAGGGCACAC CACTGCCCAGG GGTTTGCTTA GAATGCCATG AAGATAGTCC AGTAGTTAAT   3374
AGTCCCCACC CCAAACTCCT CTCCCTGTTC AGACAATGAT GGAACCGTGA TGACTTTGAG   3434
AATGTTGTGC AGTTTGAAT TCACTGTGTA CAGATGCTGT AGTGTCTCTG TGTCTGGATG   3494
GAGGAGAGAA AGCCACTTTG ATACAGAAAG CATTATCTGT CCCTCACAGG TATGAGTGCA   3554
TTTCATTAGG TTTGACACCA TGTACAAACT GATAACAACC TCTCTTTTTT CATTTGTTT    3614
ACAACACAGT AGTGTTCTCG TTACTTTTCC AGGGCACAAG TCTTTTTGTC CGTGCTTTGG   3674
CTGTGATGTC ACAGTTTGTT CAGTGAGGTA ACAATGTGCT GCTGGGAATG GATTTTTTA    3734
AGGTTAAATT ATTGCTACAT TTCCACTTAC TCAGAAATAT CCCTTATTTC ATTATTTTTC   3794
AATTATGTT GAGAGAGTT GATATATTTC TTATTTATGA TGGTTGGTTG AGAGTTTAAT    3854
CACATATTT CAAGAATGTT ATAGTTGGAA TATTTATGTA AATGGTTTTC AACAAGCCTG    3914
AAAGTAATT ACATTCTCAG TCAGTTGTAA GAGTAAAGTT TGCACACAAA ACATTTTAGG   3974
CACTTTTTA AAAAATTCA AGGTGGGAAT TTTAACTTTT AGGATTTGTT GGAATCTTTT    4034
TATTATCTTT AAAAATTTCA ATGCTTCTTT TGATTCAGAA TGATTCAGGG TTATTGAGG    4094
GGAAAAAACC CATAGTGCCT TGATTTTAAT TCAGGTGATA ACTCACCATC TTGAATTCAT   4154
TGTCTGGTTT CAGTAGCAGT TTTGAAACCT TAGTACATTT TTAGCAGCAG TGTCATTCTC   4214
```

Fig. 8K

```
AAGTCCCCAT GAGGACTGCT GCGTCTCTTG GGCTGCCTGA CAGCGTCACA GCTGGGAATG   4274
GGATCCCAAA ATCGTTTCCT GTTTGCATCT TCCTCTAAAG CTAAGTAACT CTTTTAGGAA   4334
TTACCAGTAA ATACTTGCTC AGAGACAAGG GACAAGTTGT CTTTAATTTT CATTGCAGCA   4394
CTAGAATAAT GTAACTCACA TGCTTTTTAA ACATTAAGAT TTCATTTGGC AATATCATTC   4454
TCTACAGTTA ATAAACTCCA ACAAAGCTAC ATACATTTTA AAAGGCATTT TTTTAGATTT   4514
TATGGTACTA ATAATGAGTT TTTCAATTAA AGAACAAAAG ATCAGTAGGA TATAGAATAT   4574
CAAGTATTAC TGAGAAAAGG GAGGATAAGT GTGGCACATT AGAATTGACC TTAAAAGGAA   4634
AGTATGTGAT GGTGAGGTGC TAAACTGGTT TCAGCAGTGC AGATAACCTA AGGCAGAGTT   4694
GCTAGATCAG GGCTTGGGGA ACTCGGAGTC AGCTATCTGT CTCTAGCTTT GCTCTCATCA   4754
TCAGTAAGTG TGTCTTTGTT TTCCTGTTTA CCTGACTGCA ATTAAGTTAG CAAGTTAGTG   4814
ATAAAAAGAA AACAACCAAA GAAAATTGGT ACCTACTCTT CTGCGTAAGA AGTGTGTCTA   4874
GATACCAGTC AGTAACTCAC ATATCACAGA AGTTCTTCTA GCTGACATTC ATACGAATAC   4934
CAGAAATAGT TGTGAGAATA CACATTATG CAAGTTGTG CACACGTGAC GAAATCAATG   4994
TAAGTCGAGC ACCCACATTG CTTTTCTCCC TTCCACATTG CCTTCTTCTC TTTGGCCATT   5054
CCATGTCCTC GGAGTCGGAG CTGTGCCTCG TTTATCTTTT TGCATCACAT AGCGATAAGA   5114
ATTTAGCTAC AGGAGATACA ACATGCTAGT TATGTAATGC CTGCTGTTCT TCACAGTTCA   5174
TCTCCCCTGCT TAAAAGTAGC AGTTGATAAG AAACTCTAGC TGCTAAGGCT GCTGTCCACA   5234
CGGAGATGCA TGCTGGGCAA CAGTTGTCAG CACTAGCTC CTTAGCTC CTTAATTCTT   5294
GGTTCCTTTG GATGGCAAAC TGTCTTTGTC TGCTCCCCAC ACGACTCCAG TATTCTGAAG   5354
AAAGTTCATC TTTTGCCTGT TCATTTCTGT AGCCAAAGCT GACTGAAAACC CCAAATCTAA   5414
ATCATGAAAA GATACCAAAA AGAAACACTT CTCAGCTTCT TAGAAAACTT AACTTCTCTT   5474
GCTGTATTTC ATGGATTGA TTTTCTTTGA AATTTTTGAT TCTGGGCAGC GCCTTTTAAT   5534
TAAGAAATTG TTAGGATGAA GGTCAAACAG GTTCTCATTG CCCTGCAGT ACCTTGCTCT   5594
GGACTGCTTC TGTATGGGGT GACTTGGGGT TGCTGAACAC ACAGGATTAG AACAGTAAAC   5654
ACAAAGCTGC CCTTGAGGCT GGCGTTAAAC CAGAGCCTCA ATATTGAAAA TATCAAGTCC   5714
```

Fig. 8L

```
TCTTTCCTTC CTTAGAGACG AGACTGTGAG AGGAAAGCAA CTGTGGTAGG TGGGCTTGCT 5774
TGCACATGAG CACCAAGACC ATTCCCCAAG CTCTATCCTC AGGGTAGCAT TTAGAGTGCT 5834
GTGTTCTGCT GTCACATAGA CATGGCTTAG GGATGTAGCA CTAATAAAAG AATGCCCGTG 5894
CTTTGAATA GTTGTGATAG CAAACTCTAG GCTAACTAGC AAGTGTTGA ATTCTGTGTG 5954
CTGTATAGTA GTTGGTCATT GCCTTAAAGC AGTCTCTTGG AAGTTGGGAG CACTGAAGCA 6014
GTCCAACCAT ATATGGGCAT CACGTTGAGG GAGATGAGCC TTGTTCAAGC CTTAGAAAGG 6074
ACCCTAGTC TACACAGGTA GATTCTTTC ACTTGGATAT TACTGTGTTT AAAATGTTTC 6134
CACTATGTTG AGGCAGTTTT TTAAAGTGGA ACACAGATAG GATTTTTAGT ATTTCTTTTT 6194
TTGTTTCTT GGTGATTAAA GGTTTGTTGG TAGACATTTG TGTAAAAGTT GTTCAAGCCT 6254
ATCATCTTTC CAGTACTTGT GGTCCTGTTC TTAGTACCAG AGTCCACAAT GGAAAGTGTA 6314
AACACTGGAT ATTAATATTG CTGAGGGTGC ATAGCCAGGT GTGAGCTGAC TGGAACTTCT 6374
CAGTGGTGAA GAAACAGCAC AACGGCACTT GCCATTTTCA TAGTGATTGC ATAAAGAGAC 6434
CTTCTAAGTT TGTCTGGATT GAGTGAACAC TCTTCTAAGA GGAGCTTCTC AAGTAAATGC 6494
AAAGGAAAAG AGTTGACTAT TTTTATAGCA TATTAATAT ATTTGTATAT AACTATGAGT 6554
GTAGTAGGAA CCCTCCACAT GCCTCCCACT TTTCTAATTC CCTCCCCTTC TGCCGTAGCC 6614
CTAGTCCAGC CTCATCCGCA TGGGTAATGT GCCTACTGTC AGCCTACCTA CCAAAAGATA 6674
GTGCTGCTGC TTTCTGAGAC AGTGAGATC AGACTCTCAT GCCTGGGGAT CCTTATGGGA 6734
GGAATAGCAC ACACTTAGAA CAACATACCA CAGTTTAAGA GCATCATTTT GAAAGGTAAT 6794
AAGCACTTTA TTGCAATTAT TCATTTAGAT AAAGTTTGTA TCTTAGGCAT TAACCGTTTT 6854
TAAAGGATCC CTAATCATCA CTTAGGTGAA ATGATAAACG ACACATTTCT GAGAAATGTT 6914
CAGGTCCAGT GAACCGTAGC AGGTTTATGG GAATGATTTC AAGGTAGCCA AATAACTCT 6974
GACTTTTGTT TTGAATGTGG TGGAGTCAGG AGATTGTAGA TGTGTAGTT GATTAAACA 7034
CTATTGTAAA CCTATCTTGC CTATTGTGTG GACACCAAAA GAGACCAATG AGCCTGTTTA 7094
TTTTCAGAGG TCTAGGAATA TGCATCTGTC CTGAGTAGATA TACAGAACTA ATCTATAAAC 7154
GGTTGGTAGT AATATTTTAG GATACAGTAA CTTAAAGAAT TATTGAGTGT TTTAAATGTG 7214
```

Fig. 8M

```
CCCTGAAATG TTGGCATGTC ATTTCAGCGT TCCCATTTGA GTTGCTCTCTG TAATATTTTT   7274
GCACAAAAAG GACTGAGAAA AGACTGCTTT GGTTGAAGAA AACTATAATT TGGTCTTATT   7334
TTAATGTCTC CTGTGGAAAC ACTGGAGGTA AATTTGTTGG CATAGTTACT AATTCAGGAT   7394
ATTAAAACA GTGTTGAACA GCTCATCAGA AATTAAGCAA ACTTATATAT TTAAAAATTA   7454
AAAATCTTTT TTTCCATGTG ACTGAAAAAA AAAAAAAAAA AAAA                     7498
```

Fig. 9A
```
GCTGGAGAGAGAGGAAACCCCGGACGGCGAGAGCGCGAAGGAGAAATCTGGCCGCCGCCCGCGCACGCGCTCCCG
```

Fig. 9B
```
GGGGAGGAGCGCGGCGCGGTAGCGGTGAATTTTGAGGGGTGGGTCGGGGGCGCGCACTCGCCGCCCCTGGTGCTGCCG
GCTCCCGGAGCCGTGGCCGTGTCCCTGCTGTCGCGCCGCTGTGTCGCCGCTCGTGTCCGCCGGGCAGAGTCCCGGGCGG
GGAGGGAGGAAGCCGGAGCCTCAGGCACG
```

Fig. 9C
```
TGAAAGAAAAAGCACAAGAAGAAGAAACTTTTACAGGCGTTGTTGATTGGACTAGGCAACGATTCCCAAAATCACCAGC
AAG
```

Fig. 9D
```
AGTTCTGATGGTCAGTCACACAGAAGACGGGGCCTTGCGTCTCGTGTGGGTGTTGGAGACTCCATTCTAAAGATATAAAAA
GTGAAAGAG
```

Fig. 9E
GAGAAGTACAAATGTCTACCACAAGACGAAAACATAATGTGTTATGGTGTTACCGTAAGCTGTAGTAAAATGAGC
TCAATTGTTGACAG

Fig. 9F
AGATGACAGTAGTATTTTTGATGGATTGGTGTGGAAGAAGATGACAAGGACAAAGCAAAAAG

Fig. 9G
AGTATCTAGAAACAAATCAGAAAAGAAACGTAGAGATCAGTTCAATGTCCTCATTAAGGAGCTGGGGTCTATGCTT
CCTGGTAACGGCGAGAAAGATGGACAAGTCTACTGTTCTACAGAAGAGCATTGATTTTTTGCCAAACATAAAG

Fig. 9H
AGACCACTGCACAGTCAGATGCTAGTGAGATTCGACAGGACTGGAAACCCACATTCCCTTAGTAATGAAGAGTTTAC
ACAGTTAATGTTAGAG

Fig. 9I
GCTCTTGATGGTTTTTTTTTAGCGATCATGACAGATGGAAGTATAATATATGTATCTGAGAGTGTAACTTCGTTAC
TTGAACATTACCA

Fig. 9J
TCTGATCTTGTGTGGATCAAAGTATATATTTAATTTTATCCCAGAGGGGAGAACATTCAGAGGTTTATAAGATACTCTCTA
CTCATCTCTGGAAAGTGACTCATTAACCCCCTGAGTACTTAAAAT

Fig. 9K
CAAAAATCAGTTAGAATTCTGTTGTCACATGCTTCGAGGAACAATAGACCCAAAGGAGCCATCCACCTATGAATA
TGTGAGATTTATAGGAAATTTAAATCTTTAACCAGTG

Fig. 9L
TATCAACTTCAACACACAATGGTTTTGAAGGAACTATACAACGCCACACATAGGCCTTCTTATGAAGATAGAGTTTG
TTTTGTAGCTACTGTCAGATTAGCTACACCTCAGTTCATCAAG

Fig. 9M
GAAATGTGTACTGTTGAAGAACCAAATGAAGAGTTTACATCTAGACACAGTTTAGAATGGAAGTTTCTATTTTAG
ATCACAG

Fig. 9N
GGCACCACCAATAATAGGCTATTTGCCATTTGAAGTCTTGGGAACATCAGGCTATGATTACTATCATGTGGATGAC
CTAGAAAATCTGGCAAAATGTCACGAGCACT

Fig. 9O
TAATGCAATATGGAAAAGGCAAATCGTGTTACTATAGATTCCTGACCAAAGGCCAGCAGTGGATATGGCTTCAGAC
TCATTATTATATTACTTACCATCAGTGGAATTCAAGGCCAGAGTTCATTGTTGTACTCACACTGTAGTAAG

Fig. 9P
TTATGCAGAAGTTAGGGCTGAAAGACGGCGAGAACTTGGCATTGAAGAGTCTCTTCCTGAGACAGCTGCTGACAAA

Fig. 9Q
AGCCAAGATTCTGGTCTGACAATCGTATCAACACAGTGAGTCTCAAGGAAGCACTGGAAAGGTTTGATCACAGCC
CAACTCCTTCTGCCTCCTCTAGAAGCTCACGAAAGTCATCTCAGAGCCAGTCTCAGACCCTTCCT

Fig. 9R
CCACACCGACAAAGATCCCTACTGATATACTAGCCACTCCTCCCAGACAGCATTTGCCAGCTCATGAAAAGATGACACA
GCGGAGGTCGTCCTTCAG

Fig. 9S
TCCATAAACTCCCAGTCAGTTGGTCCATCATTAACACAGCCAGCGATGTCTCAAGCTGCAAATTTACCAATTCCAC
AAGGCATGTCACAG

Fig. 9T
TTTCAGTTTTCAGCTCAGTTAGGAGCCATGCAGCATCTAAAAGACCAGCTAGAGCAGCGGACACGGATGATAGAGG
CAAATATTCATCGGCAGCAAGAACTAAGGAAAATTCAAGAGCAACTTCAGATGGTCCATGGTCAAGGGCTACA
G

Fig. 9U
ATGTTTTGCAGCAATCAAACCCTGGATTGAATTTTGGTTCTGTTCAACTTTCCTCTGGAAATTCTAATATCCAGC
AGCTCACACCTGTAAATATGCAAGGCCAGGTTGTCCCTGCTAACCAGGTTCAGAGTGGACATATCAGCACAGGCCA
GCACATGATACAGCAACAGACTTTACAAAGTACACATCAACTCAG

Fig. 9V
CAGAGTCAACAGAGTGTAATGAGTGGACACAGTCAGCAGAGAGCGTCTCTTCCAAGTCAGACACCGAGCACTCTCACAG
CCCCACTGTACAATACGATGGTGATTCCCAGCCTGCAGCCTGCAGCATGGTCCAGCATGGTCCAGATTCCATCCAGTATGCCACA
GAACAGTACCCAGAGTGCTACAGTCACTACTACGTTCACTCAGGACAGACAGATAAG

Fig. 9W

ATTTTCTCAAGGTCAGCAACTTGTGACCAAATTAGTGACTGCTCCTGTAGCTTGTGGGCCGTCATGGTACCAAGTACCAT
GCTTATGGGTCAGGTGGTGACTGCCTATCCTACCTTCGCCACAACAGCAGCAGGCACAGAGACATTATCGGTAACACAACA
GCAGCAGCAGCAGCAGCAGCAGCCACCACCACAGCAACAGCAACAGCAGAGTTCCCAGGAACAGCAGCTTCCTTCAGT
TCAGCAGCCAGCTCAGGCCCAGCTGGCCAGCAGCCACCAGCAGTTCTTACAG

Fig. 9X

ACATCTAGGTTGCTCCACGGGAATCCTTCGACACAGCTCATCCTCTGCCTTCCACTACAACAGAGCACTTTCCCT
CCTTCGCACCACCAGCAACACCAGCTCAGCAGCAACAGCACTTCCTCGGCACAGGACCTTGACAGCCTGACCCTTCC
AAGGTCCAGCCACAGTAGCACACACTTCCTCTGACATGCGAGAGGAAGGGATGGCCAGAAAGAATCGCTCAGTTGG
CATGCGGTTCAGAAGTTGAACAGTTTCACGAGGGTGGTTCAGTCCCTTGATGAGACGGTAGGGAAGTGCTGCC
CAGTGCTTCAGATGTCCATTAAATACCAGCCAGTGGGAAATGGTCATAGGGACACAGCCAATTCTGACAGTTCTTTGCCC
AGTATTTTTGATAGAAAGAGTATATTGCCAAATGCTAACAAGCTCAGCTATCAACCAGATCTTTACTGAATCCGAAGAG
CACTAACAGTGTTGGTAGCTTTGGTAGTCCCTGTGTGCCTGCATCAAATATTACAGAGGGCACACCACTGCCAGGGTTTGCTT
AGAATGCCATGAAGATAGTCCAGTAGTTAATAGTCCCCACCCCCAAACTCCTCCCTGTTCAGACAATGATGGAACCGTGA
TGACTTTGAGAATGTTGTGCAGTTTGAATTCACTGTGTACAGATGCTGTAGTGTCTCTGTGATGGAGGAGAAA
GCCACTTTGATACAGAGAAAGCATTATCTGTCCCTCACAGGTATGAGTGCATTCATTAGGTTTGACACCATGTACAAACTGA
TAACAACCTCTCTTTTTCATTTTGTTTACAACACAGTAGTGTTCTCGTTACTTTTCCAGGCACACAAGTCTTTTTGTCCGT
GCTTTGGCTGTGATGTCACAGTTGTTCAGTGAGGTAACAATGTGCTGCTGGGAATGGATTTTTAAGGTATAATTATTG
CTACATTTCCACTTACTCCAGAAATCCCTTATTCCAATTATGTTGGAATATTTATATTTCATAGTTGGAATATTATATCAACAAG
TTAGATGGTTGGTTGAGAGTTTCAAGAAATGTTCAGTTGTAAGAGTAAAGTTTGCACACAAAACATTTTAGGCACTTTTTAACATTCT
CCTGAAAGTAATTTTCAAGAAATGTTCAGTTGTAAGAGTAAAGTTTGCACACAAAACATTTTTAAAAATTGAATGCTTCTTTTAGTCAGA
CAGAGGTGGGAATTTTAACTTTTGAGGGGAAAAAACCCATAGTCCCTTGATTTTAATTCAGTGATAACTCACCATCTTGAATTCA
AATGATTCAGGGTTATTTGAGGCAGTTTGAAACCTTAGTACATTTTTAGCAGCAGTGTCATTCTCAAGTCCCATGAGGACTGCT
TTGTCTGTTTCAGTAGCAGTTTCAGTGCCTGACAGCGTGGGATCCCAAAATCGTTCCTGTTGCATCTTCCTCTAAAGC
GCGTCTCTTGGGCTGCCTGACAGCGTGGGATCCCAAAATCGTTCCTGTTGCATCTTCCTCTAAAGC
TAAGTAACTCTTTTTAGGAATTACCAGTAAATACTTGCTCAGAGACAAGGGACAAGTT

Fig. 9Y

```
GTCTTTAATTTCATTGCAGCACTAGAATAATGTAACTCACATGCTTTTAAACATTAAGATTTCATTGGCAATATCATTCT
CTACAGGTAATAAACTCCAACAAAGCTACACATACATTTTAAAAGGCATTTTTTAGATTTTATGGTACTAATAATGAGTTTTC
AATTAAAGAACAAAGATCAGTAGGATATAGAATATCAAGTATTACTGAGAAAAGGAGGATAAGTGTGGCACATTAGAATTG
ACCTTAAAGGAAAGTATGTGAGGTGCTAAACTGGTTTGCTCTCAGTGGTTCAGCAGTGCAGATAAGCTAAGGCAGAGTTGCTAGATCAG
GGCTTGGGGAACTCGGAGTCAGCTATCTGTCTGCTCTAGCTTTGCTCTCATCATCAGTAAGTGTGTCTTGTTTTCCTGTTACCT
GACTGCAATTAAGTTAGCAAGTTAGTGATAAAAAGAAAACAACCAAAGAGAAAATTGGTACCTACTCTTCTGCGTAAGAAGTGTG
TCTAGATACCAGTCAGTAACTCACATATCACAGAGAAGTTCTTCTAGCTGACATTCATACGAATACAGAAATAGTTGTGAGAAT
ACACATTTATGCAAGTTTGTGCACACGTGACGAGAAATCAATGTAAGTCGAGCTGTGCCTCGTTATCTGCTTTTCTCCCTTCCACATTGCC
TTCTTCTCTTGGCCATTCCATGTCCTCGGAGTCGGAGCTGTGCCTCGTTATCTTTTTGCATCACATAGCGATAAGAATTTA
GCTACAGGAGATACAACATGCTAGTTATGTAATGCCTCGTGCTTCTTCACAGTTCATCTCCCTGCTTAAAAGTAGCAGTTGATA
AGAAACTCTAGCTGCTAAGGCTGCTGTCCACACGGAGATGCATGCTGGGCAACAGTGTCAGCACTAGCTGCCCTCTAGCTCC
TTAATTCTTGGTTCCTTGGATGGCAAAGCTGACTGAAACCCCAAATCTAAATCATGAAAGATACCAAAAGAAACACTTCTCAGCT
GCCTGTTCATTTCTGTAGCAAGCTTAACTTCTCTTGCTGTATTCATGGATTTGATTTCTTTGAAATTTCTGGGCAGCGCCTTTAAT
TCTTAGAAACCTTAACTTCTCTTGCTGTATTCATGGATTTGATTTCTTTGAAATTTCTGGGCAGCGCCTTTAAT
TAAGAAATTGTTAGGATGAAGGTCAAACAGTTCTCATTGCCCTGCAGGTACCTTGCTCTGGACTGCTTCTGTATGGGGTGAC
TTGGGGTTGCTGAACACACAGATTAGAACAGTAAACACAAAGCTGCCCTTGAGGCTGGCGTTAAACCAGAGCCTCAATATTG
AAATATCAAGTCCTCTTCCTTTCCCTTAGAGACGAGACAACTGTGGTAGGTGGCTTGCTGTCACATGACATGA
GCACCAAGACCATTCCCCAAGCTCTATCCTCAGGGTAGCATTAGAGTGCTGTGTTCTGCTGTCACATAGCACATGCTTAGGG
ATGTAGCACTAATAAAAGAATGCCCGTGCTTTGAATAGTTGTGATAGCAAACTCTAGCTAACTAGCAAGTGTTGAATTCT
GTGTGCTGTATAGTAGTTGGTCCTTGCCTTAAAGCAGTCTCTTGGAAGTTGGGAGCAGTCCAACCATATATGGGC
ATCACGTTGAGGGAGATGAGCCTTGTTCAAGCCTTGTCAAGGACCCTTAGTCTACACAGGTAGATTCTTTTCACTTGGATATT
ACTGTGTTAAAATGTTTCCACTATGTTGAGGCAGTTTGAGGAACACAGATAGGATTTTTAGTATTTCTTTTTTGT
TTCTTTGGTGATTAAGGTTTGTTGGTAGACATTGTTCAAGCAGTTGTTGTAAAAGTTGTTCCAGTACTGTGTCCTG
TTCTTAGTACCAGAGTCCACAATGGTAAACACTGGATATTAATATTGCTGAGGGTGCATAGCCAGTGTGAGCTGAC
TGGAACTTCCAGTGGTGAAGAAACAGCACACGGCACTTGCCATTTCATAGTGATTGCATAAAGAGACCTTCTAAGTTTGT
CTGGATTGAGTGAACACTCTTCTAA
```

Fig. 9Z

```
GAGGAGCTTCTCAAGTAAATGCAAAGGAAAAGAGTTGACTATTTTTATAGCATATTTAATATATATTTGTATATAACT
ATGAGTGTAGTAGGAACCCTCCACATGCCTCCCACTTTTCTAATTCCCCTTCTGCCGTAGCCCTAGTCCAGC
CTCATCCGCATGGGTAATGTGCCTACTGTGCCTCAGCCTACCACCAAAAGATAGTGCTGCTTTCTGAGACAGGTGA
GATCAGACTCTCATGCCTGGGATCCTTATGGGAGGAATAGCACACACTTAGATAAAGTTTGTATCTTAGGCATTAACCGTT
ATCATTTTGAAAGGTAATAAGCACTTTATTGCAATTATTCATTTAGATAAACGACACATTTCTGAGAAATGTTCAGGTCCAGTGAAC
TTTAAAGGATCCCTAATCACTTAGGTGAAATGATAAACGACACATTTCTGAGAAATGTTCAGGTCCAGTGAAC
CGTAGCAGGTTTATGGGAATGATTTCAAGGTAGCCAAATAAACTCTGACTTTTGTTTTGAATGTGGTGGAGTCAGG
AGATTGTAGATGTGTAGTTTGATTTAAACACTATTGTAAACCTATCTTGCCTATTGTGGGACACCAAAAGAGACC
AATGAGCCTGTTTATTTCAGAGGTCTAGGAATATGCATCGTCTGAGTAGATACAGAACTAATCTATAAACGG
TTGGTAGTAATATTTAGGATACAGTAACTTAAAGAATTATTGAGTGTTTAAATGTGCCCTGAAATGTTGGCATG
TCATTTCAGCCGTTCCCATTTGAGTTGCTCTTGAGTTGCTCTTGTAATATTTTTGCACAAAAAGGACTGAGAAAAGACTGCTTTGGTT
GAAGAAACTATAATTGGTCTTATTTTAAGCAAACACTGGAGGTAAATTGTTGGCATAGTTACT
AATTCAGATATATTAAAACAGTGTTGAACAGCTCATCAGAATTAAGCAAACTTATATATTAAAAATTAAAAATC
TTTTTTCCATGTGACTG
```

Fig. 10A

| SEQ ID NO. | Exon # | Exon Size | ...EXON/INTRON.... | Intron Size | ...INTRON/EXON.... | Exon # | SEQ ID NO. |
|---|---|---|---|---|---|---|---|
| 4 | 1a | 71 | GCGCTCCCGgtgagtgcg | | | | |
| 5 | 1b | 189 | TCAGGCACGgtgaggacg | 0.9kb | tctggtgttttctattgcagTGAAAGAAA | 2 | 27 |
| 6 | 2 | 79 | ACCAGCAAGgtaatttcc | >22kb | ctttgttttttaaaacagAGTTCTGAT | 3 | 28 |
| 7 | 3 | 85 | GTGAAAGAGgtaaaggcg | 7.0kb | atgtttcttttctcacaagGAGAAGTAC | 4 | 29 |
| 8 | 4 | 90 | TGTTGACAGgtatgtttt | 0.4kb | ctctgtctttcttgtagAGATGACAG | 5 | 30 |
| 9 | 5 | 60 | AGCAAAAAGgtagttagc | 0.4kb | taattcttttcttcatagAGTATCTAG | 6 | 31 |
| 10 | 6 | 149 | AACATAAAGgtaaagtgc | 3.0kb | acgtgtcaatctgtttacagAGACCACTG | 7 | 32 |
| 11 | 7 | 92 | ATGTTAGAGgtatgttca | 8.2kb | accattatgtttaatttcagGCTCTTGAT | 8 | 33 |
| 12 | 8 | 90 | CATTTACCAgtaagtatg | 5.9kb | tttttttttattttcagTCTGATCTT | 9 | 34 |
| 13 | 9 | 121 | ACTTAAAATgtaagtagg | 2.8kb | cttttatcacttattccagCAAAAAATC | 10 | 35 |
| 14 | 10 | 114 | TAACCAGTGgtaagttaa | 0.1kb | atgtctccctgctgtttagTATCAACTT | 11 | 36 |
| 15 | 11 | 119 | TTCATCAAGgtatgcttc | 2.0kb | acttgtaattgtttgtagGAAATGTGT | 12 | 37 |
| 16 | 12 | 83 | AGATCACAGgtaacatta | 0.2kb | attattactgtataattagGGCACCACC | 13 | 38 |
| 17 | 13 | 107 | ACGAGCACTgtaagtagc | 0.8kb | tttattttttatttttagTAATGCAAT | 14 | 39 |
| 18 | 14 | 148 | TGTAGTAAGgtaataact | 0.9kb | ttggttcttccattgtágTTATTGCAG | 15 | 40 |
| 19 | 15 | 76 | GCTGACAAAgtatgtttc | 3.7kb | tgttcctctatctcctagAGCCAAGAT | 16 | 41 |
| 20 | 16 | 142 | ACCCTTCCTgtgagtgcc | 0.6kb | tctctgttgactgtcttagCCACACCGA | 17 | 42 |
| 21 | 17 | 101 | AGCAGTCAGgtacgcctt | 0.4kb | atcttttatttgcttctagTCCATAAAC | 18 | 43 |

Fig. 10B

| SEQ ID NO. | Exon # | Exon Size | ....EXON/INTRON.... | Intron Size | ....INTRON/EXON.... | Exon # | SEQ ID NO. |
|---|---|---|---|---|---|---|---|
| 22 | 18* | 90 | ATGTCACAGgtattttg | 4.2kb | ctttccatgtgctgcttcagTTTCAGTTT | 19 | 44 |
| 23 | 19 | 153 | GGGCTACAGgtaacttat | 1.0kb | tgtgatctttgtttcaaagATGTTTTG | 20 | 45 |
| 24 | 20 | 195 | TCAACTCAGgtaattgac | 0.6kb | ttccatacgatcttttctagCAGAGTCAA | 21 | 46 |
| 25 | 21 | 206 | ACAGATAAGgtagttgtc | 2.1kb | tattttgttttctctcacagATTTTCTCA | 22 | 47 |
| 26 | 22 | 295 | TTCTTACAGgtaaccccc | >9.2kb | atcatccttttgttttttagACATCTAGG | 23 | 48 |
| 49 | 19 | 153 | GGGCTACAGgtaacttat | Wild type | | | |
| 50 | 19 | 153 | GGGCTACAGgttacttat | Clock Mutant | | | |

Fig. 11A

```
Cn  M-------    --------    --------    ------DEDE  KDRAKRASRN  KSEKKRRDQF  NVLIKELSSM  LPGNIRKMDK   70
MN  M-------    --------    --------    ------DEDE  KDRAKRASRN  KSEKKRRDQF  NVLIKELSSM  LPGNIRKMDK   45
HN  M-------    --------    --------    ------DEDE  KDRAKRASRN  KSEKKRRDQF  NVLIKELSSM  LPGNIRKMDK   45
Cl  MVFTVSCSKM  SSIVDRDDSS  IFDGLVEEDD  KDKAKRVSRN  KSEKKRRDQF  NVLIKELGSM  LPGNARKMDK   70

Cn  ITVLEKVIGF  LQKHNEVSAQ  TEICDIQQDW  KPSFLSNEEF  TQLMLEALDG  F.IAVTTDGS  IIYVSDSITP  140
MN  ITVLEKVIGF  LQKHNEVSAQ  TEICDIQQDW  KPSFLSNEEF  TQLMLEALDG  FVIVVTTDGS  IIYVSDSTTP  115
HN  ITVLEKVIGF  LQKHNEVSAQ  TEICDIQQDW  KPSFLSNEEF  TQLMLEALDG  FIIAVTTDGS  IIYVSDSITP  115
Cl  STVLQKSIDF  LRKHKETTAQ  SDASEIRQDW  KPTFLSNEEF  TQLMLEALDG  FFLAIMTDGS  IIYVSESVTS  140

Cn  LLGHLPSDVM  DQNLLNFLPE  QEHSEVYKIL  SSHMLVTDSP  SPEYLKSDND  LEFYCHLLRG  SLNPKEFPTY  210
MN  LLGHLPADVM  DQNLLNFLPE  QEHSEVYKIL  SSHMLVTDSP  SPEFLKSDND  LEFYCHLLRG  SLNPKEFPTY  185
HN  LLGHLPSDVM  DQNLLNFLPE  QEHSEVYKIL  SSHMLVTDSP  SPEYLKSDSD  LEFYCHLLRG  SLNPKEFPTY  185
Cl  LLEHLPSDLV  DQSIFNFIPE  GEHSEVYKIL  STHLLESDSL  TPEYLKSKNQ  LEFCCHMLRG  TIDPKEPSTY  210

Cn  EYIKFVGNFR  SYNNVPSPSC  NGFDNTLSRP  CRVPLGK.VC  FIATVRLATP  QFLKEMC.VD  EPLEEFTSRH  280
MN  EYIKFVGNFR  SYNNVPSPSC  NGFDNTLSRP  CHVPLGKDVC  FIATVRLATP  QFLKEMCVAD  EPLEEFTSRH  255
HN  EYIKFVGNFR  SYNNVPSPSC  NGFDNTLSRP  CRVPLGKEVC  FIATVRLATP  QFLKEMCIVD  EPLEEFTSRH  255
Cl  EYVRFIGNFK  SLTSVSTSTH  NGFEGTIQRT  HRPSYEDRVC  FVATVRLATP  QFIKEMCTVE  EPNEEFTSRH  280
```

Fig. 11B

```
Cn  SLEWKFLFLD HRAPPIIGYL PFEVLGTSGY DYYHIDDLEL LARCHQHLMQ FGKGKSCCYR FLTKGQQWIW  350
MN  SLEWKFLFLD HRAPPIIGYL PFEVLGTSGY NYYHIDDLEL LARCHQHLMQ FGKGKSCCYR FLTKGQQWIW  325
HN  SLEWKFLFLD HRAPPIIGYL PFEVLGTSGY DYYHIDDLEL LARCHQHLMQ FGIGKSCCYR FLTKGQQWIW  325
Cl  SLEWKFLFLD HRAPPIIGYL PFEVLGTSGY DYYHVDDLEN LAKCHEHLMQ YGKGKSCCYR FLTKGQQWIW  350

Cn  LQTHYYITYH QWNSKPEFIV CTHSVVSYAD VRVERRQELA LEDPP.EA.H .SA.K.KDSS LEPRQ.FNAL  420
MN  LQTHYYITYH QWNSKPEFIV CTHSVVSYAD VRVERRQELA LEDPPTEAMH PSAVKEKDSS LEPPQPFNAL  395
HN  LQTHYYITYH QWNSKPEFIV CTHSVVSYAD VRVERRQELA LEDPPSEALH SSALKDKGSS LEPRQHFNAL  395
Cl  LQTHYYITYH QWNSRPEFIV CTHTVVSYAE VRAERRRELG IEESLPE--- TAADKSQDSG SDNRINTVSL  417

Cn  D.GASGL..S PSPSASSRSS HKSSHTAMSE PISTPTKLMA E.ST.ALPR. ATLPQELPV. GLSQAATMP.  490
MN  DMGASGLPSS PSPSASSRSS HKSSHTAMSE PISTPTKLMA ENSTTALPRP ATLPQELPVQ GLSQAATMPT  465
HN  DVGASGLNTS HSPSASSRSS HKSSHTAMSE PISTPTKLMA EASTPALPRS ATLPQELPVP GLSQAATMPA  465
Cl  KEALEREDHS PTPSASSRSS RKSSHTAVSD PSSTPTKIPT DTST---PPR QHLPAHEKMT QRRSSFSSQS  484

Cn  .L.SS.SCDL TQQLL.Q..P QT.LQS.PAP ..QFSAQFSM FQTIKDQLEQ RTRILQANIR WQQELHKIQ  560
MN  ALHSSASCDL TKQLLLQSLP QTGLQSPPAP VTQFSAQFSM FQTIKDQLEQ RTRILQANIR WQQELHKIQ  535
HN  PLPSLSCDL  TQQLL----P QTVLQSTPAP MAQFSAQFSM FQTIKDQLEQ RTRILQANIR WQQELHKIQ  531
Cl  INSQSVGPSL TQPAMSQAAN LPIPQGMSQ- -FQFSAQLGA MQHLKDQLEQ RTRMIEANIH RQQELRKIQ  552
```

Fig. 11C

```
Cn  EQLCLVQDSN  VQMFLQQPAV  SLSFSSIQRP  .AQQQLQQR.  AA..QPQLV.  ..QLQGQI.S  T--QVT.QHL  630
MN  EQLCLVQDSN  VQMFLQQPAV  SLSFSSIQRP  AAQQQLQQRP  AAPSQPQLVV  NTPLQGQITS  T--QVTNQHL  603
HN  EQLCLVQDSN  VQMFLQQPAV  SLSFSSIQRP  EAQQQLQQRS  AAVTQPQLGA  GPQLPGQISS  A--QVTSQHL  599
Cl  EQLQMVHGQG  LQMFLQQSNP  GLNFGSVQLS  SGNSNIQQLT  PVNMQGQVVP  ANQVQSGHIS  TGQHMIQQQT  622

Cn  LRESSVIS.Q  GPKPMRSSQL  ...SGRS.SS  L.SPFSST..  .LPP.L.--L  TTPASTPQD.  SQCQPSPDF.  700
MN  LRESNVISAQ  GPKPMRSSQL  LPASGRSLSS  LPSQFSSTAS  VLPPGLS--L  TTIAPTPQDD  SQCQPSPDFG  671
HN  LRESSVISTQ  GPKPMRSSQL  MQSSGRSGSS  LVSPFSSATA  ALPPSLN--L  TTPASTSQDA  SQCQPSPDFS  667
Cl  LQSTSTQQSQ  QSVMSGHSQQ  TSLPSQTPST  LTAPLYNTMV  ISQPAAGSMV  QIPSSMPQNS  TQSATVTFT  692

Cn  HDRQLRLLLS  QPIQPMMPGS  CDARQPSEVS  RTGRQVKYAQ  SQ..F..PD.  HP.NSS....  PVLLMGQAVL  770
MN  HDRQLRLLLS  QPIQPMMPGS  CDARQPSEVS  RTGRQVKYAQ  SQVMFPSPDS  HPTNSSAST-  PVLLMGQAVL  740
HN  HDRQLRLLLS  QPIQPMMPGS  CDARQPSEVS  RTGRQVKYAQ  SQTVFQNPDA  HPANSSSAPM  PVLLMGQAVL  737
Cl  QDRQIRFSQG  QQLVTKLVTA  PVACGAVMVP  STMLMGQVVT  AYPTFATQQQ  QAQTLSVTQQ  QQQQQQPPQ  762

Cn  H------PSF  PAS.PSPLQP  AQAQQQPPP.  ....QAPTSL  HSEQ.DSLLL  STFSQQPGTL  GY...Q..QP  840
MN  H------PSF  PASRPSPLQP  AQAQQQPPPY  --LQAPTSL  HSEQPDSLLL  STFSQQPGTL  GYAATQSTPP  801
HN  H------PSF  PASQPSPLQP  AQARQQPPQH  YLQVQAPTSL  HSEQQDSLLL  STYSQQPGTL  GYPQPPPAQP  801
Cl  QQQQQQSSQ   EQQLPSVQQP  AQAQLGQPPQ  QFLQTSRLLH  GNPSTQLILS  AAFFPLQQSTF  PPSHHQQHQP  832

Cn  QP.RP.RRVS  .LSES.....  .P.                                                         863
MN  QPPRPSRRVS  RLSES-----  ---                                                         816
HN  QPLRPPRRVS  SLSESSGLQQ  PPR                                                         824
Cl  QQQQQLPRHR  TDSLTDPSKV  QPQ                                                         855
```

```
MVFTVSCSKMSSIVDRDDSS  IFDGLVEEDDKDKAKRVSRN  KSEKKRRDQFNVLIKELGSM    60
                                            |------bHLH domain------|
|----------------------------------------------------
LPGNARKMDKSTVLQKSIDF  LRKHKETTAQSDASEIRQDW  KPTFLSNEEFTQLMLEALDG   120
--------|                                            *******
*******PAS A****************************************
FFLAIMTDGSIIYVSESVTS  LLEHLPSDLVDQSIFNFIPE  GEHSEVYKILSTHLLESDSL   180

TPEYLKSKNQLEFCCHMLRG  TIDPKEPSTYEYVRFIGNFK  SLTSVSTSTHNGFEGTIQRT   240
                                          |-------PAS B----------
HRPSYEDRVCFVATVRLATP  QFIKEMCTVEEPNEEFTSRH  SLEWKFLFLDHRAPPIIGYL   300
---------------------------------------------------------------|
PFEVLGTSGYDYYHVDDLEN  LAKCHEHLMQYGKGKSCYYR  FLTKGQQWIWLQTHYYITYH   360

QWNSRPEFIVCTHTVVSYAE  VRAERRRELGIEESLPETAA  DKSQDSGSDNRINTVSLKEA   420

LERFDHSPTPSASSRSSRKS  SHTAVSDPSSTPTKIPTDTS  TPPRQHLPAHEKMTQRRSSF   480
```

Fig. 12A

```
                -----Deleted in Mutant-----
SSQSINSQSVGPSLTQPAMS QAANLPIPQGMSQFQFSAQL GAMQHLKDQLEQRTRMIEAN  540

IHRQQEELRKIQEQLQMVHG QGLQMFLQQSNPGLNFGSVQ LSSGNSNIQQLTPVNMQGQV  600

VPANQVQSGHISTGQHMIQQ QTLQSTSTQQSQQSVMSGHS QQTSLPSQTPSTLTAPLYNT  660

MVISQPAAGSMVQIPSSMPQ NSTQSATVTFTQDRQIRFS  QGQQLVTKLVTAPVACGAVM  720

VPSTMLMGQVVTAYPTFATQ QQQAQTLSVTQQQQQQQQP  PQQQQQQQSSQEQQLPSVQ   780

QPAQAQLGQPPQQFLQTSRL LHGNPSTQLILSAAFPLQQS TFPPSHHQQHQPQQQQLPR   840

HRTDSLTDPSKVQPQ                                                855
```

Fig. 12B

```
                                          ------bHLH domain------
MVFTVSCSKMSSIVDRDDSS IFDGLVEEDDKDKAKRVSRN KSEKKRRDQFNVLIKELGSM   60
-------------------- --------
                                                         ******
LPGNARKMDKSTVLQKSIDF LRKHKETTAQSDASEIRQDW KPTFLSNEEFTQLMLEALDG  120
              --------------------------
************PAS A*************************
FFLAIMTDGSIIYVSESVTS LLEHLPSDLVDQSIFNFIPE GEHSEVYKILSTHLLESDSL  180
--------------------

TPEYLKSKNQLEFCCHMLRG TIDPKEPSTYEYVRFIGNFK SLTSVSTSTHNGFEGTIQRT  240

------PAS B---------
HRPSYEDRVCFVATVRLATP QFIKEMCTVEEPNEEFTSRH SLEWKFLFLDHRAPPIIGYL  300
--------------------

PFEVLGTSGYDYYHVDDLEN LAKCHEHLMQYGKGKSCYYR FLTKGQQWIWLQTHYYITYH  360
-------------

QWNSRPEFIVCTHTVVSYAE VRAERRRELGIEESLPETAA DKSQDSGSDNRINTVSLKEA  420

LERFDHSPTPSASSRSSRKS SHTAVSDPSSTPTKIPTDTS TPPRQHLPAHEKMTQRRSSF  480
```

Fig. 13A

```
---------Deleted in Mutant---------
SSQFQFSAQLGAMQHLKDQL EQRTRMIEANIHRQQEELRK IQEQLQMVHGQGLQMFLQQS  540
 /\
exon 18 (30 aa) spliced out

NPGLNFGSVQLSSGNSNIQQ LTPVNMQGQVVPANQVQSGH ISTGQHMIQQQTLQSTSTQQ  600

SQQSVMSGHSQQTSLPSQTP STLTAPLYNTMVISQPAAGS MVQIPSSMPQNSTQSATVTT  660

FTQDRQIRFSQGQQLVTKLV TAPVACGAVMVPSTMLMGQV VTAYPTFATQQQAQTLSVT   720

QQQQQQQQPPQQQQQQQQS  SQEQQLPSVQQPAQAQLGQP PQQFLQTSRLLHGNPSTQLI  780

LSAAFPLQQSTFPPSHHQQH QPQQQQQLPRHRTDSLTDPS KVQPQ                 825
```

```
CATGCCTCAG GATACTCCTC AATAGCCATC GCTGTAGTAT ATCCAAAGAC AACCATCATT      60
CCCCCCCCCC GGCCCCTGG AGCGAGAGCG CGAAGGAAAT CTGGCCGCCG CCGCCGCGAG     120
CGCTCCCGAA TTTTACTTG TTCCTGCAAA GCTGCTGGAG CTCAGAAGCT GATTCTATCA     180
CATTGTAAGA TGCCTTTGGA TAATTCTACA GTCCTCTTAA ATGAATCTTT AGAACTTGGC    240
AAGTCTCACT AGATACCTTC AATCATCATT TTGAGCTCAA AGAATTCTGA GACTTATGGT    300
TGGTCATATA GAAGAGTACC TTGAACCTAT AGTTTCCTGA AGAATCAGTT TAAAAGATCC    360
AAGGAGTACA AAAGGAGAAG TACAAATGTC TACTACAAGA CGAAAACGTA GTATGTT       417

ATG TTT ACC GTA AGC TGT AGT AAA ATG AGC TCG ATT GTT GAC AGA           465
 M   F   T   V   S   C   S   K   M   S   S   I   V   D   R
 1               5                  10                  15

GAT GAC AGT AGT ATT TTT GAT GGG TTG GTG GAA GAT GAC AAG GAC           513
 D   D   S   S   I   F   D   G   L   V   E   D   D   K   D
         20                  25                  30

AAA GCG AAA AGA GTA TCT GAA AAC AAA TCT GAA AAG AAA CGT AGA GAT       561
 K   A   K   R   V   S   E   N   K   S   E   K   K   R   R   D
             35                  40                  45

CAA TTT AAT GTT CTC ATT AAA GAA CTG GGA TCC ATG CTT CCT GGT AAT       609
 Q   F   N   V   L   I   K   E   L   G   S   M   L   P   G   N
     50                  55                  60
```

Fig. 14B

```
GCT AGA AAG ATG GAC AAA TCT ACT GTT CTG CAG AAA AGC ATT GAT TTT    657
 A   R   K   M   D   K   S   T   V   L   Q   K   S   I   D   F
 65                  70                  75                  80

TTA CGA AAA CAT AAA GAA ATC ACT GCA CAG TCA GAT GCT AGT GAA ATT    705
 L   R   K   H   K   E   I   T   A   Q   S   D   A   S   E   I
                 85                  90                  95

CGA CAG GAC TGG AAA CCT ACA TTC CTT AGT AAT GAA GAG TTT ACA CAA    753
 R   Q   D   W   K   P   T   F   L   S   N   E   E   F   T   Q
             100                 105                 110

TTA ATG TTA GAG GCT CTT GAT GGT TTT TTT TTA GCA ATC ATG ACA GAT    801
 L   M   L   E   A   L   D   G   F   F   L   A   I   M   T   D
 115                 120                 125

GGA AGC ATA ATA TAT GTG TCT GAG AGT GTA ACT TCA CTT GAA CAT         849
 G   S   I   I   Y   V   S   E   S   V   T   S   L   E   H
 130                 135                 140

TTA CCA TCT GAT CTT GTG GAT CAA AGT ATA TTT AAT TTT ATC CCA GAA    897
 L   P   S   D   L   V   D   Q   S   I   F   N   F   I   P   E
 145                 150                 155                 160
```

Fig. 14C

```
GGG GAA CAT TCA GAG GTT TAT AAA ATA CTC TCT ACT CAT CTG CTG GAA    945
 G   E   H   S   E   V   Y   K   I   L   S   T   H   L   L   E
                165                 170                 175

AGT GAT TCA TTA ACC CCA GAA TAT TTA AAA TCA AAA AAT CAG TTA GAA    993
 S   D   S   L   T   P   E   Y   L   K   S   K   N   Q   L   E
                180                 185                 190

TTC TGT TGT CAC ATG CTG CGA GGA ACA ATA GAC CCA AAG GAG CCA TCT   1041
 F   C   C   H   M   L   R   G   T   I   D   P   K   E   P   S
                195                 200                 205

ACC TAT GAA TAT GTA AAA TTT ATA GGA AAT TTC AAA TCT TTA AAC AGT   1089
 T   Y   E   Y   V   K   F   I   G   N   F   K   S   L   N   S
                210                 215                 220

GTA TCC TCT TCA GCA CAC AAT GGT TTT GAA GGA ACT ATA CAA CGC ACA   1137
 V   S   S   S   A   H   N   G   F   E   G   T   I   Q   R   T
                225                 230                 235                 240

CAT AGG CCA TCT TAT GAA GAT AGA GTT TGT TTT GTA GCT ACT GTC AGG   1185
 H   R   P   S   Y   E   D   R   V   C   F   V   A   T   V   R
                245                 250                 255
```

Fig. 14D

```
TTA GCT ACA CCT CAG TTC ATC AAG GAA ATG TGC ACT GTT GAA GAA CCC    1233
 L   A   T   P   Q   F   I   K   E   M   C   T   V   E   E   P
            260                 265                 270

AAT GAA GAG TTT ACA TCT AGA CAT AGT TTA GAA TGG AAG TTT CTG TTT    1281
 N   E   E   F   T   S   R   H   S   L   E   W   K   F   L   F
            275                 280                 285

CTA GAT CAC AGG GCA CCA CCC ATA ATA GGG TAT TTG CCA TTT GAA GTT    1329
 L   D   H   R   A   P   P   I   I   G   Y   L   P   F   E   V
    290                 295                 300

CTG GGA ACA TCA GGC TAT GAT TAC TAT CAT GTG GAT GAC CTA GAA AAT    1377
 L   G   T   S   G   Y   D   Y   Y   H   V   D   D   L   E   N
305                 310                 315                 320

TTG GCA AAA TGT CAT GAG CAC TTA ATG CAA TAT GGG AAA GGC AAA TCA    1425
 L   A   K   C   H   E   H   L   M   Q   Y   G   K   G   K   S
            325                 330                 335

TGT TAT TAT AGG TTC CTG ACT AAG GGG CAA CAG TGG CTT ATT TGG CTT CAG    1473
 C   Y   Y   R   F   L   T   K   G   Q   Q   W   I   W   L   Q
            340                 345                 350
```

Fig. 14E

```
ACT CAT TAT TAT ATC ACT TAC CAT CAG TGG AAT TCA AGG CCA GAG TTT   1521
 T   H   Y   Y   I   T   Y   H   Q   W   N   S   R   P   E   F
             355                 360                 365

ATT GTT TGT ACT CAC ACT GTA AGT TAT GCA GAA GTT AGG GCT GAA        1569
 I   V   C   T   H   T   V   S   Y   A   E   V   R   A   E
     370                 375                 380

AGA CGA GAA CTT GGC ATT GAA GAG TCT CTT CCT AAT CGT ATA AAC ACA GCT GCT  1617
 R   R   E   L   G   I   E   E   S   L   P   N   R   I   N   T   A   A
 385                 390                 395                 400

GAC AAA AGC CAA GAT TCT GGG TCA GAT AAT CAC AGC CCA ACC CCT TCT GCC    1665
 D   K   S   Q   D   S   G   S   D   N   H   S   P   T   P   S   A
             405                 410                 415

CTC AAG GAA GCA TTG GAA AGG TTT GAT CAC AGC TCT CAC ACG GCC GTC TCA GAC CCT  1713
 L   K   E   A   L   E   R   F   D   H   S   S   H   T   A   V   S   D   P
     420                 425                 430                 445

TCT TCT CGG AGT TCA AGA AAA TCA AGC
 S   S   R   S   S   R   K   S   S
 435                 440
```

Fig. 14F

```
TCC TCA ACA CCA ACC AAG ATC CCG ACG AGC ACT CCA CCC AGG    1809
 S   S   T   P   T   K   I   P   T   S   T   P   P   R
450                 455                 460

CAG CAT TTA CCA GCT CAT GAG AAG ATG GTG CAA AGA AGG TCA TCA TTT    1857
 Q   H   L   P   A   H   E   K   M   V   Q   R   R   S   S   F
465                 470                 475                 480

AGT AGT CAG TCC ATA AAT TCC CAG TCT GTT GGT TCA TCA TTA ACA CAG    1905
 S   S   Q   S   I   N   S   Q   S   V   G   S   S   L   T   Q
        485                 490                 495

CCA GTG ATG TCT CAA GCT ACA AAT TTA CCA ATT CCA CAA GGC ATG CTG AAA GAC    1953
 P   V   M   S   Q   A   T   N   L   P   I   P   Q   G   M   L   K   D
500                 505                 510

CAG TTT CAG TTT TCA GCT CAA TTA GGA GCC ATG CAA CAT CTG    2001
 Q   F   Q   F   S   A   Q   L   G   A   M   Q   H   L
515                 520                 525

CAA TTG GAA CAA CGG ACA CGC ATG ATA GAA GCA AAT ATT CAT CGG CAA    2049
 Q   L   E   Q   R   T   R   M   I   E   A   N   I   H   R   Q
530                 535                 540
```

Fig. 14G

```
CAA GAA GAA CTA AGA AAA ATT CAA GAA CAA CTT CAG ATG GTC CAT GGT    2097
 Q   E   E   L   R   K   I   Q   E   Q   L   Q   M   V   H   G
545                 550                 555                 560

CAG GGG CTG CAG ATG TTT TTG CAA CAA TCA AAT CCT GGG TTG AAT TTT    2145
 Q   G   L   Q   M   F   L   Q   Q   S   N   P   G   L   N   F
                565                 570                 575

GGT TCC GTT CAA CTT TCT TCT GGA AAT TCA TCT AAC ATC CAG CAA CTT    2193
 G   S   V   Q   L   S   S   G   N   S   S   N   I   Q   Q   L
            580                 585                 590

GCA CCT ATA AAT ATG CAA GGC CAC ATT GGC ACA ACT CAG CAC ATT CAA    2241
 A   P   I   N   M   Q   G   H   I   G   T   T   Q   H   I   Q
        595                 600                 605

AGT GGA ATG AAT ACT GGA CAC ATC ACT CAG AGT CAA CAA ATG ATA CAA    2289
 S   G   M   N   T   G   H   I   T   Q   S   Q   Q   M   I   Q
    610                 615                 620

CAA CAG ACT TTA CAG AGT ACA TCA ACT CAG AGT CAA CAA AAT GTA CTG    2337
 Q   Q   T   L   Q   S   T   S   T   Q   S   Q   Q   N   V   L
625                 630                 635                 640
```

Fig. 14H

```
AGT GGG CAC AGT CAG CAA ACA TCT CTA CCC AGT CAG ACA CAG AGC ACT  2385
 S   G   H   S   Q   Q   T   S   L   P   S   Q   T   Q   S   T
                645                 650                 655

CTT ACA GCC CCA CTG TAT AAC ACT ATG GTG ATT TCT CAG CCT GCA GCC  2433
 L   T   A   P   L   Y   N   T   M   V   I   S   Q   P   A   A
                660                 665                 670

GGA AGC ATG GTC CAG ATT CCA TCT ATG CCA CAA AAC AGC ACC CAG       2481
 G   S   M   V   Q   I   P   S   M   P   Q   N   S   T   Q
                675                 680                 685

AGT GCT GCA GTA ACT ACA TTC ACT CAG GAC AGG CAG ATA TTT TCT       2529
 S   A   A   V   T   T   F   T   Q   D   R   Q   I   F   S
                690                 695                 700

CAA GGT CAA CAA CTT GTG ACC AAA TTA GTG ACT GCT CCT GTA GCT TGT   2577
 Q   G   Q   Q   L   V   T   K   L   V   T   A   P   V   A   C
                705                 710                 715                 720

GGG GCA GTC ATG GTA CCT AGT ACT ATG CTT ATG GGC CAG GTG ACT       2625
 G   A   V   M   V   P   S   T   M   L   M   G   Q   V   T
                725                 730                 735
```

Fig. 14I

```
GCA TAT CCT ACT TTT GCT ACA CAA CAG CAA CAG TCA CAG ACA TTG TCA   2673
 A   Y   P   T   F   A   T   Q   Q   Q   Q   S   Q   T   L   S
                740             745             750

GTA ACG CAG CAG CAG CAG CAG AGC TCC CAG CAG CAG GAG CAG CTC ACT   2721
 V   T   Q   Q   Q   Q   Q   S   S   Q   Q   Q   E   Q   L   T
            755             760             765

TCA GTT CAG CAA CCA TCT CAG CAG CAG GCT CAG CTG ACC CAG CCA CCG   2769
 S   V   Q   Q   P   S   Q   Q   Q   A   Q   L   T   Q   P   P
        770             775             780

TTT TTA CAG ACT TCT AGG TTG CTC CAT GGG AAT CCC TCA ACT CAA CTC   2817
 F   L   Q   T   S   R   L   L   H   G   N   P   S   T   Q   L
785             790             795             800

ATT CTC TCT GCT GCA TTT CCT CTA CAA CAG AGC ACC TTC CCT CAG TCA   2865
 I   L   S   A   A   F   P   L   Q   Q   S   T   F   P   Q   S
            805             810             815

CAT CAC CAG CAA CAT CAG TCT CAG CAG CAA CAG CAA CTC AGC CGG CAC   2913
 H   H   Q   Q   H   Q   S   Q   Q   Q   Q   Q   L   S   R   H
        820             825             830
```

Fig. 14J

```
AGG ACT GAC AGC TTG CCC GAC CCT TCC AAG GTT CAA CCA CAG T      2956
 R   T   D   S   L   P   D   P   S   K   V   Q   P   Q
            835                 840                 845

AGCACACGTG CTTCCTCTCT TGACATCAAG GGAGGAAGGG GATGCCCCAT TAAGAGTTAC   3016
TCAGATGACC TGAGGAAAGG AGGGAAAGTT CCAGCAGTTT CATGAGATGC AGTATTGAGT   3076
GTTCTAGTTC CTGGAATTAG TTGGCAGAGA AAATGCTGCC TAGTGCTACA GATGTACATT   3136
AAATACCAGC CAGCAGGAGG TGATCATAGG GGCACAGCCA GTTCTGACAG TGTTTTAGGT   3196
GCCTGGATAT TTTTTGATGG AAAAAGAATA TATTGCCAAA CTCAGCTATG              3256
AAATGACCTC CAGGGAATCA GAAAGGCACT AATGATGTTA GTAACTTTTA GTGGTTCTGT   3316
GCCTCTTATC AAGTGTTACA GAGGACATAC CACTGCCATG TCAGGGGTTT GCTTACAGTG   3376
ATGCCATGAA GACAGTCCAG AGCGACCCCC TCCCCCAACC CCTCTCCCTT              3436
TTCAGATAAT GATGGAACAG TAGACTTGGT CAGAATGTTG TGTGGGTTCA AATTCTCTAT   3496
GTACAGATGA TGTAAAAATA TGTATATGTC TAGATAAAAG GAGAGAAAGC              3546
```

Fig. 15A

```
hC  MLFTVSCSKM  SSIVDRDDSS  IFDGLVEEDD  KDKAKRVSRN  KSEKKRRDQF  NVLIKELGSM   60
mC  MVFTVSCSKM  SSIVDRDDSS  IFDGLVEEDD  KDKAKRVSRN  KSEKKRRDQF  NVLIKELGSM   60
CN  M.FTVSCSKM  SSIVDRDDSS  IFDGLVEEDD  KDKAKRVSRN  KSEKKRRDQF  NVLIKELGSM   60 hC  LPGNARKMDK  STVLQKSIDF  LRKHKEITAQ  SDASEIRQDW  KPTFLSNEEF  TQLMLEALDG  120
mC  LPGNARKMDK  STVLQKSIDF  LRKHKETTAQ  SDASEIRQDW  KPTFLSNEEF  TQLMLEALDG  120
CN  LPGNARKMDK  STVLQKSIDF  LRKHKE.TAQ  SDASEIRQDW  KPTFLSNEEF  TQLMLEALDG  120 hC  FFLAIMTDGS  IIYVSESVTS  LLEHLPSDLV  DQSIFNFIPE  GEHSEVYKIL  STHLLESDSL  180
mC  FFLAIMTDGS  IIYVSESVTS  LLEHLPSDLV  DQSIFNFIPE  GEHSEVYKIL  STHLLESDSL  180
CN  FFLAIMTDGS  IIYVSESVTS  LLEHLPSDLV  DQSIFNFIPE  GEHSEVYKIL  STHLLESDSL  180 hC  TPEYLKSKNQ  LEFCCHMLRG  TIDPKEPSTY  EYVKFIGNFK  SLNSVSSSAH  NGFEGTIQRT  240
mC  TPEYLKSKNQ  LEFCCHMLRG  TIDPKEPSTY  EYVRFIGNFK  SLTSVSTSTH  NGFEGTIQRT  240
CN  TPEYLKSKNQ  LEFCCHMLRG  TIDPKEPSTY  EYV.FIGNFK  SL.SVS.S.H  NGFEGTIQRT  240 hC  HRPSYEDRVC  FVATVRLATP  QFIKEMCTVE  EPNEEFTSRH  SLEWKFLFLD  HRAPPIIGYL  300
mC  HRPSYEDRVC  FVATVRLATP  QFIKEMCTVE  EPNEEFTSRH  SLEWKFLFLD  HRAPPIIGYL  300
CN  HRPSYEDRVC  FVATVRLATP  QFIKEMCTVE  EPNEEFTSRH  SLEWKFLFLD  HRAPPIIGYL  300 hC  PFEVLGTSGY  DYYHVDDLEN  LAKCHEHLMQ  YGKGKSCYYR  FLTKGQQWIW  LQTHYYITYH  360
mC  PFEVLGTSGY  DYYHVDDLEN  LAKCHEHLMQ  YGKGKSCYYR  FLTKGQQWIW  LQTHYYITYH  360
CN  PFEVLGTSGY  DYYHVDDLEN  LAKCHEHLMQ  YGKGKSCYYR  FLTKGQQWIW  LQTHYYITYH  360
```

Fig. 15B

```
hC  QWNSRPEFIV CTHTVVSYAE VRAERRRELG IEEESLPETAA DKSQDSGSDN RINTVSLKEA  420
mC  QWNSRPEFIV CTHTVVSYAE VRAERRRELG IEEESLPETAA DKSQDSGSDN RINTVSLKEA  420
CN  QWNSRPEFIV CTHTVVSYAE VRAERRRELG IEEESLPETAA DKSQDSGSDN RINTVSLKEA  420 hC  LERFDHSPTP SASSRSSRKS SHTAVSDPSS TPTKIPTDTS TPPRQHLPAH EKMVQRRSSF  480
mC  LERFDHSPTP SASSRSSRKS SHTAVSDPSS TPTKIPTDTS TPPRQHLPAH EKMTQRRSSF  480
CN  LERFDHSPTP SASSRSSRKS SHTAVSDPSS TPTKIPTDTS TPPRQHLPAH EKM.QRRSSF  480 hC  SSQSINSQSV GSSLTQPVMS QATNLPIPQG MSQFQFSAQL GAMQHLKDQL EQRTRMIEAN  540
mC  SSQSINSQSV GPSLTQPAMS QAANLPIPQG MSQFQFSAQL GAMQHLKDQL EQRTRMIEAN  540
CN  SSQSINSQSV G.SLTQP.MS QA.NLPIPQG MSQFQFSAQL GAMQHLKDQL EQRTRMIEAN  540 hC  IHRQQEELRK IQEQLQMVHG QGLQMFLQQS NPGLNFGSVQ LSSGNSSNIQ QLAPINMQGQ  600
mC  IHRQQEELRK IQEQLQMVHG QGLQMFLQQS NPGLNFGSVQ LSSGNS-NIQ QLTPVNMQGQ  599
CN  IHRQQEELRK IQEQLQMVHG QGLQMFLQQS NPGLNFGSVQ LSSGNS.NIQ QL.P.NMQGQ  600 hC  VVPTNQIQSG MNTGHIGTTQ HMIQQQTLQS TSTQSQQNVL -SGHSQQTSL PSQTQSTLTA  659
mC  VVPANQVQSG ---HISTGQ HMIQQQTLQS TSTQQSQQSV MSGHSQQTSL PSQTPSTLTA  655
CN  VVP.NQ.QSG ....HI.T.Q HMIQQQTLQS TSTQ..Q.... .SGHSQQTSL PSQT.STLTA  660 hC  PLYNTMVISQ PAAGSMVQIP SSMPQNSTQS AAVTTFTQDR QIRFSQGQQL VTKLVTAPVA  719
mC  PLYNTMVISQ PAAGSMVQIP SSMPQNSTQS ATVTTFTQDR QIRFSQGQQL VTKLVTAPVA  715
CN  PLYNTMVISQ PAAGSMVQIP SSMPQNSTQS A.VTTFTQDR QIRFSQGQQL VTKLVTAPVA  720
```

Fig. 15C

```
hC  CGAVMVPSTM LMGQVVTAYP TFATQQQQSQ TLSVTQQQQQ QSSQEQQ--- -------           766
mC  CGAVMVPSTM LMGQVVTAYP TFATQQQQAQ TLSVTQQQQQ QQQQPPQQQQ QQQQSSQEQQ        775
CN  CGAVMVPSTM LMGQVVTAYP TFATQQQQ.Q TLSVTQQQQQ Q..Q...Q.. ......           780 hC  LTSVQQPSQA QLTQPPQQFL QTSRLLHGNP STQLILSAAF PLQQSTFPQS HHQQHQSQQQ        826
mC  LPSVQQPAQA QLGQPPQQFL QTSRLLHGNP STQLILSAAF PLQQSTFPPS HHQQHQPQQQ        835
CN  L.SVQQP.QA QL.QPPQQFL QTSRLLHGNP STQLILSAAF PLQQSTFP.S HHQQHQ.QQQ        840 hC  QQLSRHRTDS LPDPSKVQPQ                                                   846
mC  QQLPRHRTDS LTDPSKVQPQ                                                   855
CN  QQL.RHRTDS L.DPSKVQPQ                                                   860
```

Fig. 16A

```
hCO  ATGTGTTTA  CCGTAAGCTG  TAGTAAAAATG  AGCTCGATTG  TTGACAGAGA  TGACAGTAGT   60
mCO  ATGGTGTTTA  CCGTAAGCTG  TAGTAAAAATG  AGCTCAATTG  TTGACAGAGA  TGACAGTAGT   60
Con  ATGKTGTTTA  CCGTAAGCTG  TAGTAAAAATG  AGCTCRATTG  TTGACAGAGA  TGACAGTAGT   60 hCO  ATTTTTGATG  GGTTGGTGGA  AGAAGATGAC  AAGGACAAAG  CGAAAAGAGT  ATCTAGAAAC  120
mCO  ATTTTTGATG  GATTGGTGGA  AGAAGATGAC  AAGGACAAAG  CAAAAAGAGT  ATCTAGAAAC  120
Con  ATTTTTGATG  GRTTGGTGGA  AGAAGATGAC  AAGGACAAAG  CRAAAAGAGT  ATCTAGAAAC  120 hCO  AAATCTGAAA  AGAAACGTAG  AGATCAATTT  AATGTTCTCA  TTAAAGAACT  GGGATCCATG  180
mCO  AAATCAGAAA  AGAAACGTAG  AGATCAGTTC  AATGTCCTCA  TTAAGGAGCT  GGGGTCTATG  180
Con  AAATCWGAAA  AGAAACGTAG  AGATCARTTY  AATGTYCTCA  TTAARGARCT  GGGRTCYATG  180 hCO  CTTCCTGGTA  ATGCTAGAAA  GATGGACAAA  TCTACTGTTC  TGCAGAAAAG  CATTGATTTT  240
mCO  CTTCCTGGTA  ACGCGAGAAA  GATGGACAAG  TCTACTGTTC  TACAGAAGAG  CATTGATTTT  240
Con  CTTCCTGGTA  AYGCKAGAAA  GATGGACAAR  TCTACTGTTC  TRCAGAARAG  CATTGATTTT  240 hCO  TTACGAAAAC  ATAAAGAAAT  CACTGCACAG  TCAGATGCTA  GTGAAATTCG  ACAGGACTGG  300
mCO  TTGCGCAAAC  ATAAAGAGAC  CACTGCACAG  TCAGATGCTA  GTGAGATTCG  ACAGGACTGG  300
Con  TTRCGMAAAC  ATAAAGARAY  CACTGCACAG  TCAGATGCTA  GTGARATTCG  ACAGGACTGG  300 hCO  AAACCTACAT  TCCTTAGTAA  TGAAGAGTTT  ACACAATTAA  TGTTAGAGGC  TCTTGATGGT  360
mCO  AAACCCACAT  TCCTTAGTAA  TGAAGAGTTT  ACACAGTTAA  TGTTAGAGGC  TCTTGATGGT  360
Con  AAACCYACAT  TCCTTAGTAA  TGAAGAGTTT  ACACARTTAA  TGTTAGAGGC  TCTTGATGGT  360
```

Fig. 16B

```
hCO  TTTTTTTAG  CAATCATGAC  AGATGGAAGC  ATAATATATG  TGTCTGAGAG  TGTAACTTCA  420
mCO  TTTTTTTAG  CGATCATGAC  AGATGGAAGT  ATAATATATG  TATCTGAGAG  TGTAACTTCG  420
Con  TTTTTTTAG  CRATCATGAC  AGATGGAAGY  ATAATATATG  TRTCTGAGAG  TGTAACTTCR  420 hCO  TTACTTGAAC  ATTTACCATC  TGATCTTGTG  GATCAAAGTA  TATTTAATTT  TATCCCAGAA  480
mCO  TTACTTGAAC  ATTTACCATC  TGATCTTGTG  GATCAAAGTA  TATTTAATTT  TATCCCAGAG  480
Con  TTACTTGAAC  ATTTACCATC  TGATCTTGTG  GATCAAAGTA  TATTTAATTT  TATCCCAGAR  480 hCO  GGGGAACATT  CAGAGGTTTA  TAAAATACTC  TCTACTCATC  TGATTCATTA  540
mCO  GGAGAACATT  CAGAGGTTTA  TAAGATACTC  TCTACTCATC  TGACTCATTA  540
Con  GGRGAACATT  CAGAGGTTTA  TAARATACTC  TCTACTCATC  TGAYTCATTA  540 hCO  ACCCCAGAAT  ATTTAAAAAT  AAAAAAATCAG  TTAGAATTCT  GTTGTCACAT  GCTGCGAGGA  600
mCO  ACCCCTGAGT  ACTTAAAAAT  AAAAAAATCAG  TTAGAATTCT  GTTGTCACAT  GCTTCGAGGA  600
Con  ACCCCWGART  AYTTAAAAAT  AAAAAAATCAG  TTAGAATTCT  GTTGTCACAT  GCTKCGAGGA  600 hCO  ACAATAGACC  CAAAGGAGCC  ATCTACCTAT  GAATATGTAA  AATTTATAGG  AAATTTCAAA  660
mCO  ACAATAGACC  CAAAGGAGCC  ATCCACCTAT  GAATATGTGA  GATTTATAGG  AAATTTTAAA  660
Con  ACAATAGACC  CAAAGGAGCC  ATCYACCTAT  GAATATGTRA  RATTTATAGG  AAATTTYAAA  660 hCO  TCTTTAAACA  GTGTATCCTC  TTCAGCACAC  AATGGTTTTG  AAGGAACTAT  ACAACGCACA  720
mCO  TCTTTAACCA  GTGTATCAAC  TTCAACACAC  AATGGTTTTG  AAGGAACTAT  ACAACGCACA  720
Con  TCTTTAAMCA  GTGTATCMWC  TTCARCACAC  AATGGTTTTG  AAGGAACTAT  ACAACGCACA  720
```

Fig. 16C

| | | | | | | | |
|---|---|---|---|---|---|---|---|
| hCO | CATAGGCCAT | CTTATGAAGA | TAGAGTTTGT | TTTGTAGCTA | CTGTCAGGTT | AGCTACACCT | 780 |
| mCO | CATAGGCCTT | CTTATGAAGA | TAGAGTTTGT | TTTGTAGCTA | CTGTCAGATT | AGCTACACCT | 780 |
| Con | CATAGGCCWT | CTTATGAAGA | TAGAGTTTGT | TTTGTAGCTA | CTGTCAGRTT | AGCTACACCT | 780 |
| | | | | | | | |
| hCO | CAGTTCATCA | AGGAAATGTG | CACTGTTGAA | GAACCCAATG | AAGAGTTTAC | ATCTAGACAT | 840 |
| mCO | CAGTTCATCA | AGGAAATGTG | TACTGTTGAA | GAACCAAATG | AAGAGTTTAC | ATCTAGACAC | 840 |
| Con | CAGTTCATCA | AGGAAATGTG | TACTGTTGAA | GAACCMAATG | AAGAGTTTAC | ATCTAGACAY | 840 |
| | | | | | | | |
| hCO | AGTTTAGAAT | GGAAGTTTCT | GTTTCTAGAT | CACAGGGCAC | CACCCATAAT | AGGGTATTTG | 900 |
| mCO | AGTTTAGAAT | GGAAGTTTCT | ATTTTTAGAT | CACAGGGCAC | CACCAATAAT | AGGCTATTTG | 900 |
| Con | AGTTTAGAAT | GGAAGTTTCT | RTTTYTAGAT | CACAGGGCAC | CACCMATAAT | AGGSTATTTG | 900 |
| | | | | | | | |
| hCO | CCATTTGAAG | TTCTGGGAAC | ATCAGGCTAT | GATTACTATC | ATGTGGATGA | CCTAGAAAAT | 960 |
| mCO | CCATTTGAAG | TCTTGGGAAC | ATCAGGCTAT | GATTACTATC | ATGTGGATGA | CCTAGAAAAT | 960 |
| Con | CCATTTGAAG | TYYTGGGAAC | ATCAGGCTAT | GATTACTATC | ATGTGGATGA | CCTAGAAAAT | 960 |
| | | | | | | | |
| hCO | TGGCAAAAT | GTCATGAGCA | CTTAATGCAA | TATGGGAAAG | GCAAATCATG | TTATTATAGG | 1020 |
| mCO | CTGGCAAAAT | GTCACGAGCA | CTTAATGCAA | TATGGAAAAG | GCAAATCGTG | TTACTATAGA | 1020 |
| Con | YTGGCAAAAT | GTCAYGAGCA | CTTAATGCAA | TATGGRAAAG | GCAAATCRTG | TTAYTATAGR | 1020 |
| | | | | | | | |
| hCO | TTCCTGACTA | AGGGGCAACA | GTGGATTTGG | CTTCAGACTC | ATTATTATAT | CACTTACCAT | 1080 |
| mCO | TTCCTGACCA | AAGGCCAGCA | GTGGATATGG | CTTCAGACTC | ATTATTATAT | TACTTACCAT | 1080 |
| Con | TTCCTGACYA | ARGGSCARCA | GTGGATWTGG | CTTCAGACTC | ATTATTATAT | YACTTACCAT | 1080 |

Fig. 16D

```
hCO   CAGTGGAATT CAAGGCCAGA GTTTATTGTT TGTACTCACA CTGTAGTAAG TTATGCAGAA   1140
mCO   CAGTGGAATT CAAGGCCAGA GTTCATTGTT TGTACTCACA CTGTAGTAAG TTATGCAGAA   1140
Con   CAGTGGAATT CAAGGCCAGA GTTYATTGTT TGTACTCACA CTGTAGTAAG TTATGCAGAA   1140 hCO   GTTAGGGCTG AAAGACGACG AGAACTTGGC ATTGAAGAGT CTCTTCCTGA GACAGCTGCT   1200
mCO   GTTAGGGCTG AAAGACGGCG AGAACTTGGC ATTGAAGAGT CTCTTCCTGA GACAGCTGCT   1200
Con   GTTAGGGCTG AAAGACGRCG AGAACTTGGC ATTGAAGAGT CTCTTCCTGA GACAGCTGCT   1200 hCO   GACAAAAGCC AAGATTCTGG GTCAGATAAT CGTATAAACA CAGTCAGTCT CAAGGAAGCA   1260
mCO   GACAAAAGCC AAGATTCTGG GTCTGACAAT CGTATCAACA CAGTGAGTCT CAAGGAAGCA   1260
Con   GACAAAAGCC AAGATTCTGG GTCWGAYAAT CGTATMAACA CAGTSAGTCT CAAGGAAGCA   1260 hCO   TTGGAAAGGT TTGATCACAG CCGTCTCAGA CCCAACCCCT TCTGCCTCTT CTCGGAGTTC   1320
mCO   CTGGAAAGGT TTGATCACAG CAGTCTCAGA CCCAACTCCT TCTGCCTCCT CTAGAAGCTC   1320
Con   YTGGAAAGGT TTGATCACAG CMGTCTCAGA CCCAACYCCT TCTGCCTCYT CTMGRAGYTC   1320 hCO   TCTCACACGG CCGTCTCAGA CCCTTCCTCA ACACCAACCA AGATCCCGAC GGATACGAGC   1380
mCO   TCTCACACCG CAGTCTCAGA CCCTTCCTCC ACACCGACAA AGATCCCTAC TGATACTAGC   1380
Con   TCTCACACSG CMGTCTCAGA CCCTTCCTCM ACACCRACMA AGATCCCKAC KGATACKAGC   1380 hCO   ACTCCACCCA GGCAGCATTT ACCAGCTCAT GAGAAGATGG TGCAAAGAAG GTCATCATTT   1440
mCO   ACTCCTCCCA GACAGCATTT GCCAGCTCAT GAAAAGATGA CACAGCGGAG GTCGTCCTTC   1440
Con   ACTCCWCCCA GRCAGCATTT RCCAGCTCAT GARAAGATGR YRCARMRGAG GTCRTCMTTY   1440
```

Fig. 16E

```
hCO  AGTAGTCAGT CCATAAATTC CCAGTCTGTT GGTTCATCAT TAACACAGCC AGTGATGTCT 1500
mCO  AGCAGTCAGT CCATAAACTC CCAGTCAGTT GGTCCATCAT TAACACAGCC AGCGATGTCT 1500
Con  AGYAGTCAGT CCATAAAYTC CCAGTCWGTT GGTYCATCAT TAACACAGCC AGYGATGTCT 1500 hCO  CAAGCTACAA ATTTACCAAT TCCACACAAGGC ATGTCCCAGT TTCAGTTTTC AGCTCAATTA 1560
mCO  CAAGCTGCAA ATTTACCAAT TCCACACAAGGC ATGTCACAGT TTCAGTTTTC AGCTCAGTTA 1560
Con  CAAGCTRCAA ATTTACCAAT TCCACACAAGGC ATGTCMCAGT TTCAGTTTTC AGCTCARTTA 1560 hCO  GGAGCCATGC AACATCTGAA AGACCAATTG GAACAACGGA CACGCATGAT AGAAGCAAAT 1620
mCO  GGAGCCATGC AGCATCTAAA AGACCAGCTA GAGCAGCGGA CACGGATGAT AGAGGCAAAT 1620
Con  GGAGCCATGC ARCATCTRAA AGACCARYTR GARCARCGGA CACGSATGAT AGARGCAAAT 1620 hCO  ATTCATCGGC AACAAGAAGA ACTAAGAAAA ATTCAAGAAC AACTTCAGAT GGTCCATGGT 1680
mCO  ATTCATCGGC AGCAAGAAGA ACTAAGGAAA ATTCAAGAGC AACTTCAGAT GGTCCATGGT 1680
Con  ATTCATCGGC ARCAAGAAGA ACTAAGRAAA ATTCAAGARC AACTTCAGAT GGTCCATGGT 1680 hCO  CAGGGGCTGC AGATGTTTTT GCAACAATCA AATCCTGGGT TGAATTTTGG TTCCGTTCAA 1740
mCO  CAAGGCTAC AGATGTTTTT GCAGCAATCA AACCCTGGAT TGAATTTTGG TTCTGTTCAA 1740
Con  CARGGGCTRC AGATGTTTTT GCARCAATCA AAYCCTGGRT TGAATTTTGG TTCYGTTCAA 1740 hCO  CTTTCTTCTG GAAATTCATC TAACATCCAG CAACTTGCAC CTATAAATAT GCAAGGCCAA 1800
mCO  CTTTCCTCTG GAAATTC--- TAATATCCAG CAGCTCACAC CTGTAAATAT GCAAGGCCAG 1797
Con  CTTTCYTCTG GAAATTCATC TAAYATCCAG CARCTYRCAC CTRTAAATAT GCAAGGCCAR 1800
```

Fig. 16F

```
hCO  GTTGTTCCTA CTAACCAGAT TCAAAGTGGA ATGAATACTG GACACATTGG CACAACTCAG 1860
mCO  GTTGTCCCTG CTAACCAGGT TCA-----GA --G-----TG GACATATCAG CACAGGCCAG 1845
Con  GTTGTYCCTR CTAACCAGRT TCAAAGTGGA ATGAATACTG GACAYATYRG CACARSYCAG 1860 hCO  CACATGATAC AACAACAGAC TTTACAGAGT ACATCAACTC AG----AGTCA ACAAAATGTA 1917
mCO  CACATGATAC AGCAACAGAC TTTACAAAGT ACATCAACTC AGCAGAGTCA ACAGAGTGTA 1905
Con  CACATGATAC ARCAACAGAC TTTACARAGT ACATCAACTC AGCAGAGTCA ACARARTGTA 1920 hCO  CTGAGTGGGC ACAGTCAGCA AACATCTCTA CCCAGTCAGA CACAGAGCAC TCTTACAGCC 1977
mCO  ATGAGTGGAC ACAGTCAGCA GACGTCTCTT CCAAGTCAGA CACCGAGCAC TCTCACAGCC 1965
Con  MTGAGTGGRC ACAGTCAGCA RACRTCTCTW CCMAGTCAGA CACMGAGCAC TCTYACAGCC 1980 hCO  CCACTGTATA ACACTATGGT GATTTCTCAG CCTGCAGCCG GAAGCATGGT CCAGATTCCA 2037
mCO  CCACTGTACA ATACGATGGT GATTTCCCAG CCTGCAGCTG GGAGCATGGT CCAGATTCCA 2025
Con  CCACTGTAYA AYACKATGGT GATTTCYCAG CCTGCAGCYG GRAGCATGGT CCAGATTCCA 2040 hCO  TCTAGTATGC CACAAAACAG CACCCAGAGT GCTGCAGTAA CTACATTCAC TCAGGACAGG 2097
mCO  TCCAGTATGC CACAGAACAG TACCCAGAGT GCTACAGTCA CTACGTTCAC TCAGGACAGA 2085
Con  TCYAGTATGC CACARAACAG YACCCAGAGT GCTRCAGTMA CTACRTTCAC TCAGGACAGR 2100 hCO  CAGATAAGAT TTTCTCAAGG TCAACAACTT GTGACCAAAT TAGTGACTGC TCCTGTAGCT 2157
mCO  CAGATAAGAT TTTCTCAAGG TCAGCAACTT GTGACCAAAT TAGTGACTGC TCCTGTAGCT 2145
Con  CAGATAAGAT TTTCTCAAGG TCARCAACTT GTGACCAAAT TAGTGACTGC TCCTGTAGCT 2160
```

Fig. 16G

```
hCO  TGTGGGGCAG  TCATGGTACC  TAGTACTATG  CTTATGGGCC  AGGTGGTGAC  TGCATATCCT  2217
mCO  TGTGGGGCCG  TCATGGTACC  AAGTACCATG  CTTATGGGTC  AGGTGGTGAC  TGCCTATCCT  2205
Con  TGTGGGGCMG  TCATGGTACC  WAGTACYATG  CTTATGGGYC  AGGTGGTGAC  TGCMTATCCT  2220 hCO  ACTTTTGCTA  CACAACAGCA  ACAGTCACAG  ACATTGTCAG  TAAC------  GCAGCAGCAG  2271
mCO  ACCTTCGCCA  CACAACAGCA  GCAGGCACAG  ACATTATCGG  TAACACAACA  GCAGCAGCAG  2265
Con  ACYTTYGCYA  CACAACAGCA  RCAGKCACAG  ACATTRTCRG  TAACACAACA  GCAGCAGCAG  2280 hCO  CAGC------  ----------  ----------  -------AGC  AGAGCTCCCA  GGAGCAGCAG  2298
mCO  CAGCAGCAGC  AGCCACCACA  CAACAACAGC  CAACAACAGC  AGAGTTCCCA  GGAACAGCAG  2325
Con  CAGCAGCAGC  AGCCACCACA  CAACAACAGC  CAACAACAGC  AGAGYTCCCA  GGARCAGCAG  2340 hCO  CTCACTTCAG  TTCAGCAACC  ATCTCAGGCT  CAGCTGACCC  AGCCACCCGCA  ACAATTTTTA  2358
mCO  CTTCCTTCAG  TTCAGCAGCC  AGCTCAGGCC  CAGCTGGGCC  AGCCACCACA  GCAGTTCTTA  2385
Con  CTYMCTTCAG  TTCAGCARCC  AKCTCAGGCY  CAGCTGRSCC  AGCCACCRCA  RCARTTYTTA  2400 hCO  CAGACTTCTA  GGTTGCTCCA  TGGGAATCCC  TCAACTCAAC  TCATTCTCTC  TGCTGCATTT  2418
mCO  CAGACATCTA  GGTTGCTCCA  CGGGAATCCT  TCGACACAGC  TCATCCCTCTC TGCTGCCTTT  2445
Con  CAGACWTCTA  GGTTGCTCCA  YGGGAATCCY  TCRACWCARC  TCATYCTCTC  TGCTGCMTTT  2460 hCO  CCCTCTACAAC AGAGCACTT  CCCTCAGTCA  CATCACCAGC  AACATCAGTC  TCAGCAACAG  2478
mCO  CCACTACAAC  AGAGCACTT   CCCTCCTTCG  CACCACCAGC  AACACCAGCC  TCAGCAGCAA  2505
Con  CCWCTACAAC  AGAGCACYTT  CCCTCMKTCR  CAYCACCAGC  AACAYCAGYC  TCAGCARCAR  2520
```

Fig. 16H

```
hCO  CAGCAACTCA  GCCGGCACAG  GACTGACAGC  TTGCCCGACC  CTTCCAAGGT  TCAACCACAG  2538
mCO  CAGCAGCTTC  CTCGGCACAG  GACTGACAGC  CTGACTGACC  CTTCCAAGGT  CCAGCCACAG  2565
Con  CAGCARCTYM  SYCGGCACAG  GACTGACAGC  YTGMCYGACC  CTTCCAAGGT  YCARCCACAG  2580
```

CLOCK GENE AND GENE PRODUCT

CROSS REFERENCE TO RELATED APPLICATIONS

This application is a divisional of U.S. application Ser. No. 08/885,291, filed on Jun. 30, 1997, now U.S. Pat. No. 6,057,125.

TECHNICAL FIELD OF THE INVENTION

The field of the present invention is the circadian clock of mammals. More particularly, the present invention relates to mammalian genes and gene products that regulate aspects of the circadian rhythm in mammals and those processes controlled by the circadian rhythm.

BACKGROUND OF THE INVENTION

Circadian rhythms are a fundamental property of all eukaryotic and some prokaryotic organisms (Takahashi 1995). The underlying molecular mechanism appears similar among living systems, is cell autonomous and involves periodic macromolecular synthesis. Alterations in circadian rhythms are involved in sleep disorders such as "delayed sleep phase syndrome" which may be an alteration in the circadian period (lengthening) and the entrainment system. There is also evidence for circadian rhythm abnormalities in affective disorders. The most consistent feature of circadian rhythms observed in depressed patients is that a variety of physiological events occur earlier than normal (usually referred to as a "phase advance"). A shortened REM latency after sleep onset, which can be the manifestation of a change in the circadian coupling or organization of rhythms, appears to be a prominent characteristic of depression.

Further, a number of diagnostic tests depend on the time of day at which the test is performed. These include the dexamethasone suppression test for depression, intraocular pressure measurements for glaucoma, and plasma cortisol concentration for Addison's disease and Cushing's syndrome. In addition, a number of clinical treatments (such as chemotherapy or alleviation of hypertension) can be optimized through the delivery of therapeutic agents at the appropriate time of day. Circadian rhythmicity appears to be deeply embedded in most aspects of the biology of organisms—indeed it is a central feature of their organization. It seems unlikely that complete understanding of most regulatory processes can be achieved without an appreciation of their circadian dimensions.

Clock genes have been described in other model systems, most notably in Drosophila and Neurospora. Three known clock genes have been characterized at the molecular and functional level. These are the period (per) and timeless (tim) genes in Drosophila, and the frequency (frq) gene in Neurospora. This work is known to the art and is described in review papers by J. S. Takahashi, *Annual Review of Neuroscience* 18:531–553, 1995; and by J. C. Dunlap, *Annual Review of Genetics* 30:579–601, 1996. None of these three clock genes have been shown to possess a protein motif known to allow these proteins to bind DNA, rather it appears that in the case of PERIOD and TIMELESS, these proteins must interact with unidentified DNA-binding transcription factors.

The genetic approach to circadian rhythms was first described by Ron Konopka and Seymour Benzer (1971) who isolated single-gene mutations that altered circadian periodicity in Drosophila. In a chemical mutagenesis screen of the X chromosome, they found three mutants that either shortened (per$^S$), lengthened (per$^L$) or abolished (per$^0$) circadian rhythms of eclosion and adult locomotor activity. In 1984, two groups at Brandeis and Rockefeller independently cloned per in a series of experiments that showed that germline transformation with DNA could rescue a complex behavioral program (reviewed in Rosbash & Hall 1989). Each of the mutant per alleles is caused by intragenic point mutations that produce missense mutations in per$^S$ and per$^L$, and a nonsense mutation in per$^0$ (Bayfies et al. 1987, Yu et al. 1987). Only recently has the nature of per gene product (PER) become more clear. The Drosophila single-minded protein (SIM) (Nambu et al. 1991), the human aryl hydrocarbon receptor nuclear translocator (ARNT) (Hoffirian et al. 1991), and the aryl hydrocarbon receptor (AHR) (Burbach et al. 1992) all share with PER a domain called PAS, (for PER, ARNT, SIM) (Nambu et al. 1991). The PAS domain contains about 270 amino acids of sequence similarity with two 51-amino acid direct repeats. Recent work shows that the PAS domain can function as a dimerization domain (Huang et al.1993). Because other PAS members are transcriptional regulators and PER can dimerize to them, PER could function as a transcriptional regulator either by working in concert with a partner that carries a DNA-binding domain, or by acting as a dominant-negative regulator by competing with a transcriptional regulator for dimenization or DNA binding. Consistent with this role, PER is predominantly a nuclear protein in the adult central nervous system of Drosophila (Liu et al. 1992).

The expression of PER itself is circadian, and both per mRNA and PER protein abundance levels oscillate. Hardin et al. (1990) showed that per mRNA levels undergo a striking circadian oscillation. The per RNA rhythm persists in constant darkness and the period of the RNA rhythm is ~24 hours in per$^+$ flies and is ~20 hours in per$^S$ flies. The RNA of per$^0$ flies is present at a level ~50% of normal flies, but does not oscillate. In per$^0$ flies that have been rescued by gernline transformation with wild-type per+DNA, both circadian behavior and per RNA cycles are restored. Importantly, in these transformed flies both the exogenousper$^+$ RNA and the endogenous per$^0$ RNA levels oscillate. In addition to a per RNA cycle, the PER protein also shows a circadian rhythm in abundance (Siwicki et al. 1988, Zerr et al. 1990, Edery et al. 1994b). The rhythm in PER protein also depends on per, because per$^O$ flies do not have a protein rhythm and because per mutants alter the PER rhythm (Zerr et al. 1990). Therefore, the circadian expression of per mRNA and protein levels both depend on an active per gene. Because per$^S$ shortens the period of the RNA cycle and because per$^+$ DNA transformation rescues per$^0$ RNA cycling, PER protein expression clearly regulates per RNA cycling. Hardin et al. (1990) propose that feedback of the per gene product regulates its own mRNA levels. Support for such a model has been provided by showing that transient induction of PER from a heat shock promoter/per cDNA transgene in a wild-type background can phase shift circadian activity rhythms in Drosophila (Edery et al. 1994a).

The PER protein rhythm appears to be regulated at both transcriptional and post-transcriptional levels. Hardin et al. (1992) have shown that levels of per precursor RNA cycle in concert with mature per transcripts. In addition, per promoter/CAT fusion gene constructs show that per 5' flanking sequences are sufficient to drive heterologous RNA cycles. These results suggest that circadian fluctuations inper mRNA abundance are controlled at the transcriptional level. In addition to a rhythm in per transcription and PERabundance, PER appears to undergo multiple phosphorylation events as it accumulates each cycle (Edery et al. 1994b). The nature and functional significance of the PER phosphorylation sites, however, are not known at this time. Interestingly, the peak of the per RNA cycle precedes the peak of the PER protein cycle by about 4–6 hours. The reasons for the lag in PER accumulation are not well understood. However, the recent isolation of a second clock mutant, named timeless (tim), has provided significant insight (Sehgal et al. 1994). Tim mutants fail to express circadian rhythms in eclosion and locomotor activity, but more importantly also fail to express circadian rhythms in per mRNA abundance (Sehgal et al. 1994). Furthermore, the nuclear localization of PER is blocked in tim mutants (Vosshall et al. 1994). In 1995, tim was cloned by positional cloning and by interaction with the PAS domain of PER in a yeast two-hybrid screen (Gekakis et al. 1995, Myers et al. 1995). Like PER, TIM is a large protein without any obvious sequence homologies to other proteins. While PER dimerizes to TIM via the PAS domain, TIM is not a member of the PAS family. The expression of tim RNA levels has a striking circadian oscillation which is in phase with the per RNA rhythm. The rhythm in tim RNA levels depends on PER and is abolished in $per^O$ mutants and shortened in $per^S$ mutants. Thus, per and tim express a coordinate circadian rhythm that is interdependent. TIM protein also shows a circadian rhythm with a phase similar to that of PER. Formation of a PER/TIM heterodimer appears to be required for nuclear entry of the complex. In the last year, four different laboratories discovered that light exposure causes a rapid degradation of TIM protein in fies and this action of light can explain how entrainment of the circadian clock in Drosophila occurs (Hunter-Ensor et al. 1996, Lee et al. 1996, Myers et al. 1996, Zeng et al. 1996). Thus, the identification of tim and its functional interaction with per is important because it suggests that elements of a transcription-translation-nuclear transport feedback loop are central elements of the circadian mechanism in Drosophila.

In addition to the Drosophila per and tim genes, progress has been made in elucidating the molecular nature of the Neurospora frequency (frq) gene (Dunlap 1993). Likeper, the frq locus is defined by mutant alleles that either shorten, lengthen or disrupt circadian rhythms (Feldman & Hoyle 1973, Feldman 1982, Dunlap 1993). Cloned in 1989, the sequence of FRQ shows little resemblance to PER (except for a region containing threonine-glycine repeats) (McClung et al. 1989); however, recent molecular work shows striking functional similarities (Aronson et al. 1994). The frq gene expresses a circadian oscillation of mRNA abundance whose period is altered by frq mutations (Aronson et al. 1994). A null allele, $frq^9$, expresses elevated levels of frq transcript and does not show a rhythm in mRNA abundance (Aronson et al. 1994). Interestingly, no level of constitutive expression of $frq^+$ in a null background can rescue overt rhthmicity, which suggests that the circadian rhythm of frq mRNA is a necessary component of the oscillator (Aronson et al. 1994). However, overexpression of a $frq^+$ transgene does negatively autoregulate expression of the endogenous of a frq gene (Aronson et al. 1994). In addition, overexpression of $frg^+$ transgene in a wild-type background blocks overt expression of circadian rhythms (Aronson et al. 1994). The phase of the overt circadian rhythm can be determined by a step reduction in FRQ protein expression (Aronson et al. 1994). Taken together, these experiments show that frq is likely a central component of the Neurospora circadian oscillator and that a negative autoregulatory loop regulating frq transcription forms the basis of the oscillation (Aronson et al. 1994). Recently a direct action of light has been found on frq expression (Crosthwaite et al. 1995). Frq transcription is rapidly induced by light exposure and this effect of light can explain photic entrainment in Neurospora in a simple and direct manner.

Although there are remarkable functional similarities between per and frq, there are also distinct differences. The phases of the mRNA rhythms are different: per peaks at night (Hardin et al. 1990), whereas frq peaks during the day (Aronson et al. 1994). While per overexpression shortens circadian period (Smith & Konopka 1982, Baylies et al. 1987), frq overexpression does not change period but rather abolishes overt rhythmicity (Aronson et al. 1994). The null allele, $per^O$, leads to a constant level of mRNA that is about 50% of the peak level of wild-type levels in Drosophila (Hardin et al. 1990); while in Neurospora, $frq^9$ mRNA levels are significantly elevated relative to wild-type (Aronson et al. 1994). Finally, the action of light on these two systems is opposite: light degrades TIM protein in Drosophila; whereas, it activates the transcription of frq in Neurospora. These differences can be interpreted in at least two ways: 1) the elements of each system are not fully defined and frq and per could define different elements in a conserved pathway within the oscillator feedback loop; or 2) the Drosophila and Neurospora circadian clocks could be functionally analogous rather than phylogenetically homologous. Irrespective of the interpretation, however, it appears likely that a transcription-translation autoregulatory feedback loop may be a common feature of circadian clocks.

Searching for per homologs in mammals has not been very productive despite ten years of effort by a number of laboratories. This is probably due to the relatively low level of sequence similarity of per even among the Drosophilids (Hall 1990). Putative per homologs in mammals have been reported in searches directed against the threonine-glycine (TG) repeat region of PER (Shin et al. 1985, Matsui et al. 1993) and the region of the $per^S$ mutation (Siwicki et al. 1992). However, the TG-repeat clones show no other sequence similarity to PER, and the antigenes detected by antibodies to the $per^S$ region have not been characterized molecularly. New efforts targeted against the PAS dimerization domain (Huang et al. 1993), which is moderately well-conserved among insects (Reppert et al. 1994), using either PCR-based approaches or the yeast two-hybrid system (Fields & Song 1989) could eventually succeed as more bona fide per homologs are cloned in species more closely related to insects. Alternatively, as other Drosophila clock genes are cloned in the future, some should have sequence conservation with mammals as found, for example, with genes regulating pattern formation (Krumlauf 1993) or signal transduction (Zipursky & Rubin 1994). However, at this time no confirmed orthologs of per, tim or frq have been cloned in any vertebrate.

Very little information on the genetics of mammalian circadian rhythms is available. Most work in the field has used quantitative genetic approaches such as comparisons of circadian phenotype among inbred strains of mice and rats, recombinant inbred strain analysis, or selection of natural variants (Hall 1990, Schwartz & Zimmerman 1990, Lynch & Lynch 1992). The most comprehensive analysis of inbred mouse strains was done by Schwartz & Zimmerman (1990) who compared 12 different strains and found that the most extreme strains (C57BL/6J and BALB/cByJ) had a period difference of about one hour in constant darkness. Reciprocal F1 hybrid and recombinant inbred strain analysis provided no evidence of monogenic inheritance of the circadian period. Polygenic inheritance of circadian traits (or more strictly, failure to detect monogenic inheritance) has been the conclusion of every quantitative genetic analysis performed thus far.

A notable exception to the general finding of polygenic control of circadian phenotype is the spontaneous mutation, tau, found in the golden hamster (Ralph & Menaker 1988). Tau is a semidommant, autosomal mutation that shortens circadian period by two hours in heterozygotes and by four hours in homozygotes. Its phenotype is remarkably similar to the Drosophila per$^S$ allele being semidominant, changing period to the same extent, and increasing the amplitude of the phase response curve to light (Ralph & Menaker 1988, Ralph 1991). The tau mutation has been extremely useful for physiological analysis. For example, the circadian pacemaker function of the suprachiasmatic nuclei (SCN) has been definitively demonstrated by transplantation of SCN tissue derived from tau mutant hamsters to establish that the genotype of the donor SCN determines the period of the restored rhythm (Ralph et al. 1990). Furthermore, the effects of having both tau mutant and wild-type SCN tissue in the same animal show that both mutant (~20 h) and wild-type (~24 h) periodicities can be expressed simultaneously suggesting that very little interaction of the oscillators occurs under these conditions (Vogelbaum & Menaker 1992). Additional cellular interactions can also be studied by transplantation of dissociated SCN cells derived from tau mutant and wild-type animals (Ralph & Lehman 1991). Thus, a number of issues that could not be addressed previously have been resolved or approached by the use of the tau mutation.

Unfortunately, not much progress has been made on the genetic and molecular nature of tau. Genetic mapping and molecular cloning of tau remains difficult because of the paucity of genetic information in the golden hamster. Thus far the tau mutation has contributed substantially to physiological analysis, but it will be difficult to elucidate the nature of the tau gene product unless candidate genes become apparent or the hamster is developed as a genetic system.

BRIEF SUMMARY OF THE INVENTION

In one aspect, the present invention provides an isolated and purified polynucleotide comprising a nucleotide sequence consisting essentially of a nucleotide sequence selected from the group consisting of (a)(i) the sequence of SEQ ID NO: 1 from about nucleotide position 491 to about nucleotide position 2953, the sequence of SEQ ID NO: 54 from about nucleotide position 418 to about nucleotide position 2955; (b) sequences that are complementary to the sequences of (a), and (c) sequences that, when expressed, encode a polypeptide comprising an amino acid residue sequence encoded by the sequence of (a). A polynucleotide can be a DNA or RNA molecule. A preferred polynucleotide contains the nucleotide sequence from nucleotide position number 419, 416, 392, 389 or 1 to nucleotide position number 2953 of SEQ ID NO: 1. Another preferred polynucleotide contains the nucleotide sequence from nucleotide position number 490, 438, 435, 421 or 418 to nucleotide position number 2953 of SEQ ID NO:2955.

In another embodiment, a polynucleotide of the present invention is contained in an expression vector. The expression vector preferably further comprises an enhancer-promoter operatively linked to the polynucleotide. In an especially preferred embodiment, the polynucleotide contains a nucleotide sequence as set forth above. The present invention still further provides a host cell transformed with a polynucleotide or expression vector of this invention. Preferably, the host cell is a bacterial cell such as an E. coli.

In another aspect, the present invention provides an oligonucleotide of from about 15 to about 50.nucleotides containing a nucleotide sequence that is identical or complementary to a contiguous sequence of at least 15 nucleotides a polynucleotide of this invention. A preferred oligonucleotide is an antisense oligonucleotide that is complementary to a portion of the polynucleotide of SEQ ID NO: 1.

In another aspect, the present invention provides a polypeptide of mammalian origin. In one embodiment, that polypeptide is an isolated and puried polypeptide of about 855 or less amino acid residues that contains the amino acid residue sequence of at least one of:
a) from residue position 35 to residue position 855 of SEQ ID NO: 2;
b) from residue position 11 to residue position 855 of SEQ ID NO: 2;
c) from residue position 10 to residue position 855 of SEQ ID NO: 2;
d) from residue position 2 to residue position 855 of SEQ ID NO: 2; or
e) from residue position 1 to residue position 855 of SEQ ID NO: 2.

In another embodiment, that polypeptide is an isolated and puried polypeptide of about 846 or less amino acid residues that contains the amino acid residue sequence of at least one of:
a) from residue position 35 to residue position 846 of SEQ ID NO: 55;
b) from residue position 11 to residue position 846 of SEQ ID NO: 55;
c) from residue position 10 to residue position 846 of SEQ ID NO: 55;
d) from residue position 2 to residue position 846 of SEQ ID NO: 55; or
e) from residue position 1 to residue position 846 of SEQ ID NO: 55.

Preferably, a polypeptide of the present invention is a recombinant human polypeptide. In another aspect, the present invention provides a process of making a polypeptide of this invention comprising transforming a host cell with an expression vector that comprises a polynucleotide of the present invention, maintaining the transformed cell for a period of time sufficient for expression of the polypeptide and recovering the polypeptide. Preferably, the host cell is an eukaryotic host cell such as a mammalian cell, or a bacterial cell. An especially preferred host cell is an E. Coli. The present invention also provides a polypeptide made by a process of this invention.

The present invention also provides a pharmaceutical composition comprising a polypeptide, polynucleotide, expression vector or oligonucleotide of this invention and a physiologically acceptable diluent.

In another aspect, the present invention provides uses for the polypetides, polynucleotides and oligonucleotides of the present invention.

BRIEF DESCRIPTION OF THE DRAWINGS

In the drawings which form a portion of the specification:

FIGS. 8A–8M show the complete nucleotide sequence of the Clock gene based upon genomic exon sequences. The nucleotide sequence of the Clock gene is designated SEQ ID NO: 1 and the deduced amino acid residue sequence of the CLOCK polypeptide is designated as SEQ ID NO: 2.

FIGS. 9A–9Z show the nucleotide sequence of individual exons.

FIG. 10 shows the splice acceptor and donor sequences for the exons.

FIG. 11 shows a comparison between the amino acid residue sequence of the CLOCK polypeptide with human NPAS2 and mouse NPAS2.

FIG. 12 shows the amino acid sequence of CLOCK with the bHLH, PAS-A, PAS-B domains of a mutant Clock gene.

FIG. 13 shows the amino acid sequence of a CLOCK variant resulting from an alternate splice.

FIGS. 14A–14J show the nucleotide and deduced amino acid sequence for human CLOCK.

FIGS. 15A–15C show the amino acid residue alignment of the mouse and human CLOCK polypeptides.

FIGS. 16A–16H show the nucleotide alignment of the mouse and human CLOCK genes.

DETAILED DESCRIPTION OF THE INVENTION

I. The Invention

Figure 1:
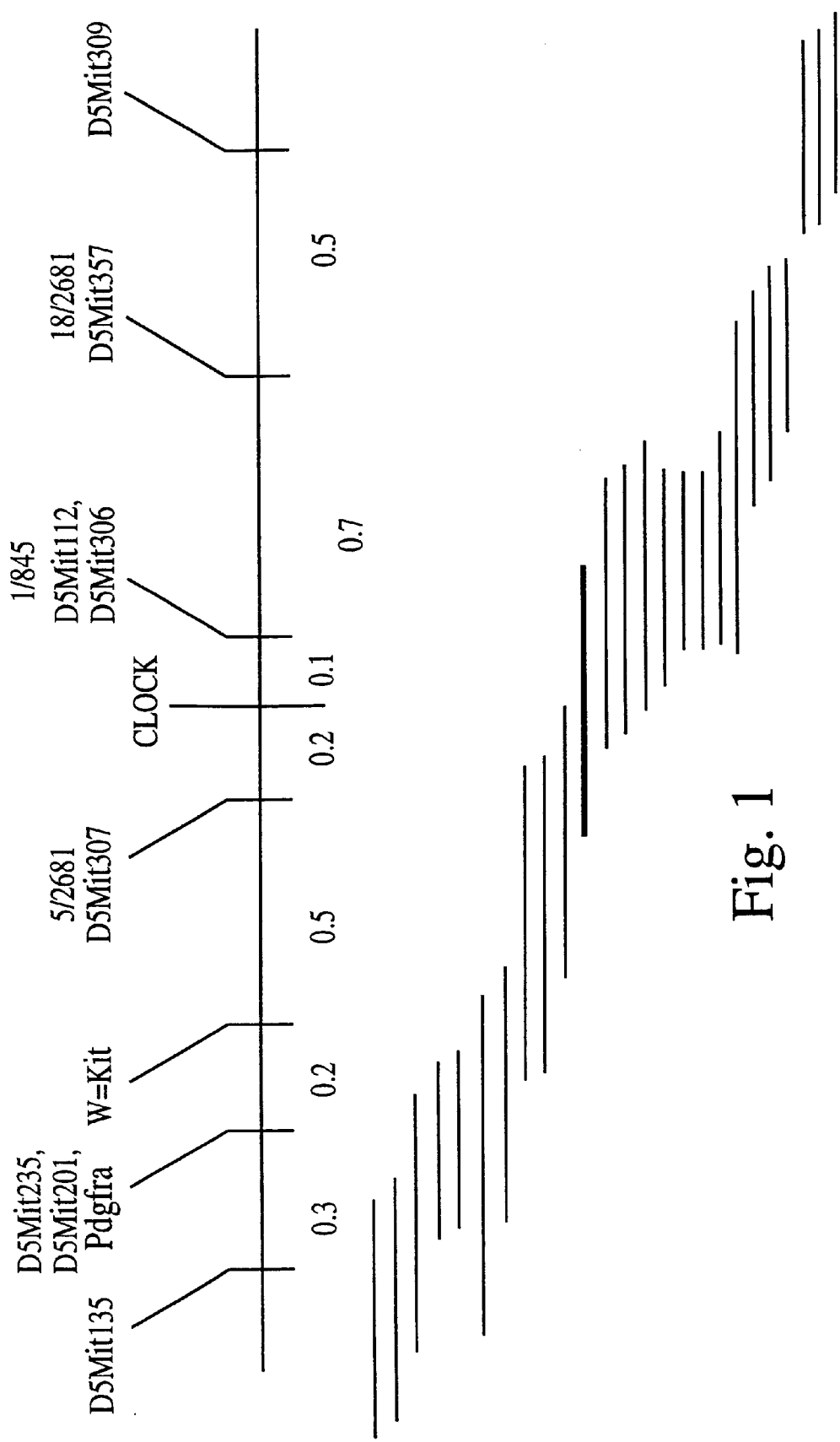
FIG. 1 shows the location of the Clock gene locus in the mouse genome using genetic meiotic mapping.

The present invention provides isolated and purified polypeptide components of the mammalian circadian clock, polynucleotides that encode those polypeptides, expression vectors containing those polynucleotides, host cells transformed with those expression vectors, a process of making the polypeptide components using those polynucleotides and vectors, and processes using those polypeptides and polynucleotides.

II. Clock Polypeptides

In one aspect, the present invention provides a polypeptide that is an integral component of the mammalian circadian clock. The polypeptide serves to regulate various aspects of circadian rhythm in mammals. The polypeptide is referred to herein as the CLOCK polypeptide. The CLOCK polypeptide contains about 855 or less amino acid residues. The amino acid residue sequence of an 855 residue embodiment of CLOCK, which embodiment is the gene product of the Clock gene of the mouse, described hereinafter, is set forth in SEQ ID NO: 2. Another embodiment of a CLOCK polypeptide is set forth in SEQ ID NO: 55. This later embodiment shows the CLOCK polypeptide obtained from humans.

It can be seen from SEQ ID NOs: 2 and 55 that both polypeptides are members member of the basic helix-loop-helix (bHLH)-PAS domain family of proteins. The basic region of the bHLH domain is known to mediate DNA binding. Thus, CLOCK likely interacts directly with DNA. The HLH and PAS domains are further known to be protein dimerization domains and indicate that CLOCK can interact with itself or with other HLH-PAS domain family members. The C-terminal portion of both polypeptides (SEQ ID NO: 2 and 55) can also be seen to have a number of glutamine-rich, proline-rich and serine-rich regions that are characteristic of activation domains of ranscription factors. The CLOCK polypeptide functions as a transcription factor.

There are two methionine (Met) residues in the N-terminal portion of SEQ ID NO: 2 and 55, both of which can serve as the N-terminus of a CLOCK polypeptide. Those two Met residues are located at residue positions 1 and 10 of SEQ ID NO: 2 and 55. Thus, a CLOCK polypeptide of the present invention can contain the amino acid residue sequence of SEQ ID NO: 2 or 55 extending from residue number 1 or residue number 10 to the C-terminus (residue number 855 or 846). As is well known in the art, polypeptides with an N-terminal Met residue can be produced without that Met residue, which Met-minus polypeptide has the same function as the Met-positive embodiment. Thus, a CLOCK polypeptide of the present invention can contain the amino acid residue sequence of SEQ ID NO: 2 or 55 from residue number 2 or residue number 11 to residue number 855 or 846.

As is also well know in the art, proteins having b-HLH dormans can be processed such that the polypeptide starts at the beginning of that b-HLH domain. In SEQ ID NOs: 2 and 55, the b-HLH begins at amino acid residue number 35. Thus, an embodiment of a CLOCK polypeptide of the present invention contains a polypeptide having the amino acid residue sequence of SEQ ID NO: 2 or 55 from residue number 35 to residue number 855 or 846.

As set forth in detail hereinafter, four forms of the CLOCK polypeptide have been identified in the mouse. Those four forms are: (1) SEQ ID NO: 2; (2) residues 1 to 513 and residues 565 to 855 of SEQ ID NO: 2; (3) residues 1 to 483 and residues 514 to 855 of SEQ ID NO: 2; and (4) residues 1 to 483 and residues 565 to 855 of SEQ ID NO: 2.

There are also four forms of the human CLOCK polypeptide that have been identified. Those four forms are: (1) SEQ ID NO: 55; (2) residues 1 to 513 and residues 565 to 846 of SEQ ID NO: 55; (3) residues 1 to 483 and residues 514 to 846 of SEQ ID NO: 55; and (4) residues 1 to 483 and residues 565 to 846 of SEQ ID NO: 55.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of the CLOCK polypeptide.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5)- Leu (−1.8); Ile (−1.8)- Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

The CLOCK polypeptide of the present invention contains numerous phosphorylation sites. This invention contemplates phosphorylated as well as unphosphorylated embodiments.

A CLOCK polypeptide of the present invention has numerous uses. By way of example, such a polypeptide can be used in a screening assay for the identification of drugs or compounds that inhibit the action of CLOCK polypeptide (e.g., DNA binding). The CLOCK polypeptide is an integral component of the circadian clock of mammals. As set forth below, animals lacking the ability to produce the CLOCK polypeptide have significant dysfunctions in their circadian clock. Mutant animals producing an altered CLOCK polypeptide can be given the normal CLOCK polypeptide together with suspected agonists or antagonists and the effects of such treatment on the restoration of a normal circadian rhythm can be determined. The CLOCK polypeptide can also be used to treat animals having circadian rhythm dysfunctions as set forth hereinafter.

In addition, a CLOCK polypeptide of the present invention can be used to produce antibodies that immunoreact specifically with the CLOCK polypeptide or antigenic detenninants thereof. Means for producing antibodies are well known in the art. An antibody directed against CLOCK polypeptide can be a polyclonal or a monoclonal antibody.

Antibodies against CLOCK polypeptide can be prepared by immunizing an animal with a CLOCK polypeptide of the present invention or an immunogenic portion thereof. Means for immunizing animals for the production of antibodies are well known in the art. By way of an example, a mammal can be injected with an inoculum that includes a polypeptide as described herein above. The polypeptide can be included in an inoculum alone or conjugated to a carrier protein such as keyhole limpet hemocyanin (KLH). The polypeptide can be suspended, as is well known in the art, in an adjuvant to enhance the immunogenicity of the polypeptide. Sera containing immunologically active antibodies are then produced from the blood of such immunized animals using standard procedures well known in the art.

The identification of antibodies that immunoreact specifically with CLOCK polypeptide is made by exposing sera suspected of containing such antibodies to a polypeptide of the present invention to form in a conjugate between antibodies and the polypeptide. The existence of the conjugate is then determined using standard procedures well known in the art.

A CLOCK polypeptide of the present invention can also be used to prepare monoclonal antibodies against CLOCK polypeptide and used as a screening assay to identify such monoclonal antibodies. Monoclonal antibodies are produced from hybridomas prepared in accordance with standard techniques such as that described by Kohler et al. (*Nature*, 256:495, 1975). Briefly, a suitable mammal (e.g., BALB/c mouse) is immunized by injection with a polypeptide of the present invention. After a predetermined period of time, splenocytes are removed from the mouse and suspended in a cell culture medium. The splenocytes are then fused with an immortal cell line to form a hybridoma. The formed hyridomas are grown in cell culture and screened for their ability to produce a monoclonal antibody against CLOCK polypeptide. Screening of the cell culture medium is made with a polypeptide of the present invention.

III. Clock Polvnucleotides

In another aspect, the present invention provides an isolated and purified polynucleotide that encodes a CLOCK polypeptide of mammalian origin. The polynucleotide can be a DNA molecule (e.g., genomic sequence, cDNA) or an RNA molecule (e.g. mRNA). Where the polynucleotide is a genomic DNA molecule, that molecule can comprise exons and introns interspersed therein.

As set forth hereinafter in the Examples, the Clock gene contains numerous exons. One of skill in the art will readily appreciate that the entire genome including introns is contemplated by the present invention. Where the polynucleotide is a cDNA molecule, disclosed sequences include coding regions as well as 5'- and 3'-untranslated regions.

Only coding DNA sequences are disclosed herein. The present invention also provides, however, non-coding strands that are complementary to the coding sequences as well as RNA sequences identical to or complementary to those coding sequences. One of ordinary skill will readily appreciate that corresponding RNA sequences contain uracil (U) in place of thymidine (T).

In one embodiment, a polynucleotide of the present invention is an isolated and purified cDNA molecule that contains a coding sequence for a CLOCK polypeptide of this invention. Exemplary and preferred such cDNA molecules are shown as SEQ ID NO: 1 and 54. SEQ ID NO: 2 is the deduced amino acid residue sequence of the coding region of SEQ ID NO: 1. As set forth above, a CLOCK polypeptide of the present invention can be a truncated or shortened form of SEQ ID NO: 2 or 55. Thus, preferred polynucleotides of this invention depend on the specific CLOCK polypeptide preferred.

By way of example, where the CLOCK polypeptide contains the amino residue sequence of SEQ ID NO: 2 from residue number 1 to residue acid number 855, a preferred polynucleotide contains the nucleotide sequence of SEQ ID NO: 1 from nucleotide number 389 to nucleotide number 2953. Where the CLOCK polypeptide contains the amino acid residue sequence of SEQ ID NO:2 from residue number 2 to residue number 855, a preferred polynucleotide contains the nucleotide sequence of SEQ ID NO: 1 from nucleotide number 392 to nucleotide number 2953. Where the CLOCK polypeptide contains the amino acid residue sequence of SEQ ID NO: 2 from residue number 10 to residue number 855, a preferred polynucleotide contains the nucleotide sequence of SEQ ID NO: 1 from nucleotide number 416 to nucleotide number 2953. Where the CLOCK polypeptide contains the amino acid residue sequence of SEQ ID NO: 2 from residue number 11 to residue number 855, a preferred polynucleotide contains the nucleotide sequence of SEQ ID NO: 1 from nucleotide number 419 to nucleotide number 2953. Where the CLOCK polypeptide contains the amino acid residue sequence of SEQ ID NO: 2 from residue number 35 to residue number 855, a preferred polynucleotide contains the nucleotide sequence of SEQ ID NO: 1 from nucleotide number 491 to nucleotide number 2953. Other preferred polynucleotides such as those encoding the four distinct forms of human CLOCK, will be readily apparent to a skilled artisan by reference to the cDNA and amino acid residue sequences disclosed herein.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for a CLOCK polypeptide of this invention as set forth hereinbefore.

As is well known in the art, because of the degeneracy of the genetic code, there are numerous other DNA and RNA molecules that can code for the same polypeptides as those encoded by SEQ ID NO: 1, or portions thereof. The present invention, therefore, contemplates those other DNA and RNA molecules 5 which, on expression, encode for a polypeptide that contains a polypeptide encoded by SEQ ID NO: 1, or portions thereof as set forth above. Having identified the amino acid residue sequence of CLOCK polypeptides, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE I

| First position | Second Position | | | | Third position |
|---|---|---|---|---|---|
| (.5' end) | T/U | C | A | G | (3' end) |
| T/U | Phe | Ser | Tyr | Cys | T/U |
|  | Phe | Ser | Tyr | Cys | C |
|  | Leu | Ser | Stop | Stop | A |
|  | Leu | Ser | Stop | Trp | G |
| C | Leu | Pro | His | Arg | T/U |
|  | Leu | Pro | His | Arg | C |
|  | Leu | Pro | Gln | Arg | A |
|  | Leu | Pro | Gln | Arg | G |
| A | Ile | Thr | Asn | Ser | T/U |
|  | Ile | Thr | Asn | Ser | C |
|  | Ile | Thr | Lys | Arg | A |
|  | Met | Thr | Lys | Arg | G |
| G | Val | Ala | Asp | Gly | T/U |
|  | Val | Ala | Asp | Gly | C |
|  | Val | Ala | Glu | Gly | A |
|  | Val | Ala | Glu | Gly | G |

A simple change in a codon for the same amino acid residue within a polynucleotide will not change the structure of the encoded polypeptide. By way of example, it can be seen from SEQ ID NO: 1 that a TCA codon for serine exists at nucleotide positions 422–424 and at positions 512–514. It can also be seen from that same sequence, however, that serine can be encoded by a AGC codon (see e.g., nucleotide positions 419–421 and 617–619). Substitution of the latter AGC codon for serine with the TCA codon for serine, or visa versa, does not substantially alter the DNA sequence of SEQ ID NO: 1 and results in expression of the same polypeptide. In a similar manner, substitutions of codons for other amino acid residues can be made in a like manner without departing from the true scope of the present invention.

A polynucleotide of the present invention can also be an RNA molecule. An RNA molecule contemplated by the present invention is complementary to or hybridizes under stringent conditions to any of the DNA sequences set forth above. As is well known in the art, such an RNA molecule is characterized by the base uracil in place of thymidine. Exemplary and preferred RNA molecules are mRNA molecules that encode a CLOCK polypeptide of this invention.

IV. Clock Oligonucleotides

The present invention also contemplates oligonucleotides from about 15 to about 50 nucleotides in length, which oligonucleotides serve as primers and hybridization probes for the screening of DNA libraries and the identification of DNA or RNA molecules that encode a CLOCK polypeptide. Such primers and probes are characterized in that they will hybridize to polynucleotide sequences encoding a CLOCK polypeptide. An oligonucleotide probe or primer contains a nucleotide sequence that is identical to or complementary to a contiguous sequence of at least 15 nucleotides of a polynucleotide of the present invention. Thus, where an oligonucleotide probe is 25 nucleotides in length, at least 15 of those nucleotides are identical or complementary to a sequence of contiguous nucleotides of a polynucleotide of the present invention. Exemplary polynucleotides of the present invention are set forth above.

A preferred oligonucleotide is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes a CLOCK polypeptide. Preferably, the antisense oligonucleotide is directed against the protein translational initiation site or the transcriptional start site. In accordance with this preferred embodiment, an antisense molecule is directed against a region of SEQ ID NO: I from about nucleotide position 370 to about nucleotide position 410 or a portion of SEQ ID NO: 1 from about nucleotide position 400 to about nucleotide position 440. It is understood by one of ordinary skill in the art that antisense oligonucleotides can be directed either against a DNA or RNA sequence that encodes a specific target. Thus, an antisense oligonucleotide of the present invention can also be directed against polynucleotides that are complementary to those shown in SEQ ID NO: 1 as well as the equivalent RNA molecules.

Preferably, the nucleotides of an antisense oligonucleotides are linked by pseudophosphate bonds that are resistant to clevage by exonuclease or endonuclease enzymes. Preferably the pseudophosphate bonds are phosphorothioate bonds. By replacing a phosphodiester bond with one that is resistant to the action of exo-and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art. A preferred method of polynucleotide synthesis is via cyanoethyl phosphoramidite chemistry. A detailed description of the preparation, isolation and purification of polynucleotides encoding mammalian CLOCK is set forth below V. Expression Vectors and Transformed Cells The present invention further provides expression vectors that contain a polynucleotide of the invention and host cells transformed or transfected with those polynucleotides or expression vectors.

A polynucleotide that encodes a CLOCK polypeptide is placed into an expression vector suitable for a given host cell such that the vector drives expression of the polynucleotide in that host cell. Vectors for use in particular cells are well known in the art and include viral vectors, phages or plasmids.

In one embodiment, a host cell is an eukaryotic host cell and an expression vector is an eukaryotic expression vector (i.e., a vector capable of directing expression in a eukaryotic cell). Such eukaryotic expression vectors are well known in the art. In another embodiment, the host cell is a bacterial cell. An especially preferred bacterial cell is an *E. coli*. Thus, a preferred expression vector is a vector capable of directing expression in *E. coli*

A polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" or its grammatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art.

An enhancer-promoter used in an expression vector of the present invention can be any enhancer-promoter that drives expression in a host cell. By employing an enhancer-promoter with well known properties, the level of expression can be optimized. For example, selection of an enhancer-promoter that is active in specific cells (e.g., cells of the SCN) permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art. The selection of a particular enhancer-promoter or transcription-terminating region will depend, as is also well known the art, on the cell to be transformed.

VI. Method of Making Clock Polynucleotide

In another aspect, the present invention provides a process of making a CLOCK polypeptide. In accordance with that process, a suitable host cell is transformed with a polynucleotide of the present invention. The transformed cell is maintained for a period of time sufficient for expression of the CLOCK polypeptide. The formed polypeptide is then recovered. Preferably, the polynucleotide is contained in an expression vector as set forth above.

VII. Pharmaceutical Compositions

The present invention also provides a pharmaceutical composition comprising a polypeptide, polynucleotide, oligonucleotide or expression vector of this invention and a physiologically acceptable diluent.

In a preferred embodiment, the present invention includes one or more antisense oligonucleotides, polypeptides or expression vectors, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracistemally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceuticalform can be brought about by the use of agents delaying absorption, for example, aluminum monostearate and gelatin.

Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar-agar and tragacanth, or mixtures of these substances, and the like.

VIII. Process of Using CLOCK Polypeptides, Polynucleotides and Oligonucleotides

The present invention provides processes for using the polypeptide, polynucleotides, and oligonucleotides of the present invention. The compositions and methods of the present invention have a variety of uses. Having described the Clock gene and its expression product, the CLOCK polypeptide, it is possible to inhibit expression of the Clock gene using gene targeting technology as is well know in the art. Using such technology, for example, the Clock gene can be removed from the genome of the mouse or that gene can otherwise be mutated so as to prevent expression of the CLOCK polypeptide. As a result of such treatments, a mouse model is created that is characterized by having circadian clock dysfunctions. That model can then be used in screening essays to identify therapeutic agents that affect circadian rhythm or to study a variety of chemical, physiological, or behavioral activities associated with the circadian rhythm.

As set forth above, the amino acid residue sequence of the CLOCK polypeptide indicates that it is a transcription factor and contains a DNA binding domain. The CLOCK polypeptide, or the DNA binding domain portion thereof, can therefore be used to identify the specific DNA binding site and/or to identify agonist or antagonist substances that interfere with DNA binding of the CLOCK polypeptide. Means for accomplishing such screening assays are well known in the art.

Briefly, once the DNA binding site is identified, that DNA binding site, together with the DNA binding domain of the CLOCK polypeptide, can be exposed to a variety of agents suspected of being agonists or antagonists to DNA binding. The ability of those compounds to interfere with binding of the CLOCK polypeptides to its DNA binding site is indicative of the agonist or antagonist nature of those substances. Alternatively, the DNA binding site can be placed in an expression vector such that binding of a CLOCK polypeptide to that binding site allows for expression of a reporter gene operatively linked to the DNA binding site. The ability of compounds to inhibit or enhance expression of the reporter gene is indicative of agonist or antagonist activity.

The CLOCK polypeptide, or the DNA binding domain thereof, can also be used to screen DNA libraries to identify the specific binding site on a DNA molecule. Screening can be accomplished with genomic libraries in general or with specifically targeted portions of genomic DNA. As set forth above, for example, it is likely that the DNA binding domain of the CLOCK polypeptide binds within the promoter region of the Clock gene itself. Binding studies can therefore be targeted to this region of the Clock gene.

Once the DNA binding site of the CLOCK polypeptide has been determined, the three dimensional structure of the CLOCK polypeptide, or its DNA binding domain, bound to the target DNA site can be determined using techniques well known in the art, such as X-ray crystallography. Knowledge of the three-dimensional structure of the bound CLOCK polypeptide will thus allow for computer aided rational drug design for identification of agonist or antagonist compounds.

The well known yeast two-hybrid system can be used to determine whether the CLOCK polypeptide interacts with another protein (heterodimerization) or with itself (homodimerization). Briefly, yeast cells are transformed with a reporter gene operatively associated with a promoter that contains a binding site for GAL 4. That same yeast is then transformed with a polynucleotide that encodes a CLOCK polypeptide of the present invention, or a dimerization domain thereof. Finally, that same yeast cell is transformed a protein expression cDNA library. Transformed yeast will only survive if the CLOCK polypeptide interacts with a second protein resulting from expression of the protein expression cDNA library and that interaction causes GAL 4 to bind to the promoter region of the reporter gene and express that reporter gene.

In yet another embodiment, compositions of the present invention can be used to screen genomic libraries in plants and animals to identify the corresponding Clock genes in these species. Identification of the Clock gene in these species is important because the growth and metabolic rate of plants and animals is known to be regulated, at least in part, by the circadian rhythm. By way of example, photosynthesis in plants is known to comprise both a light and dark reaction. Manipulation of the circadian clock in plants, therefore, can result in alteration of those light and dark reactions. Similarly, the growth rate of animals used for feed (cattle and pigs) is known to be a finction of the circadian rhythm. The ability to manipulate the circadian rhythm in those animals can thus result an enhanced growth of those important animals.

The expression of diurnal (i.e. 24-hr) rhythms is a findamental property of almost all forms of life. These rhythms are regulated by an internal "biological clock" that in many organisms, including humans, can be synchronized by the light dark cycle. This internal 24-hr clock is referred to as a "circadian clock" because in the absence of any diurnal environmental cues, the period of the clock is rarely exactly 24 hours but is instead about 24 hrs (i.e. circa diem).

The circadian clock in mammals is known to regulate 24 hour rhythms in biochemical, cellular, metabolic and behavioral activity in most, if not all, physiological systems. The following is a list of exemplary activities controlled at least in part by the circadian clock and activities that affect that clock, which can be manipulated to restore the finction of an abnormal allele of the Clock gene.

1. The circadian clock is a major regulator of the sleep-wake cycle (Borbély, 1994; Kryger et al., 1994) and many pathologic changes in the sleep wake cycle are associated with circadian rhythm disorders (Roehrs and Roth, 1994). Therefore, this patent covers any use of Clock; or its protein product, for the development or use of new techniques and/or pharmaceutical approaches for the treatment of any sleep disorders.

2. When people move rapidly across time zones, they suffer from a well-known syndrome, referred to as jet-lag, until their biological clock and sleep-wake cycle become resynchronized to the new time zone (Graeber, 1994). Therefore, this patent covers any use of Clock, or its protein product, for the development or use of new techniques and/or pharmaceutical approaches for the treatment of jet-lag.

3. When people must be awake during the normal sleep period, and/or asleep during the normal wake period, they suffer decrements in health, performance and productivity as well as an increased rate of accidents (Monk, 1990; Monk, 1994; Smith et al., 1994; US Congress, September, 1991). Therefore, this patent covers any use of Clock, or its protein product, for the development or use of new techniques and/or pharmaceutical approaches for the treatment of disorders of time-keeping associated with having to be awake during the biological clock time of normal sleep and asleep during the biological clock time of normal wake. This coverage of the patent includes the use of Clock, and/or it's protein product for alleviating the adverse effects associated with shift work where workers are working during the time of normal sleep and sleeping during the time of normal wake.

4. The circadian clock regulates the timing of fatigue and alertness (Monk et al., 1984; Roth et al., 1994). Therefore, this patent covers any use of Clock, or its protein product, for the development or use of new techniques and/or pharmaceutical approaches for altering the cycle of fatigue and alertness, as well as for decreasing fatigue or increasing alertness by altering circadian rhythmicity.

5. Circadian rhythm disruption has been associated with many forms of altered mental states, including but not limited to depression (both unipolar and bipolar), premenstrual syndrome post-menopausal syndrome, and schizophrenia (Hallonquist et al., 1986; Ohta and Endo, 1985; Van Cauter and Turek, 1986; Wehr and Goodwin, 1983; Wehr et al., 1983; Wehr et al., 1979). Therefore, this patent covers any use of Clock, or its protein product, for the development or use of new techniques and/or pharmaceutical approaches for the treatment of any mental disorders.

6. Studies have shown that the human has a pronounced cycle of mood and performance (Benca, 1994; Monk et al., 1985). Therefore, this patent covers any use of Clock, or its protein product, for the development or use of new techniques and/or pharmaceutical approaches for altering the mood state or performance.

7. The circadian clock regulates the timing of many physiological and endocrine processes that when disturbed lead to various mental and physical disorders (Richter, 1979; Turek and Van Cauter, 1994; Van Cauter and Turek, 1995). Therefore, this patent covers any use of Clock, or its protein product, for the development or use of new techniques and/or pharmaceutical approaches for the treatment of any mental and physical disorders.

8. Abnormal circadian rhythm and abnormal sleep-wake cycles have been associated with various neurological diseases (Aldrich, 1994; Bliwise, 1994; Hartmann, 1994; Hineno et al., 1992; Hyde et al., 1995; Lugaresi and Montagna, 1994; Poirel, 1991; Weltzin et al., 1991). Therefore, this patent covers any use of Clock, or its protein product, for the development or use of new techniques and/or pharmaceutical approaches for the treatment of any neurological disorders.

9. The circadian clock regulates the timing of many physiological and endocrine processes associated with stress (Sapolsky, 1992; Tomatzky and Miczek, 1993; Van Cauter and Turek, 1995). Therefore, this patent covers any use of Clock or its protein product, for the development or use of new techniques and/or pharmaceutical approaches for relieving stress or altering the stress response in humans.

10. Many components of the cardiovascular system show rhythmic variation, and the timing of such major insults to the cardiovascular system, such as heart attack and stroke, are known to be regulated by the circadian clock system and/or be influenced by the time-of-day (Aschoff, 1992; Cohen and Muller, 1992; George, 1994; Gillis and Flemons, 1994; Maron et al., 1994; Sano et al., 1995). Therefore, this patent covers any use of Clock, or its protein product, for the development or use of new techniques and/or pharmaceutical approaches for the treatment of any diseases of the cardiovascular system.

11. The circadian clock plays a central role in the regulation of the diurnal cycle in feeding behavior (Rusak and Zucker, 1975). Furthermore, many components of the system involved with feeding as well as the regulation of metabolism, body fat and weight control are regulated by the circadian clock system (Benca and Casper, 1994; de Graaf et al., 1993; Larsen et al., 1991; Orr, 1994; Van Cauter and Turek, 1995). Therefore, this patent covers any use of Clock, or its protein product, for the development or use of new techniques and/or pharmaceutical approaches for the treatment of any disorders of feeding behavior as well as attempts to regulate diet and/or food intake.

12. The circadian clock regulates the timing of many physiological and endocrine events associated with diabetes (Spallone et al., 1993; Van Cauter and Turek, 1995). Therefore, this patent covers any use of Clock, or its protein product, for the development or use of new techniques and/or pharmaceutical approaches for the treatment of diabetes and related illnesses.

13. The circadian clock regulates the timing of many components of the immune system (Calvo et al., 1995; Constantinescu, 1995; Krueger and Kamovsky, 1995). Therefore, this patent covers any use of Clock, or its protein product, for the development or use of new techniques and/or pharmaceutical approaches for the treatment of any disorders of the immune system.

14. For many infectious diseases, including those of viral, bacterial or parasitic origins, the circadian clock regulates the optimum time for infection to occur, as well as the response to the infection by the host organism (Walker et al., 1981). Therefore, this patent covers any use of Clock, or its protein product, for the development or use of new techniques and/or pharmaceutical approaches for the prevention, diagnosis and/or treatment of infectious diseases.

15. The circadian clock regulates the timing of many processes associated with reproduction (Turek and Van Cauter, 1994). Therefore, this patent covers any use of Clock, or its protein product, for the development or use of new techniques and/or pharmaceutical approaches for the treatment of any reproductive disorder as well as for enhancing fertility, treating infertility or for any birth control methods as well as for affecting sexual function.

16. Many of the physiological processes and hormones involved in pregnancy and parturition are regulated by the circadian clock (Turek and Van Cauter, 1994). Therefore, this patent covers any use of Clock, or its protein product, for the development or use of new techniques and/or pharmaceutical approaches for aiding in the maintenance of pregnancy and/or in the process of parturition.

17. The circadian clock regulates the timing of many components of the respiratory system (Douglas, 1994; Orem, 1994). Therefore, this patent covers any use of Clock, or its protein product, for the development or use of new techniques and/or phan-naccutical approaches for the treatment of any respiratory illness.

18. There are pronounced diurnal variations in the functions of the liver (Colantonio et al., 1989; Garcia-Pagáan et al., 1994). Therefore, this patent covers any use of Clock, or its protein product, for the development or use of new techniques and/or pharmaceutical approaches for the treatment of liver disease and or for altering liver finction.

19. Many components of the endocrine system undergo pronounced daily changes in fuiction (Van Cauter and Turek, 1995). Therefore, this patent covers any use of Clock, or its protein product, for the development or use of new techniques and/or pharmaceutical approaches for the treatment of any endocrine disorders, or for altering in endocrine rhythms for any purposes.

20. The circadian clock regulates the timing of the pineal melatonin rhythm (Arendt, 1995). Therefore, this patent covers any use of Clock, or its protein product, for the development or use of new techniques and/or pharmaceutical approaches for using melatonin and/or melatonin related drugs in humans for therapeutic purposes, including the use of melatonin and/or melatonin related drugs as antioxidants.

21. The therapeutic and toxic effects of many drugs are influenced by the time of day at which the drug is delivered and/or by the pattern of drug administration (Larsen et al., 1993; Lemmer, 1989; Walker et al., 1981). Therefore, this patent covers any use of Clock, or its protein product, for the development or use of new approaches for the use of any pharmacological agents to improve human health or welfare.

22. The therapeutic and toxic effects of many drugs are influenced by the time of day at which the drug is delivered and/or by the pattern of drug administration (Walker et al., 1981). Therefore, this patent covers any use of Clock, or its protein product, for the development or use of new techniques and/or pharmaceutical approaches in the screening of drugs for new therapeutic purposes as well as the use of Clock and its protein product for diagnostic purposes.

23. The circadian clock regulates many physiological processes that are involved in the development or suppression of many forms of cancer (Walker et al., 1981). Therefore, this patent covers any use of Clock, or its protein product, for the development or use of new techniques and/or pharmaceutical approaches for the treatment or diagnosis of any cancer, as well as other forms of abnormal cell division.

24. The circadian clock regulates many of the processes associated with growth and development (Albertsson-Wlkland and Rosberg, 1988, Hokken-Koelega et al., 1990; Mirmiran et al., 1990; Van Cauter and Turek, 1995). Therefore, this patent covers any use of Clock, or its protein product, for the development or use of new techniques and/or pharmaceutical approaches for influencing growth and development.

25. The circadian clock regulates processes associated with cell division (Edmunds Jr, 1988). Therefore, this patent covers any use of Clock, or its protein product, for the development or use of new techniques and/or pharmaceutical approaches for influencing cell division and the cellular cycle.

26. There are major changes in the circadian clock system with advancing age, and age-related changes in the circadian clock system may underlie many of the adverse health effects associated with aging (Turek et al.,1995; Van Cauter and Turek, 1995). Therefore, this patent covers any use of Clock, or its protein product, for the development or use of new techniques and/or pharmaceutical approaches for the treatment of any age-related illnesses or age-related changes in human physiology.

27. Light may have many effects on the brain that are mediated through the transmission of neural information through the central circadian clock in mammals, the hypothalamic suprachiasmatic nucleus (SCN) (Card and Moore, 1991; Meijer, 1991; Penev et al., 1997). Therefore, this patent covers any use of Clock, or its protein product, for the development or use of new techniques and/or pharmaceutical approaches for the use of light to alter neural activity in the brain.

28. The light-dark cycle is a major regulator of the timing of circadian rhythms that are controlled by the circadian clock of which Clock is a component (Turek, 1994; Turek and Van Reeth, 1996; Van Cauter and Turek, 1995). Therefore, this patent covers any use of Clock, or its protein product, for the development or use of new techniques and/or pharmaceutical approaches that involve the use of light or dark to shift or influence, in any way, circadian rhythm.

29. While the light-dark cycle is a major regulator of the timing of circadian rhythm in most humans, for many blind humans the light-dark cycle is not able to synchronize the circadian clock in a normal fashion (Sack et al., 1992). Therefore, this patent covers any use of Clock, or its protein product, for the development or use of new techniques and/or pharmaceutical approaches for the treatment of blind people.

30. The light-dark cycle influences many finctions of the retina including photoreceptor cells. Furthermore, the circadian clock regulates the timing of many genetic, molecular and cellular processes in the retina (Decker et al., 1995; LaVail, 1976; Young, 1980). Therefore, this patent covers any use of Clock, or its protein product, for the development or use of new techniques and/or pharmaceutical approaches for the treatment in any fashion of retinal dysfunction.

31. The circadlan clock regulates a diurnal rhythm in mental and physical performance in animals, including humans (Benca, 1994; Monk et al., 1985; Richter, 1979; Turek and Van Cauter, 1994; Van Cauter and Turek, 1995). Therefore, this patent covers any use of Clock, or its protein product, for the development or use of new techniques and/or pharmaceutical approaches for enhancing human mental and physical performance.

32. Increased exercise at certain times of the day is known to be able to shift circadian rhythms that are controlled by the circadian clock (Van Reeth et al., 1994). Therefore, this patent covers any use of Clock, or its protein product, for the development or use of new techniques and/or pharmaceutical approaches that involve the use of exercise to shift or influence in any way circadian rhythms.

33. The disruption of normal circadian rhythmicity in intensive care facilities has been associated with decreased wellness and increased morbidity (Mann et al., 1986). Therefore, this patent covers any use of Clock, or its protein product, for the development or use of new techniques and/or pharmaceutical approaches for improving the environment of intensive care facilities or the health of the subjects such facilities.

34. The circadian clock plays a central role in the regulation of diurnal rhythms in plant and animal species that are of commercial value to humans (1988; Reiter and Follett, 1980). Therefore, this patent covers any use of Clock, or its protein product, for the development or use of new techniques and/or pharmaceutical approaches for enhancing the growth, development, performance, productivity, or health of such species, including those involved in the production of food for human consumption, as well as animal products used in producing apparel.

35. The circadian clock plays a central role in measuring the length of the day, which changes on an annual basis in all regions on earth outside of those close to the equator (1988; Reiter and Follett, 1980; Turek and Van Cauter, 1994). This seasonal change in day length influences the growth, development, health, reproduction, performance and productivity of many species, including humans (1988; Reiter and Follett, 1980; Turek and Van Cauter, 1994). Therefore, this patent covers any use of Clock, or its protein product, for the development or use of new techniques and/or pharmaceutical approaches for influencing any seasonal rhythms in any species, including the use of melatonin and/or melatonin related drugs to influence seasonal cyclicity.

36. The treatment of one sub-type of depression, referred to as Seasonal Affective Disorder (SAD), has been the exposure to extra bright light during the short days of winter (Penev et al., 1997; Terman, 1994; Wetterberg, 1994). Such treatment may be effective because of the effect of light on the circadian clock system. Therefore, this patent covers any use of Clock, or its protein product, for the development or use of new techniques and/or pharmaceutical approaches for the treatment of SAD or any other disorders that are associated with the seasonal change in daylength.

37. Since Clock is the first gene to be discovered and cloned in a mammal that is a component of the circadian clock, it will lead to the discovery of new Clock genes that have sequence homology with Clock and its protein product. Therefore, this patent covers any use of Clock, or its protein product, to discover and clone new genes, and their protein products by sequence homology (and their commercial value).

38. Since Clock is the first gene to be discovered and cloned in a mammal that is a component of the circadian clock, it will lead to the discovery of new Clock genes, and their protein products, that interact with Clock or the Clock protein product. Therefore, this patent covers the use of Clock, or its protein product, to discover new genes, and their protein products that are found by determining which genes and their protein products interact with Clock, and its protein product, in a functional way.

39. Since Clock is the first gene to be discovered and cloned in a mammal that is a component of the circadian clock, it will lead to the discovery of new Clock genes, and their protein products, that interact with Clock or the Clock protein product. Therefore, this patent covers the use of Clock, or its protein product to screen for molecules that may have sequence similarity or finctional relationships to clock or its protein product.

40. The circadian clock regulates the timing of the expression of many genes and the production of their protein products (Jacobshagen and Johnson, 1994; Lausson et al., 1989; Loros et al., 1989; Millar and Kay, 1991; Taylor, 1989). Therefore, this patent covers any use of Clock, or its protein product, for the development or use of new techniques and/or pharmaceutical approaches in the use of gene therapy where a particular gene and/or its protein product needs to be under or over-expressed.

41. The circadian clock is a major regulator of the sleep-wake cycle and many pathological changes in the sleep-wake cycle are associated with circadian rhythm disorders (Kryger et al., 1994). Therefore, this patent covers any use of Clock, or its protein product, for the development or use of new techniques and/or pharnaceutical approaches for the discovery of genes and their protein products that are involved in the regulation of the sleep-wake cycle.

The Examples to follow illustrate particular embodiments of the present invention and are not limiting of the specification and claims in any way.

EXAMPLE 1

Isolation and Phenotypic Analysis of the Mouse Clock Mutation

Because orthologs of the canonical clock genes (period, timeless, and frequency) have not been found in mammals, and because other strategies to identify mammalian clock genes have not yet been successful, a mutagenesis screening strategy to isolate clock mutations in the mouse was initiated (Takahashi et al. 1994). Circadian behavior in the mouse is precise and easily quantitated, thus it is very well suited for genetic screening. Wild type C57BL/6J strain mice, which were used for this screen, exhibit a robust circadian rhythm of wheel running activity (Pittendnigh & Daan 1976, Schwartz & Zimmerman 1990). This behavioral assay was used to screen for mice carrying mutations that cause abnormal circadian periods in constant darkness. Because most clock mutations that have been isolated in other organisms have been semidominant (Hall & Kyniacou 1990, Dunlap 1993), dominant and semidommant mutations were screened for. Analysis of about 300 $G_1$ progeny of ENU-treated mice revealed one mouse that expressed a circadian period that was more than one hour longer than (and six standard deviations above) the normal period of 23.7 hours (Vitatema et al. 1994). This long period phenotype was inherited as a single-locus, semidommant, autosomal mutation, which was designated Clock.

Mice homozygous for the Clock mutation expressed extremely long circadian periods of about 28 hours for the first two weeks of exposure to constant darkness, after which there was a complete loss of circadian rhythmically. The Clock gene, thus, regulates at least two fundamental properties of the circadian clock system: the intrinsic circadian period and the persistence of circadian rhythmicity. No anatomical defects in the SCN have been observed in association with the Clock mutation (Vitatema et al. 1994), which suggests that the loss of circadian rhythmicity in constant darkness cannot be attributed to a gross anatomical or developmental defect.

In addition to the effects on period and persistence of circadian rhythms in Clock mutants, at least two other circadian effects of the mutation have been documented. The period of Clock heterozygous mice is unstable and their free-running periods tended to lengthen with time in constant darkness. In addition, the photic entrainment of Clock heterozygotes is also altered. Clock/+ mice were able to entrain to 28-hour light cycles, while wild-type mice did not. Importantly, Clock/+ mice also exhibited high-amplitude phase-resetting responses to 6-hour light pulses (Type 0 resetting) as compared to wild-type mice which exhibited low amplitude (Type 1) phase resetting. Because of their loss of rhythmically in constant conditions, phase shifts in response to light pulses could not be measured in Clocki-Clock homozygotes, but two findings indicate that these animals can entrain: the phase of a restored rhythm following a light pulse and the phase of the free-run following entrainment to a light dark cycle were both determined by the phase of the light signal. The increased efficacy of photic resetting stimuli and the decrease in period stability suggest that the Clock mutation may reduce circadian pacemaker amplitude in Clock heterozygotes.

To determine whether the Clock mutation affects other rhythms in mice, circadian drinking rhythms were measured. The Clock mutation affected the period and persistence of circadian drinking rhythms in a manner similar to that seen with activity suggesting that the mutation acts globally on rhythms in mice and is not restricted to locomotor activity.

The phenotype of Clock is as robust as the "best" clock mutations in Drosophila and Neurospora (Dunlap 1993). By robust is meant that the period change is on the order of 4 to 5 hours, which is followed by a complete loss of circadian rhythmicity. The magnitude of the period change in Clock homozygotes was equivalent to that seen with the $per^L$ and $frq^7$ alleles that also cause periods of 28–30 hours in their respective organisms (Dunlap 1993). The loss of circadian rhythmicity seen in Clock homozygotes resemble that seen in $per^0$ and $frq^9$ alleles, which are null mutations in those respective genes (Dunlap 1993). The robustness of Clock is important for two reasons. First, mutations that have modest effects on period length (on the order of a one-hour change in period in homozygotes) could be due to secondary effects of mutations on the circadian clock system. Second, the most robust mutants in Drosophila and Neurospora are found at the per, tim and frq loci, which are genes that appear to be critical and essential elements of the circadian mechanism in these organisms (discussed above).

EXAMPLE 2

Antimorohic Behavior of Clock Mutation

The initial analysis of the Clock mutation indicated that the mutation exhibited a semidominant phenotype (Vitatema et al. 1994). There are several possible causes of a semi-dominant phenotype, including the possibility that the mutation was induced in a gene that otherwise is not involved in the generation of circadian rhythms, but when mutated, interferes with the normal generation of these rhythms. To demonstrate that a particular gene is necessary for a particular biological process, one normally requires a loss-of-function allele of that gene leading to a loss of the phenotype in question. From genetic mapping (described below) it was found that Clock is contained within a radiation induced deletion on chromosome 5, $W^{19H}$, that includes the Kit (=W, Dominant White Spotting) locus (Lyon et al. 1984). This was found by mapping the SSLP content of $W^{19H}$ in ($W^{19H}$ x Mus castaneous/Ei) $F_1$ progeny. Multiple genetic loci, mapping both proximal from and distal of Clock, are within the $W^{19H}$ deletion, indicating that Clock maps within this deletion. Access to this deletion that encompasses Clock allowed for further analysis of the phenotypic effect of this mutation. Muller's classic analysis of Drosophila mutations (Muller 1932), as well as more recent analysis of dominant mutations in Caenorhabditis elegans (Park & Horvitz 1986), provided a framework in which to analyze the Clock mutation. Muller described five types of mutant alleles, distinguished by manipulating the copy number of the mutant and wildtype alleles (via, e.g., deletions). These are hypomorph, amorph, hypermorph, antimorph, and neomorph alleles. The circadian phenotype of $W^{19H}$ heterozygous mice (hemizygous for the wild-type allele of Clock) is indistinguishable from the wild-type phenotype on a comparable strain background, indicating that the null allele of Clock is recessive to wild-type. By mating Clock/Clock mice to mice heterozygous for this deletion to generate $F_1$ progeny, it was possible to measure the phenotype of Clock/null animals (these $F_1$ animals are distinguishable from their Clock/+ litter mates by the presence of deletion-induced white coat color markings). Of particular intrest is the observation that the mean circadian period expressed by Clock/null animals (25.6±0.1.5 hours) is significantly longer than that of Clock/+ animals (24.2±0.05 hours, $p<10^{-7}$). This indicated that the wild-type allele interacts with the Clock mutation to ameliorate the severity of the Clock mutant phenotype. This is the essential feature of an antimorphic (Muller 1932), and is in contrast to what would be expected of a neomorph mutation, in which case the wild-type allele would have no effect on the expression or severity of the mutant allele. Furthermore, because $W^{19H}$ is large (~2.8 cM) and because multiple loci, both proximal from and distal of Clock, lie within the deletion, it appears unlikely that the breakpoints of the deletion interact directly with the Clock gene. That Clock is an antimorph (one type of dominant negative mutation) implies that the wild-type allele finction in the normal generation of circadian rhythms in the mouse. This provides strong evidence that Clock defines a gene central to the mammalian circadian system.

The antimorphic behavior of the Clock allele provided clues about the nature of this mutation. Antimorphic behavior suggested that the mutant allele generates a molecule that competes with the wild-type finction. This, and the observation that Clock/deletion and Clock/+ have much more severe phenotypes that+/deletion; allows the conclusion that the Clock mutation is unlikely to be either a null mutation (amorph), or a partial loss of finction (hypomorph). Further, because+/deletion has no phenotype different from wild-type, the Clock phenotype does not appear to be the result of haplo-insufficiency. Perhaps most important, it is likely that the mutation conferring the altered behavior in Clock mutant mice may affect the coding sequence of the gene, due to its ability to interfere with the finction of the wild-type allele.

EXAMPLE 3

Genetic Mapping of Clock

The first step in the molecular identification of Clock locus was to map its location in the mouse genome. Given the extensive genetic mapping information available in the mouse (Takahashi at al. 1994), it was possible to map Clock rapidly by linkage analysis using intraspecific mapping crosses and simple sequence length polymorphisms (SSLPs) from the MIT/Whitehead Institute genetic map (Vitaterna et al. 1994). Clock mapped to the mid portion of mouse chromosome 5 between two SSLP markers, D5Mit24 and D5Mit83, in a region that shows conserved synteny with human chromosome 4. The possibility of a human homolog of Clock on chromosome 4 is significant because it allows for focusing attention upon this region of the genome for possible linkage to circadian traits in human subjects as well as providing a candidate gene for other disorders associated with circadian rhythm dysfimctions such as delayed sleep phase syndrome (Vignau et al. 1993) and affective disorders (Wehr & Rosenthal 1989).

In order to identify a more precise chromosomal region in which to focus physical mapping and molecular cloning efforts, a high-resolution genetic. map of the Clock region was genereated using SSLPs and 1804 meioses obtained from 6 intraspecific and 2 interspecific crosses. This SSLP mapping placed Clock close to the Kit (=W, Dominant white spotting) locus (Geissler et al. 1988b). High resolution genetic mapping, with a PruII RFLP identified using a Kit cDNA probe, placed Kit 0.7 cM (7 recombinants/988 meioses) proximal from Clock.

Using additional SSLP markers on a total of 2681 meioses, Clock has now been placed within a 0.3 cM interval, approximately 0.2 cM (5 recombinants/2681 meioses) distal of D5Mit3O7 and 0.1 cM (1 recombinant/ 845meioses) proximal from D5Mit/D5Mit306 (see FIG. 1). The location of this distal recombination has been confirmed in test-cross progeny.

EXAMPLE 4

Physical Mapping of the Clock Region

Figure 2:
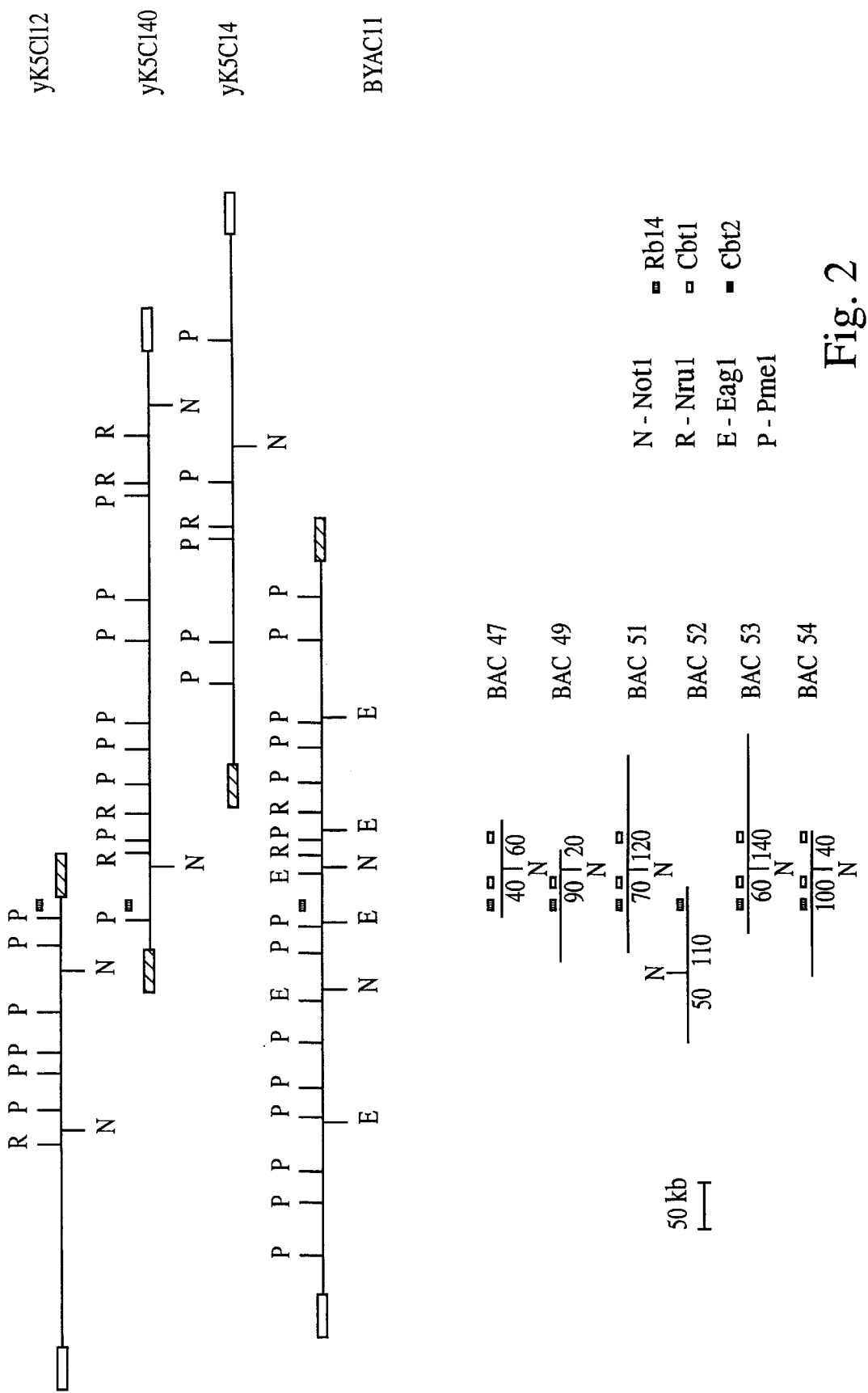
FIG. 2 is a schematic illustration of restriction mapping of YAC and BAC clones in the Clock region.

Based upon the high-resolution genetic map of the Clock region, a physical map which spanned the critical genetic region that must contain Clock (D5Mit307-D5Mit112) was constructed. To do this, yeast, artificial chromosome (YAC) clones that map to the region were isolated. Using a YAC library that has been pooled for PCR screening (Kusumi et al. 1993), and SSLP markers, as well as sequence tagged sites (STSs), from the region surrounding Clock, over 40 YAC clones were isolated and a contig of ~4 Mb that spans the Clock region (FIG. 1) was constructed. YAC clones within the critical region were characterized by end cloning and long-range restriction mapping with pulse field gel electrophoresis (PFGE). Three nonchimeric YAC clones were identified and one of these YACs, which is 930 kb, contains both flanking markers and therefore must contain Clock. Long-range restriction mapping of the reduced genetic interval D5Mit307-D5Mit112 indicated that it was about 400 kb in length (See FIG. 2). Most of this 400 kb critical region was then re-cloned in bacteria artificial chromosome (BAC) clones. BACs, which are intermediate in size (~100–200 Kb) between YACs and cosmids, have several advantages when compared to YAC clones. Although they are generally smaller than YAC clones, BACs are rarely chimeric, they are circular clones, thus they are much easier to manipulate, and they rarely suffer recombination or deletion damage (Shizuya et al. 1992). Using direct sequencing of the ends of the BAC clones, 12 BACs were placed on the YAC physical map using STSs. Subclone libraries from these BAC clones were placed to isolate 7 new SSLP markers. One of these markers, D5NWU1 was non-recombinant with Clock, and a second marker, D5NWU2, defined the closest distal recombinant with Clock on the genetic and physical map. Thus the critical region containing Clock was now defined by the flanking markers D5Mit307 and D5NWU2 which defined an interval less than 400 kb.

EXAMPLE 5

Transcription Unit Analysis in the Clock Region

Within the critical region containing Clock there are no known candidate genes that have previously been identified. Therefore three different approaches identifying candidate genes were initiated: 1) direct screening of SCN cDNA libraries with BAC clones as probes; 2) hybridization selection of cDNAs from SCN libraries using BAC clones as driver; and 3) shotgun sequencing random M13 libraries made from BAC clones.

The first two of these methods used a pair of oligo dT primed cDNA libraries. Tissue derived from mouse SCN region was microdissected from a total of about 100 mice at four different circadian time points (circadian time (CT) 1,7,13, and 19). For one of these libraries, poly $A^+$RNA was extracted from SCN tissue collected in constant darkness at each time point. For the other library, poly $A^+$RNA was extracted from SCN tissue collected at the same four time points: however, the animals were previously exposed to a 30 to 90 minute pulse of light. cDNA libraries were directionally cloned using the ZAP Express lambda vector (Stratagene). Primary library sizes were $1.7 \times 10^6$ and $1.2 \times^6$ pfu, and $1 \times 10^6$ clones from each library were plate amplified. Average insert sizes were 2.3 and 2.2 kb and raged from 600 to 5200 bp. These cDNA libraries are important resources because the SCN is very small (about 16–20,000 neurons or ~20 g protein per mouse) and is difficult and expensive to obtain high quality mRNA samples.

A. Direct Screening of the cDNA Libraries Using Whole BAC Inserts.

Figure 3:
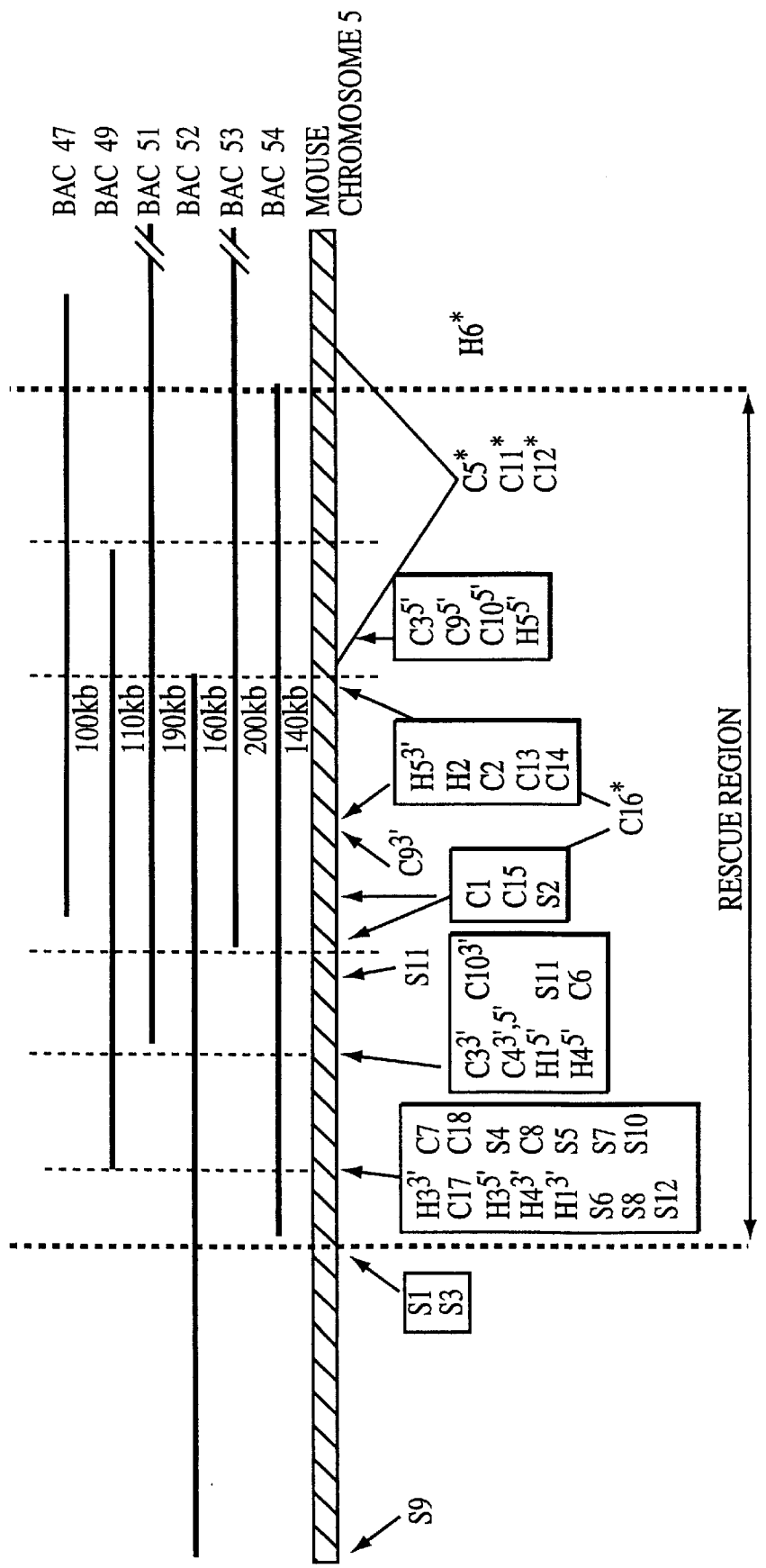
FIG. 3 is a schematic illustration of a transcript map of the Clock region.

Two different BAC clones were used which together cover<¾ of the critical region containing Clock. BAC DNA for probes was purified by restirction digest with Not I to release inserts and separation of field inversion gel electrophoresis (FIGE). BAC insert DNA was radiolabeled using random priming and the probe was preannealed with Cot-1 mouse DNA to suppress repetitive DNA sequences using methods similar to those developed for probes from entire YAC clones (Marchuk & Collins 1994). The cDNAs identified using the method were characterized in two ways. The ends of the clones were sequenced and these sequences were used to search the DNA and protein databases, using the Basic Local Alignment Search Tool (BLAST) (Altschul et al. 1990). Also, these cDNA clones were used as probes on a Southern blot consisting of BAC clones, restriction digested with HindIII, that map to the critical genetic region. Using these two methods, it was possible to eliminate false positive clones by identifying clones containing repetitive sequences (e.g., L1 elements) and clones that did not map to the critical genetic region (i.e., they did not hybridize to the BAC clone Southern blot). This process led to the identification of fifteen cDNA clones that fell into 6 classes of cDNA clones mapping in the Clock region. These 6 classes of clones are referred to as "H1 through H6" in (See FIG. 3).

B. cDNA Selection Experiments

The second method used to identify transcription unit sequences was an adaption of the cDNA selection protocol described by Lovett (Lovett 1994). For these experiments, SCN cDNA from lambda DNA was prepared from plate lysates from the SCN libraries described above. Lambda DNA from the cDNA library (instead of excised phagemid DNA) was used because the purification of cDNA inserts were excised by digestion with BamHI and XhoI and gel purified from lambda vector arms. cDNA was then digested with DpnII, and BamHI adapters form the representational difference analysis (RDA) method (Lisitsyn et al. 1993) were ligated. Amplicons from the cDNA fragments were then made by PCR as described in the RDA procedure. Genomic DNA from BAC clones was released with Not I digestion and inserts were purified on pulse-field gel electrophoresis (PFGE). BAC DNA was the digested with Sau3AI, and a different set of BamHI RDA adapters was ligated. Amplicons from the BAC DNA were then made by PCR using a biotin end-labeled oligonucleotide primer. cDNA and BAC amplicons were then hybridized in the presence of Cot-1 mouse genomic, ribosomal and vector DNA to suppress background. Hybrids were then captured with streptavidin-coated magnetic beads as described by Lovett. Two rounds of selection were performed and the efficiency was monitored with a positive control (spiked with c-fos clone), a negative control (jun-B) and Cot-1 DNA level.

Selected clones were then eluted and cloned into pBluescript vector. Clones were then picked into six 96-well plates. Replica filters were made and screened with the following probes: BAC 51 (positive probe), BAC 48 (negative probe), c-fos, and Cot-1 DNA. Clones that were positive for BAC 51 and negative for the other three probes were analyzed. Sixty cDNA such clones were selected. These 60 selected clones were then sequenced to identify duplicates and tested for mapping back to the Clock region on Southern blots of HindIII digested BAC clones from the critical region. Out of the 60 clones, 38 appeared valid by sequence, 14 had repetitive sequences and 8 were false positives (ribosomal or vector DNA). All 38 clones mapped to the Clock region BAC Southern blots. The selected cDNA fragments appeared to fall into about 13 classes. These fragments were then used to screen the SCN libraries to obtain longer cDNA clones. Eighteen cDNA clones that mapped to the region on by Southern blot were obtained (these clones are referred to as "C1 through C18" in FIG. 3), and these clones fell into 10 different classes of clones.

C. Shotgun Sequencing of BAC Clones

In addition to the cDNA-identifying approaches described above, random sequencing of genomic DNA were used as a third method of transcription unit analysis. With this approach: 1) a genomic scaffold (i.e., one to two-fold coverage of the region) could be used for sequenced-tagged site (STS) mapping and for finer mapping of cDNAs isolated by the first two techniques (as opposed to mapping by BAC Southern); 2) database searches using genomic sequence could identify cDNAs not found by direct screening and cDNA selection; and 3) genomic sequence would uncover new SSLP markers that could further diminish the region containing Clock Upon further consideration, selected BACs were sequenced to completion. Complete genomic sequence allowed precise mapping of STSs, exon mapping of cDNA clones, promoter analysis, and interpretation of other experiments such as BAC rescue and Southern blot analysis.

Two parametes are critical for successful shotgun sequencing project: extremely pure source DNA and a high-throughput/low-cost template preparation protocol. Two independent shotgun libraries using two BACs, which together covered about ⅔ of the Clock critical region were constructed. BAC DNA was prepared by large-scale alkaline lysis of two-liter liquid cultures followed by a two-step CsCl gradient purification using methods adpated from the C. elegans genome project (Favello et al. 1995). The second CsCl purification of plasmid (BAC) DNA was necessary to ensure low E. coli chromosomal DNA contamination. The protocol typically yielded 5–15 μg intact BAC DNA from two liters of liquid culture. 5 μg DNA were sonicated, blut-ended, and run on an agarose gel for size selection of insert DNA. The 1.3–1.7 kb range was gel-purified and blut-end ligated into M13. Ligation products were electroporated into E. coli XL1 Blue MRF' and plated; 25-fold dilution of the ligation mixture was necessary to prevent arcing during electroporation. Clear plaques were picked into SM buffer for storage.

High-throughput M13 template preparation was essential for efficient BAC sequencing. Probability theory indicates that 4× coverage of a length of DNA is necessary to achieve 98% of the complete sequenc. The number of templates needed to achive "n"X coverage is defined as $$\frac{n^* \text{ total length of DNA}}{\text{sequenced length per template}}$$

Knowing the length of the BAC DNAs (160 kb and 140 kb) and assuming 500 bases of good sequence per template, 1280 templates and 1120 templates, respectively, were needed to reach 4× coverage of each library. A magnetic bead isolation protocool adapted form Hawkins et al. (1994) in a 96-tube format was used to rapidly prepare sequence-ready M13 template. 650 μl M13 cultures were grown in 96-tube racks. Cultures were centrifuged, lysated were transferred to new tubes, and DNA was released by heat/detergent lysis of M13 protein coats. Magnetic beads and hybridization solution (2× stock: 26% PEG 8000, 20 mM $MgC_{12}$) were added to the tubes for selective DNA hybridization to the beads. The beads were magnetically collected and supernatant was discarded. DNA was eluted with water; the beads were magnetically collected, and the DNA was transferred to a 96-well plate for storage. This protocol typically yielded 1–2 μg sequencing template per sample; 192 templates could be prepared in about 5 hours. Fluorescence cycle sequencing was performed by an ABI PRISM Turbo 800 Molecular Biology LabStation with −21 M13 Dye Primer chemistry, and the products were run on an ABI PRISM 377 DNA sequencer. The Sequencher program (Gene Codes) removed vector sequence and low-quality sequence from each shotgun sequence and then aligned the sequences into contigs. Average sequence length was 580 bases. Each sequence was used to search BLAST databases (BLASTN-nr, BLASTN-dbEST, BLASTX-nr, and TBLASTX-dbEST) to identify Clock candidates by gene, EST, or protein homology. In addition, various gene finding programs were also used.

The 160 kb BAC was sequenced to 4× coverage and aligned into about 20 contigs of 4–30 kb each. Clones that defined the ends of contigs were. selected for "reverse sequencing", where the opposite end of the 1.5 kb inserts was sequenced by M13 Reverse Dye Primer chemistry in an attempt to join contigs. This approach reduced the number of contigs to 12, and more importantly, it provided enough information to order all contigs by STS alignment. The 140 kb BAC has been sequenced to 3× coverage so far, and its region overlapping the 160 kb BAC provided sufficient information to reduce the number of contigs in the latter to five. Extensive sequencing of these two BACs in the Clock critical region has proven to be extremely informative: all cDNAs isolated by direct screening and by cDNA selection were physically mapped, and additional Clock candidates identified by sequence homology (designated S1 through S12 in FIG. 3). The genomic sequence provides critical information for analysis of transcription units (such as identification of exon boundaries), interpretation of BAC rescue experiments, and Clock mutation identification and analysis.

EXAMPLE 6

Transgenic Mouse Expression of BAC Clone and Phenotypic Rescue of Clock

Because the mutation was a point mutation induced by ENU, a second parallel approach using transgenic rescue to clone the Clock gene was undertaken. Transgenic mice were made by injecting BAC DNA from the clones that mapped to the Clock region. Three sets of DNA preparations were used: 1) circular full-length BAC 54 (140 kb); 2) linear NotI fragment of BAC54 (100 kb); and 3) circular full-length BAC 52 (the clone that overlaps with BAC 54 by ~90 kb. Circular DNA was purified using alkaline lysis and cesium chloride gradient ultracentrifugation protocol described for the cosmid DNA purification with some modifications (Favello et al. 1995). The 100 kb linear NotI fragment of BAC 54 was gel-purified using pulse-field gel electrophoresis.

Figure 4A:
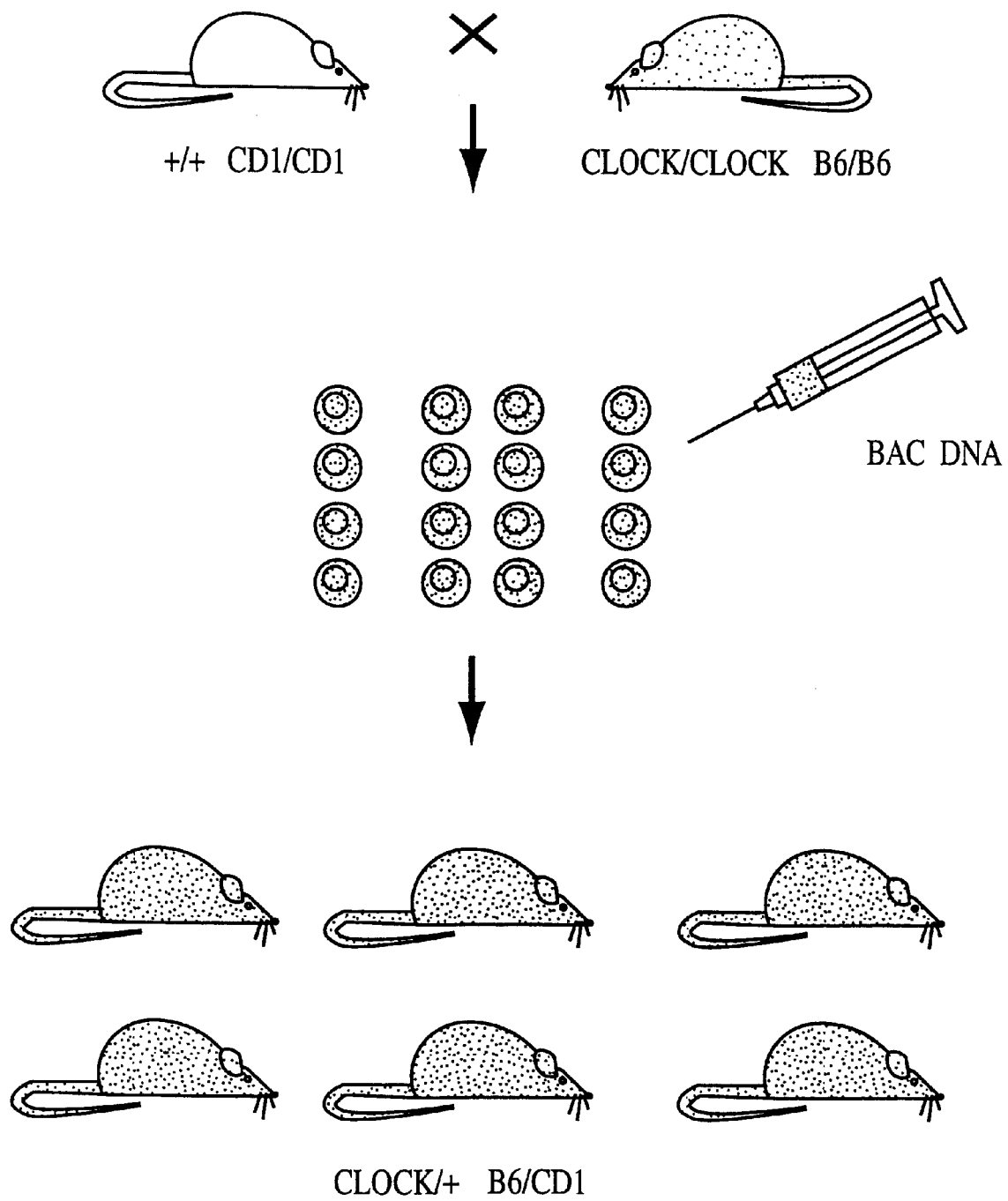
FIG. 4 is a schematic illustration of the breeding strategy used to produce and rescue Clock mutants.
Figure 4B:
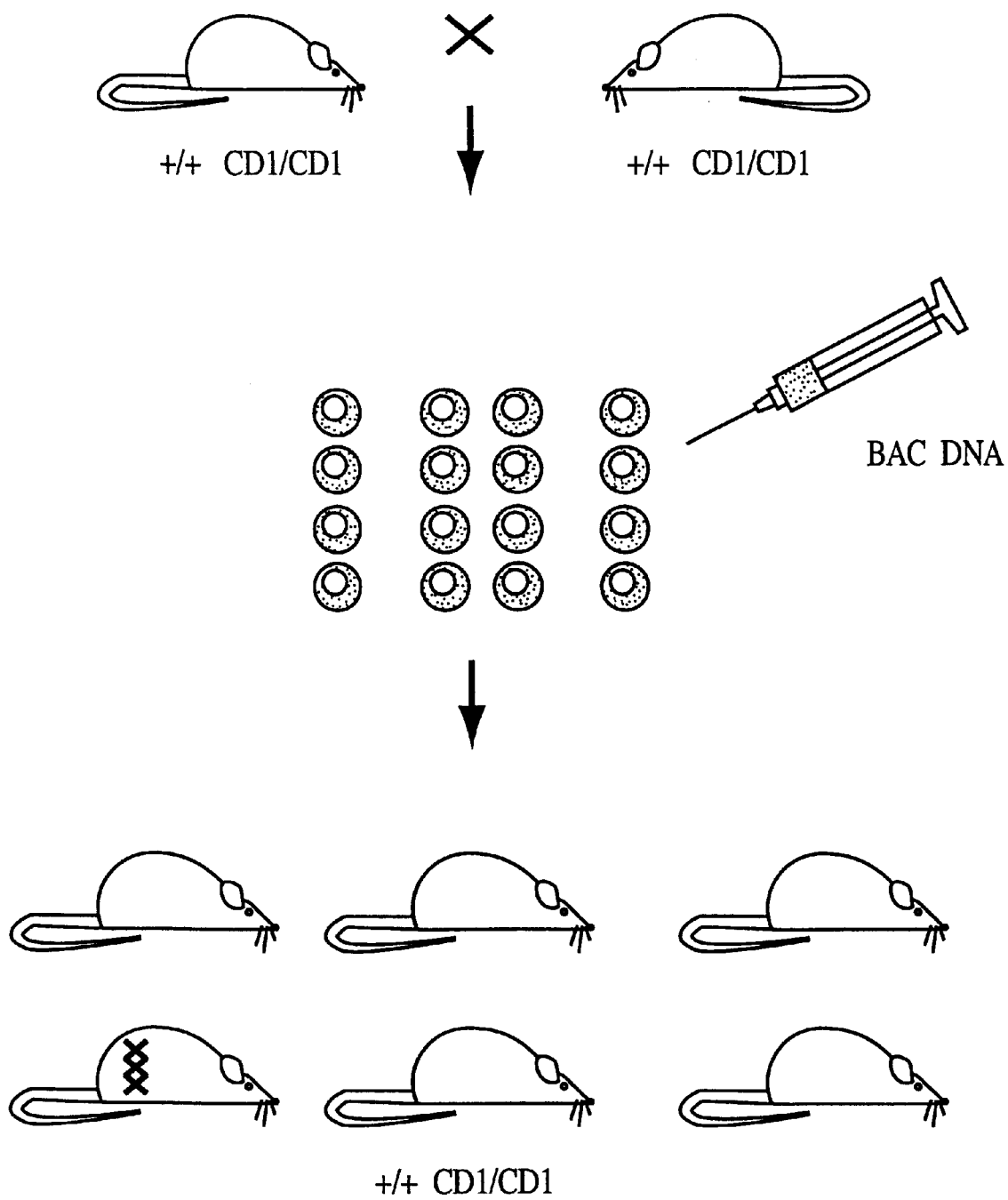

Isolated BAC DNA was injected at a concentration of 1 μg /μl into fertilized mouse oocytes isolated from crosses between either CD1 +/+ females and (BALB/cJ X C57BL/6J) F2 Clock/Clock males or CD +/+ females and CD1 +/+ males as described previously (See FIG. 4) (Hogan et al. 1994). Transgenic mice were identified both by PCR and Southern blot analysis of the genomic DNA prepared from tall biopsies as described (Hogan et al. 1994). Out of 64 mice born from the BAC 54 injected embryos, 6 were positive for the transgene by both methods. Four mice out of 54 were positive for the 100 kb linear fragment of BAC 54, and 2 out of 12 born were positive for BAC 52 DNA ( See Table 2).

TABLE 2

Summary of BAC Transgenic Mice Lines

| Transgenic line | Founder genotype | DNA injected | Transgene copy number | Transmittance |
| --- | --- | --- | --- | --- |
| TG14 | Clock/+ | BAC54 circular DNA, 140 kb | 2–3 | 50% |
| TG36 | Clock/+ | BAC54 circular DNA circular k-b | 3–4 | 50% |
| TG55 | +/+ | BAC54 circular DNA circular k-b | 8–10 | 50% |
| TG60 | +/30 | BAC54 circular DNA, 140 kb | 1 | 50% |
| TG19 | +/+ | BAC54 circular DNA, 140 kb | N/D | 50% |
| TG48 | Clock/+ | BAC54 circular DNA, 140 kb | N/D | 13% |
| TG80 | +/+ | BAC54 100 kb linear Not1 - fragment | 2–3 | 50% |
| TG97 | | BAC54 100 kb linear Not I - fragment | 10–12 | 50% |
| TG98 | +/+ | BAC54 100 kb linear Not1 - fragment | ND | 50% |
| TG91 | Clock/4 | BAC54 100 kb linear Not1 - fragment | ND | 10% |
| TG121 | Clock/+ | BAC52 circular DNA, 160 kb | 1 | 50% |
| TG126 | Clock/+ | BAC52 circular DNA, 160 kb | 4–5 | 50% |

Mice postive for the transgene integration by both methods were crossed to either Clockl+ females (for male founders ) or Clock/Clock males (for female founders ). F1 progeny from these crosses were 1) tested for the presence of the transgene, 2) genotyped for Clock locus by flanking SSLP markers, and 3) wheel-tested for circadian phenotype as described previously (Vitaterna et al. 1994). Results of the phenotypic assay are summarized in Table 3. Circadian period length from each mouse was calculated for the 20-day interval during the exposure to constant darkness by a $Chi^2$ periodogram analysis.

Figure 5:
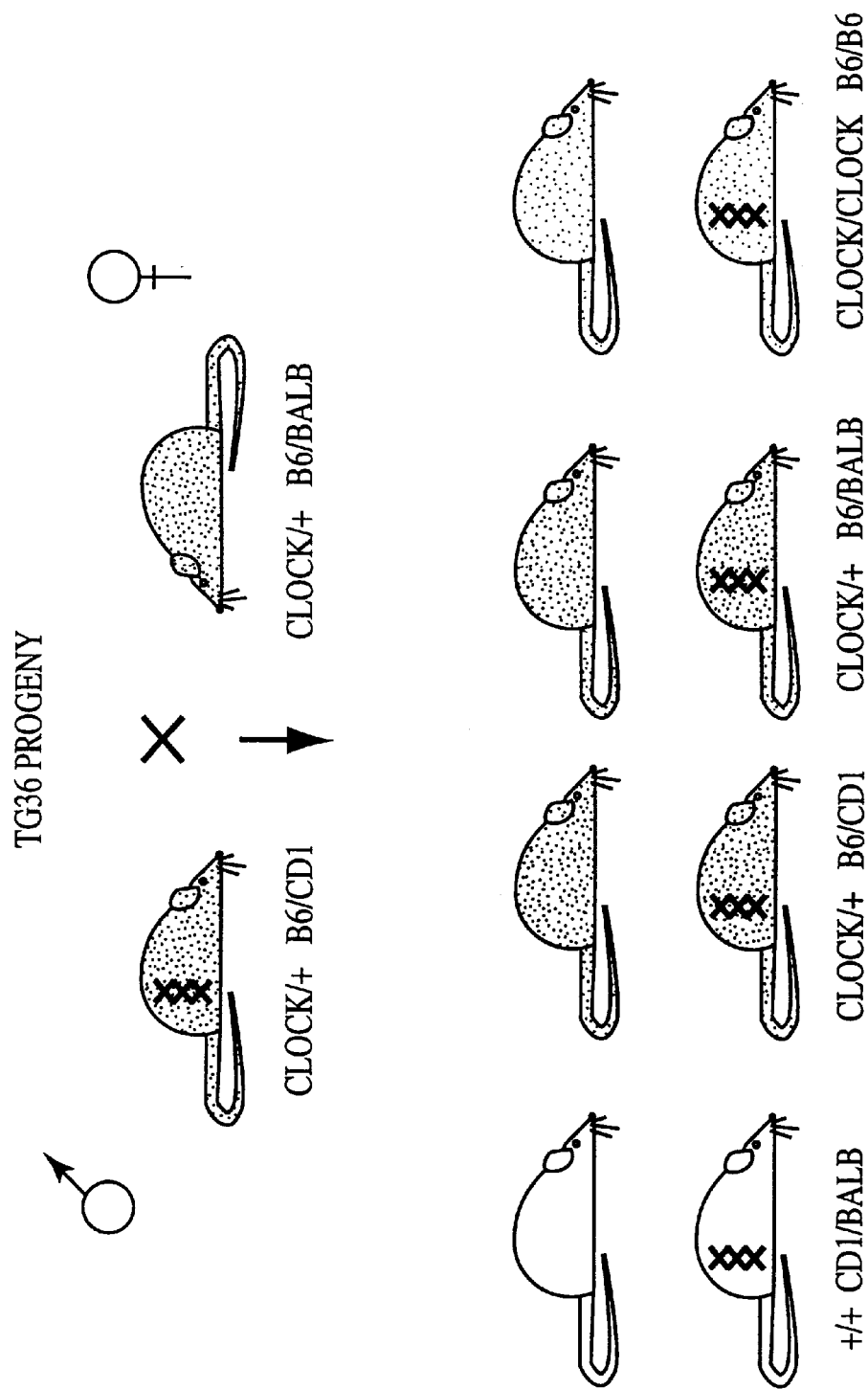
FIG. 5 is a schematic illustration of the breeding strategy used to produce TG36 progeny.

Four lines generated from BAC 54 injections (TG14, 36, 55, 60) showed complete rescue of the Clock mutant phenotype both in heterozygous and homozygous Clock mutant animals. An example is provided for line TG36 which is representative of this group. The breeding scheme used in the experiment in shown in FIG. 5. Activity records showed the phenotypic rescue with BAC 54 transgene in Clock homozygotes. As described above, the Clock mutation has been shown to lengthen circadian period by 1 hr in heterozygotes and by 4 hr in homozygotes. All transgenic animals that were genotyped as Clock/+ or Clock/Clock from these four lines showed a circadian period similar to wild type (Table 3). This result demonstrates that the Clock gene is localized within the 140 kb BAC clone.

To reduce this interval to a single gene, the transgenic functional assay was performed with a smaller DNA fragment (BAC 54 100 kb linear fragment) and an overlapping BAC clone (160 kb BAC 52 clone). Both of these genomic fragments failed to rescue the Clock mutation (Table 3).

the day and low levels at night. This rhythm in Clock mRNA is consistent with the presence of circadian oscillators in both of these tissues (i.e., the suprachiasmatic nucleus and retina). In situ hybridization revealed that the expression of Clock mRNA is enriched in the SCN with lower levels in other regions of the brain. Taken together the reduced mRNA expression in Clock mutants, the diurnal rhythm in mRNA abundance in the hypothalamus and the eye, and the enrichment of mRNA expression in the SCN all strongly suggested that this candidate gene encoded Clock. No other candidate genes revealed any changes in mRNA expression on Northern blots. This led to further analysis of this PAS domain candidate gene including the elucidation of the entire gene, analysis and the exon-intron structure of the gene, sequencing of cDNA clones expressed from the gene, identification of coding sequence of cDNA clones expressed from the gene, identification of the coding sequence and deduced amino acid sequence of the CLOCK protein.

Figure 6:
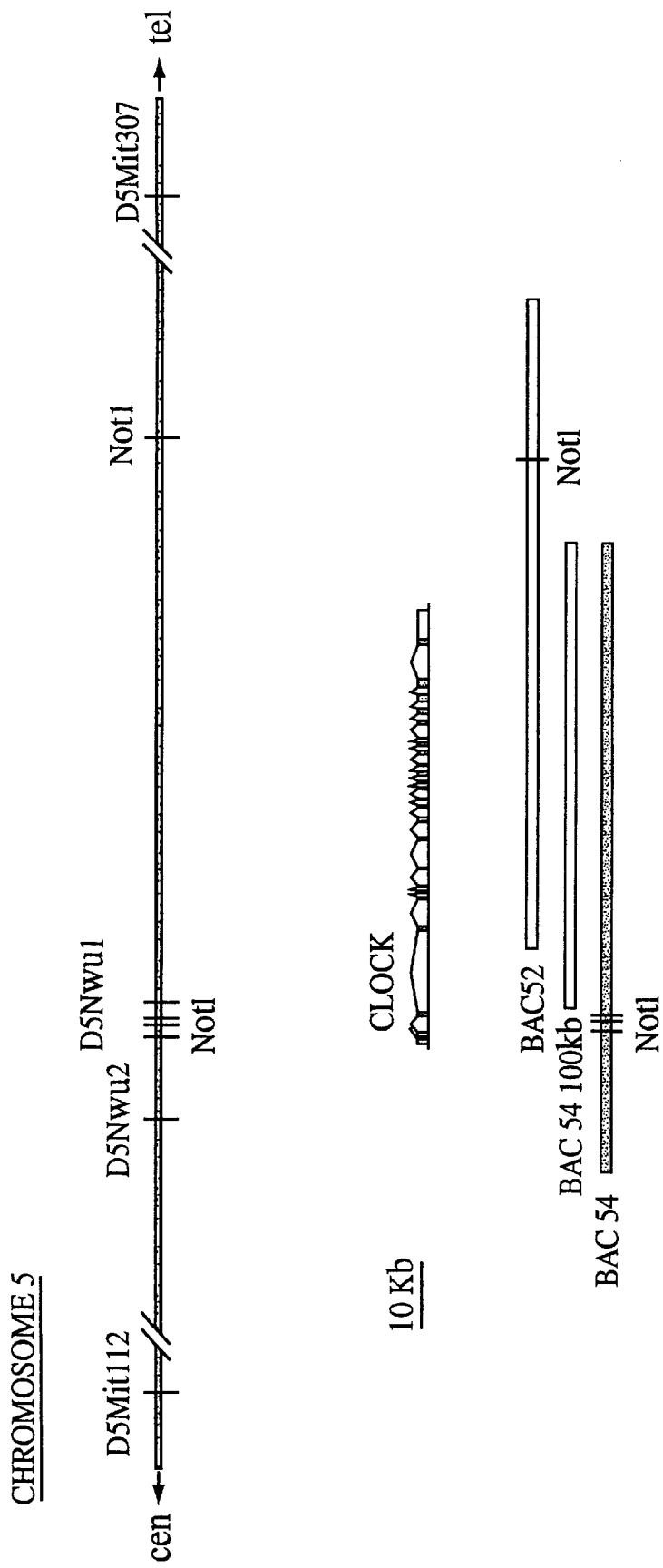
FIG. 6 is a schematic illustration of the physical location of the Clock gene.

FIG. 6 shows a diagram of the physical extent and location of the Clock gene. Based on a set of 10 classes of cDNA clones from the gene, the transcribed region of the Clock gene spans over 90 kb of genomic sequence and 5 contains 24 exons. Two of the exons (exons 1A and 1B) are distal to the NotI site in BAC 54, and thus the 100 kb fragment from BAC 54 and 160 kb clone of BAC 52 do not contain the 5' region of the Clock gene. Because of its

| Trasgenic Line | +/+ | ++/tg | Clock/+ | Clock/+ tg | Clock/Clock | Clock/Clock tg |
|---|---|---|---|---|---|---|
| TG14 | N/A | N/A | 24.22 ± 0.183 n = 5 | 23.08 ± 0.146 n = 7 | 27.06 ± 0.314 n = 7 | 23.27 ± 0.099 n = 9 |
| TG36 | 23.48 ± 0.048 n = 11 | 22.89 ± 0.05 n = 10 | 24.18 ± 0.053 n = 20 | 23.21 ± 0.047 n = 20 | 27.36 ± 0.282 n = 8 | 23.18 ± 0.082 n = 14 |
| TG55 | 23.41 ± 0.091 n = 10 | 22.92 ± 0.137 n = 8 | 24.12 ± 0.21 n = 8 | 22.77 ± 0.099 n = 7 | N/A | N/A |
| TG60 | N/A | N/A | 23.91 ± 0.1 n = 13 | 23.13 ± 0.122 n = 6 | N/A | N/A |
| TG80 | 23.44 ± 0.101 n = 18 | 23.50 ± 0.07 n = 5 | 23.92 ± 0.125 n = 19 | 23.64 ± 0.083 n = 4 | N/A | N/A |
| TG97 | N/A | N/A | 23.93 ± 0.04 n = 4 | 26.67 ± 0.065 n = 7 | N/A | N/A |
| TG121 | 23.50 ± 0.142 n = 4 | 23.66 ± 0.125 n = 2 | 23.99 ± 0.11 n = 13 | 23.96 ± 0.032 n = 5 | 26.83 ± 0.4 n = 2 | 26.87 ± 0.161 n = 4 |

Taken together, the results from all of these transgenic rescue experiments are consistent with only a single gene in the 140 kb BAC clone which we describe below.

EXAMPLE 7 mRNA Expression, Sequence and Structure of the Clock Gene

The mRNA expression of candidate genes was screened by Northern analysis in Clock mutant vs. wild-type mice. This led to the observation of reduced mRNA expression of a candidate M13 clone with a PAS domain sequence first recognized by shotgun sequencing. This M13 genomic clone contained exons from a transcription unit that we subsequently identified as the Clock gene. There are two major transcripts from the Clock locus of ~8 and ~11 kb (using the cDNA clones, YZ50 or YZ54, as a probe on Northern blots). There was a reduction in the abundance of both transcripts in the hypothalamus and eye of homozygous Clock mutants as compared to wild type mice. In addition, there was also a diurnal rhythm in the level of Clock mRNA in wild-type mice in both the hypothalamus and eye with high levels in substantial size, the Clock gene is the only transcription unit in BAC 54 that can account for the results of the transgenic rescue experiments. Based upon the physical location of this gene and the rescue experiments, we can conclude that this candidate gene encodes Clock.

Figure 7:
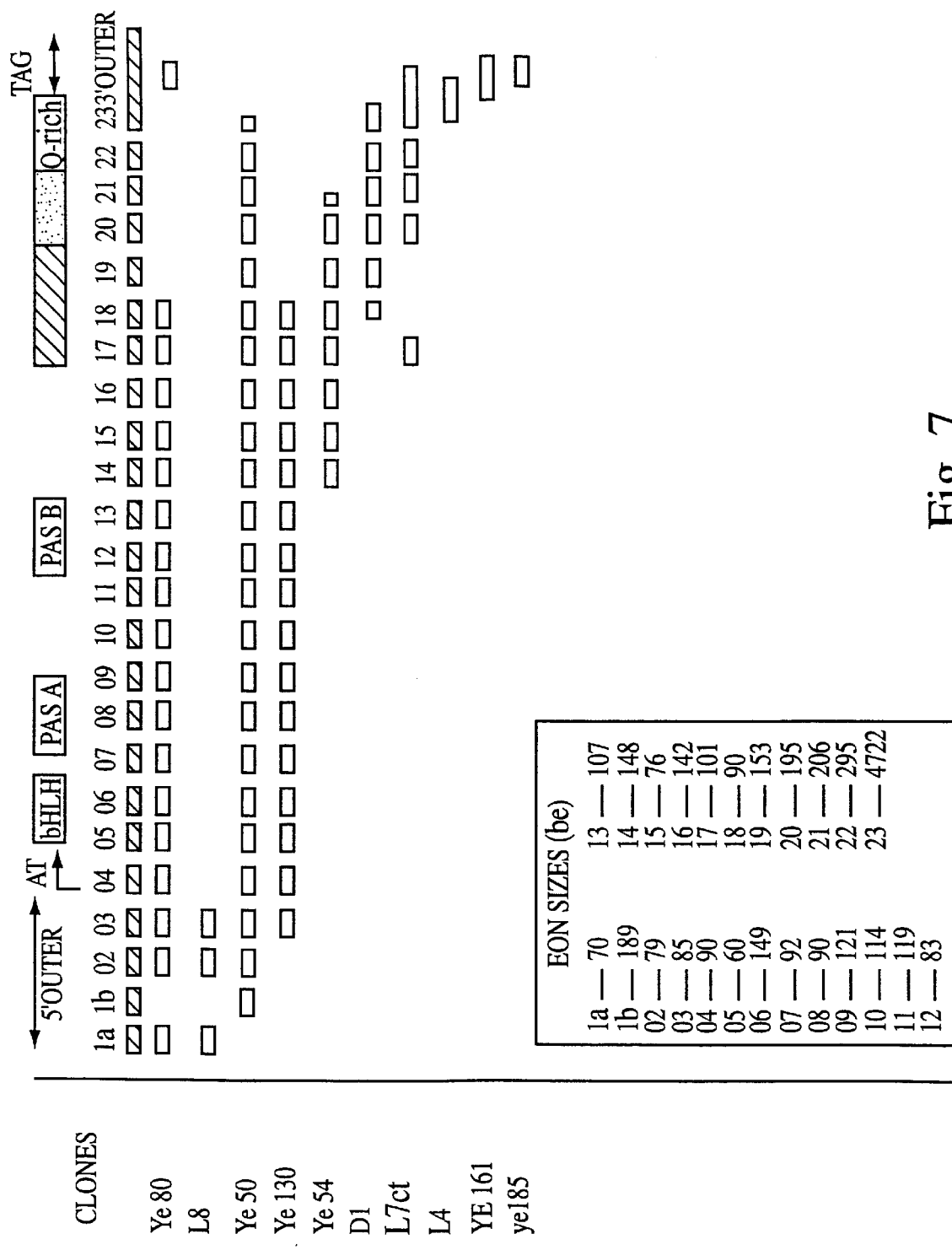
FIG. 7 shows the exon structure of the Clock gene and the exon content of different cDNA clones

The exon structure of Clock is shown in FIG. 7. Ten classes of cDNA clones have been found. There is alternative use of exons 1A and 1B in clones YZ50, L8 and YZ80. In addition there is alternative splicing of exons 18 which can be seen in clone L7c, which also has a deletion of exon 19 caused by the Clock mutation (described below)

The complete nucleotide sequence of Clock based upon genomic exon sequences is shown in FIGS. 8A–8M. The sequences of individual exons are shown in FIGS. 9A–9Z. The splice donor and acceptor site sequences are shown for the intron/exon boundaries in FIG. 10. There is an open reading frame of 2568 base pairs between nucleotides 389 and 2953 which encodes a 855 amino acid conceptually translated protein (called CLOCK). Following the coding sequence, which terminates with a TAG codon in Exon 23, there is a very long 3' untranslated sequence that terminates at ~7500 bp (defined by a subset of cDNA clones with poly A tails at this location), and additional 3' untranslated sequence that continues for another ~2500 bp to form a second transcript of ~10 kb. The 7.5 kb and 10 kb transcripts based on cDNA and genomic sequence correspond well with the ~8 kb and ~11 kb mRNA transcripts estimated from Northern blots.

The Clock gene encodes a member of the basic helix-loop-helix (bHLH) ~PAS domain family of proteins. A search of the NCBI database using BLASTN shows that the Clock nucleotide sequence is most similar to human MOP4 (68% identical), human N-PAS2 (69% identical) and mouse NPAS2 (67% identical). A search of the NCBI database with the conceptually translated protein sequence using BLASTX shows a similarity to these same three proteins as well as weaker similarity with a large number of bHLH-PAS proteins. An amino acid alignment of CLOCK with human NPAS2 and mouse NPAS2 is shown in FIG. 11. There is sequence similarity among the three proteins in the basic helix-loop-helix domain as well as the entire PAS domain. In addition, there are serine-rich and glutamine-rich regions that are well conserved in the midportion and C-terminal region of the proteins. Unlike NPAS2, however, CLOCK has a poly-glutamine stretch near the C-terminus.

In the sequence of the mutant Clock allele, there is a single nucleotide base substitution from A to T that alters the third position of the 5' (donor) splice site of exon 19. This changes the consensus sequence at this splice site from gt a to gtt, which is known in the art to cause exon skipping (Krawczak, M., J. Reiss, D. N. Cooper, *Human Genetics* 90:41–54, 1992). As shown in FIG. 10, 20 out of 22 donor splice sites in the Clock gene have the consensus sequence gta and the remaining 2 sites are gtg, which is also consistent with a purine at the third position, The A to T point mutation in the mutant Clock allele is consistent with that expected from an ENU-induced mutation (Provost and Short, 1994). In the case of Clock, this leads to a deletion of exon 19. The deletion of exon 19 causes a deletion of 51 amino acids (corresponding to amino acids numbers 514 to 564 in SEQ ID NO: 2). FIG. 12 shows the amino acid sequence of CLOCK with the bHLH, PAS-A and PAS-B domains as well as the deletion in the mutant. FIG. 13 shows the exon 18 alternatively spliced version of a Clock, which leads to removal of 30 amino acids (corresponding to amino acids numbers 484 to 513 in SEQ ID NO: 2). Both the wild-type and mutant versions of the ClockmRNA and protein, express an isoform missing exon 18. Thus, at least 4 different coding versions of CLOCK have been identified.

The deduced amino acid sequence of the Clock gene product provides insights about its function as a transcription factor. The basic region of the bHLH domain is known to mediate DNA binding and shows that CLOCK likely interacts directly with DNA. The HLH and PAS domains are each known to be protein dimenization domains and predict that CLOCK can interact directly either with itself or with other bHLH or PAS proteins. The C-terminal region of CLOCK has a number of glutamine-rich, proline-rich and serine-rich stretches that are characteristic of activation domain transcription factors.

EXAMPLE 8

Human Clock Gene And Gene Product

The Clock gene regulates circadian rhythms in mice. To date, it is the only known gene with this function that has been isolated at the molecular level in a mammal. Here, we describe how we cloned the human homologue of Clock, and we disclose both the nucleotide sequence of its coding and 5' untranslated regions as well as the deduced amino acid sequence of its protein product. To achieve these ends we pursued in parallel two strategies: we sequenced several human clones identified by end-sequence in the NCBI database, and we screened a human cDNA library to isolate novel clones that hybridized with a probe of the mouse Clock gene.

In the course of our studies of Clock we had searched the NCBI nucleotide database and identified 4 cDNA clones (150328, 328936, 754816, 768552) whose expressed sequence tags (ESTs) indicated they were likely human homologues of the Clock gene. We obtained these clones from their distributor (Research Genetics, Huntsville, Ala.) and sequenced them. DNA sequence alignments to the mouse Clock transcript indicated that the clones fell into three classes that extended discontinuously from the middle of gene's open reading frame to its 3' end and untranslated region.

Simultaneously, we screened $10^6$ clones from a commercially prepared library (Clontech) of human hypothalamic cDNAs contained the lambda gt 10 vector. The library is both oligo dT and random primed with insert sizes that range from 0.8 to 4 kb around a mean of 1.7 kb. The protocol for the screen was as follows: we random primed probe (DECAprime II, Ambion) from a phagemid clone of mouse Clock (YZ 50) cut with Sac 1 and Not 1 restriction endonucleases (NEB); we prehybridized filters for 8 hours in a buffer solution containing 6×SSC, 2×Denhardt's solution, 1 mM EDTA, 0.5% SDS, and 150 g/ml of boiled sheared salmon sperm; and then hybridized the filters for a further 24 hours at 55 C. in fresh hybridization solution with added probe. Following hybridization we washed the filters twice for 30 minutes at room temperature in a solution of 2×SSC/ 0.1% SDS; and then performed successive washes for 30 minutes each at 55 C. in solutions of 2×SSC/0.1% SDS, 1×SSC/0.1% SDS, and 0.5×SSC/0.1% SDS. With this treatment we identified on the initial round of screening 43 plaques that generated hybridization signals. We picked and plaque purified 24 of these, and then for 13 of the 24 prepared vector DNA from phage lysate. With sequencing primers flanking the vector's cloning site, we sequenced the inserts of these clones in fluorescent dye terminator reactions run on an ABI PRISM 377 DNA sequencer. DNA sequence alignments to the mouse Clock transcript, as well as database searches with the BLASTN algorithm, revealed that all 13 clones were derived from the human homologue of the Clock gene. We subsequently subcloned a subset of these clones into a pBluescript plasmid vector and re-confirmed their identify by sequence analysis.

Further DNA sequence alignments to the transcript of the mouse Clock gene revealed that the consensus sequence from the aggregate of the existing EST and hypothalamic clones extended through the gene's entire coding region and into much of its flanking 5' and 3' untranslated ends (FIG. 16). FIG. 14 records 3546 nucleotides of the sequence of the human Clock gene: the open reading frame extends for 2538 base pairs between nucleotides 418 and 2955 and is about 89% identical to the mouse orthologue. It encodes the conceptually translated protein, CLOCK, of 846 amino acids. FIG. 14 records the deduced amino acid sequence of the gene: CLOCK is 96% identical to its mouse orthologue and it retains all the domains that originally suggested its molecular function in the mouse: HLH and PAS protein dimerization domains; a basic region adjacent to the helix loop helix domain known to mediate DNA binding; and a characteristic glutamine rich region in the C terminus, indicating that CLOCK, in humans as in mice, is likely a transcription factor (FIG. 15).

Our successful effort to isolate this the first known human circadian gene promises to provide insight into the molecular and genetic basis of normative circadian physiology. More immediately, however, the human Clock gene will become a timely candidate for the genetic analysis of the circadian pathophysiology implicated in disorders of sleep, affect, and endocrinology.

The disclosures listed below and all other disclosures cited herein are incorporated into the specification by reference.

Altschul, S. F., W. Gish, W. Miller, E. W. Myers, D. J. Lipman. 1990. Basic Local Alignment Search Tool. *J Mol. Biol.* 215:403–410

Aronson, B. D., K. A. Johnson, J. J. Loros, J. C. Dunlap. 1994. Negative feedback defining a circadian clock: autoregulation in the clock gene frequency. *Science* 263:1578–1584

Baylies, M. K., T. A. Bargiello, F. R. Jackson, M. W. Young. 1987. Changes in the abundance and structure of the per gene product can alter periodicity of the Drosophila clock. *Nature* 326:390–392

Burbach, K. M., A. Poland, C. A. Bradfield. 1992. Cloning of the Ah-receptor cDNA reveals a distinctive ligand-activated transcription factor. *Proc. Natl. Acad. Sci. USA* 89:8185–8189

Crosthwaite, S. K., J. J. Loros, D. J. C. 1995. Light-induced resetting of a circadian clock is mediated by a rapid increase infrequency transcript. *Cell* 81:1003–1012

Dunlap, J. C. 1993. Genetic analysis of circadian clocks. *Annu. Rev. PhysioL* 55:683–729

Edery, I., J. E. Rutila, M. Rosbash. 1994a. Phase shifting of the circadian clock by induction of the Drosophila period protein. *Science* 263:237–240

Edery, I., L. J. Zwiebel, M. E. Dembinska, M. Rosbash. 1994b. Temporal phosphorylation of the Drosophila period protein. *Proc. Natl. Acad. Sci. USA* 91:2260–2264

Favello, A., L. Hillier, R. K. Wilson. 1995. Genomic DNA sequencing methods. In *Methods in Cell Biology*, eds. HF Epstein, DC Shakes, pp. 551–569. San Diego: Academic Press.

Feldman, J. F. 1982. Genetic approaches to circadian clocks. *Ann. Rev. Plant PhysioL* 33:583–608

Feldman, J. F., M. N. Hoyle. 1973. Isolation of circadian clock mutants of Neurospora crassa. *Genetics* 75:605–613

Fields, S., O.-K. Song. 1989. A novel genetic system to detect protein-protein interactions. *Nature* 340:245–246

Geissler, E. N., M. A. Ryan, D. E. Housman. 1988b. The dominant-white spotting (W) locus of the mouse encodes the c-kit proto-oncogene. *Cell* 55:185–192

Gekakis, N., L. Saez, A.-M. Delahaye-Brown, M. P. Myers, A. Sehgal, M. W. Young, C. J. Weitz. 1995. Isolation of timeless by PER protein interaction: Defective interaction between timeless protein and long-period mutant PER$^L$. *Science* 270:811–815

Hall, J. C. 1990. Genetics of circadian rhythms. *Annu. Rev. Genet.* 24:659–697

Hall, J. C., C. P. Kyriacou. 1990. Genetics of biological rhythms in Drosophila. *Adv. Insect PhysioL* 22:221–297

Hardin, P. E., J. C. Hall, M. Rosbash. 1990. Feedback of the Drosophila period gene product on circadian cycling of its messenger RNA levels. *Nature* 343:536–540

Hardin, P. E., J. C. Hall, M. Rosbash. 1992. Circadian oscillations in period gene mRNA levels are transcriptionally regulated. *Proc. Natl. Acad. Sci. USA* 89:11711–11715

Hoffman, E. C., H. Reyes, F.-F. Chu, F. Sader, L. H. Conley, B. A. Brooks, O. Hankinson. 1991. Cloning of a factor required for activity of the Ah (dioxin) receptor. *Science* 252:954–958

Hogan, B., R. Beddington, F. Constantini, E. Lacey. 1994. *Manipulating the Mouse Embryo, A Laboratory Manual.* Plainview, N.Y.: Cold Spring Harbor Laboratory Press. pp.

Huang, Z. J., I. Edery, M. Rosbash. 1993. PAS is a dimerization domain common to Drosophila Period and several transcription factors. *Nature* 364:259–262

Hunter-Ensor, M., A. Ousley, A. Sehgal. 1996. Regulation of the Drosophila protein timeless suggests a mechanism for resetting the circadian clock by light. *Cell* 84:677–685

Konopka, R. J., S. Benzer. 1971. Clock mutants of Drosophila melanogaster. *Proc. Natl. Acad. Sci. USA* 68:2112–2116

Krumlauf, R. 1993. Hox genes and pattern formation in the branchial region of the vertebrate head. *Trends Genet.* 9:106–112

Kusumi, K., J. S. Smith, J. A. Segre, D. S. Koos, E. S. Lander. 1993. Construction of a large-insert yeast artificial chromosome library of the mouse genome. *Mammalian Genome* 4:391–392

Lee, C., V. Parikh, T. Itsukaichi, K. Bae, I. Edery. 1996. Resetting the Drosophila clock by photic regulation of PER and a PER-TIM complex. *Science* 271:1740–1744

Lisitsyn, N., N. Lisitsyn, M. Wigler. 1993. Cloning the differences between two complex genomes. *Science* 259:946–951

Liu, X., L. J. Zwiebel, D. Hinton, S. Benzer, J. C. Hall, M. Rosbash. 1992. The period gene encodes a predominantly nuclear protein in adult Drosophila. *J Neurosci.* 12:2735–2744

Lovett, M. 1994. Fishing for complements: finding genes by direct selection. *Trends in Genetics* 10:352–357

Lynch, G. R., C. B. Lynch. 1992. Using quantitative genetic methods to understand mammalian circadian behavior and photoperiodism. In *Techniques for the Genetic Analysis of Brain and Behavior*, eds. D Goldowitz, D Wahlsten, R E Wimer, pp. 251–268. New York: Elsevier.

Lyon, M. F., P. H. Glenister, J. F. Loutit, E. P. Evans, J. Peters. 1984. A presumed deletion covering the Wand Ph loci of the mouse. *Genetical Research* 44:161–168

Marchuk, D. A., F. S. Collins. 1994. The use if YACs to identify expressed sequences: cDNA screening using total YAC insert. In *YAC Libraries: A User's Guide*, eds. D L Nelson, B H Brownstein, pp. 113–126. New York: W. H. Freeman and Co.

Matsui, M., Y. Mitsui, N. Ishida. 1993. Circadian regulation of per repeat mRNA in the suprachiasmatic nucleus of rat brain. *Neurosci. Lett.* 163:189–192

McClung, C. R., B. A. Fox, J. C. Dunlap. 1989. The Neurospora clock gene frequency shares a sequence element with the Drosophila clock gene period. *Nature* 339:558–562

Muller, H. J. 1932. *Further studies on the nature and causes of gene mutations*. Sixth International Congress of Genetics, Ithaca, N.Y., Brooklyn Botanic Gardens.

Myers, M. P., K. Wager-Smith, A. Rothenfluh-Hilfiker, M. W. Young. 1996. Light-induced degradation of TIMELESS and entrainment of the Drosophila circadian clock. *Science* 271:17361740

Myers, M. P., K. Wager-Smith, C. S. Wesley, M. W. Young. 1995. Positional cloning and sequence analysis of the Drosophila clock gene, timeless. *Science* 270:805–808

Nambu, J. R., J. O. Lewis, K. A. Wharton Jr., S. T. Crews. 1991. The Drosophila single-minded gene encodes a helix-loop-helix protein that acts as a master regulator of CNS midline development. *Cell* 67:1157–1167

Park, E.-C., H. R. Horvitz. 1986. Mutations with dominant effects on the behavior and morphology of the nematode Caenorhabditis elegans. *Genetics* 113:821–852

Pittendrigh, C. S., S. Daan. 1976. A functional analysis of circadian pacemakers in nocturnal rodents: I. The stability and lability of spontaneous frequency. *J Comp. PhysioL* 106:223–252

Ralph, M. R. 1991. Suprachiasmatic nucleus transplant studies using the tau mutation in golden hamsters. In *Suprachiasmatic Nucleus: The Mind's Clock*, eds. D C Klein, R Y Moore, S M Reppert, pp. 341–348. New York: Oxford University Press.

Ralph, M. R., R. G. Foster, F. C. Davis, M. Menaker. 1990. Transplanted suprachiasmatic nucleus determines circadian period. *Science* 247:975–978

Ralph, M. R., M. N. Lehman. 1991. Transplantation: a new tool in the analysis of the mammalian hypothalamic circadian pacemaker. *Trends Neurosci.* 14:362–366

Ralph, M. R., M. Menaker. 1988. A mutation of the circadian system in golden hamsters. *Science* 241:1225–1227

Reppert, S. M., T. Tsai, A. L. Roca, I. Sauman. 1994. Cloning of a structural and functional homolog of the circadian clock gene period from the giant silkmoth Antheraea pernyi. *Neuron* 13:1167–1176

Rosbash, M., J. C. Hall. 1989. The molecular biology of circadian rhythms. *Neuron* 3:387–398

Schwartz, W. J., P. Zimmerman. 1990. Circadian timekeeping in BALB/c and C57BL/6 inbred mouse strains. *J Neurosci.* 10:3685–3694

Sehgal, A., J. L. Price, B. Man, M. W. Young. 1994. Loss of circadian behavioral rhythms and per RNA oscillations in the Drosophila mutant timeless. *Science* 263:1603–1606

Shin, H.-S., T. A. Bargiello, B. T. Clark, F. R. Jackson, M. W. Young. 1985. An unusual coding sequence from a Drosophila clock gene is conserved in vertebrates. *Nature* 317:445–448

Shizuya, H., B. Birren, U. J. Kim, V. Mancino, T. Slepak, Y. Tachiiri, M. Simon. 1992. Cloning and stable maintenance of 300-kilobase-pair fragments of human DNA in Escherichia coli using an F-factor-based vector. *Proc. Natl. Acad. Sci. USA* 89:8794–8797

Siwicki, K. K., C. Eastman, G. Petersen, M. Rosbash, J. C. Hall. 1988. Antibodies to the period gene product of Drosophila reveal diverse tissue distribution and rhythmic changes in the visual system. *Neuron* 1:141–150

Siwicki, K. K., W. J. Schwartz, J. C. Hall. 1992. An antibody to the Drosophila period protein labels antigens in the suprachiasmatic nucleus of the rat. *J Neurogenetics* 8:33–42

Smith, R. F., R. J. Konopka. 1982. Effects of dosage alterations at the per locus on the period of the circadian clock of Drosophila. *Mol. Gen. Genet.* 185:30–36

Takahashi, J. S. 1995. Molecular neurobiology and genetics of circadian rhythms in mammals. *Annu. Rev. Neurosci.* 18:531–553

Takahashi, J. S., L. H. Pinto, M. H. Vitatema. 1994. Forward and reverse genetic approaches to behavior in the mouse. *Science* 264:1724–1733

Vignau, J., M. Dahlitz, J. Arendt, J. English, J. D. Parkes. 1993. Biological rhythms and sleep disorders in man: The delayed sleep phase syndrome. In *Light and Biological Rhythms in Man*, ed. L Wetterberg, pp. 261–271. Oxford: Pergamon Press.

Vitatema, M. H., D. P. King, A.-M. Chang, J. M. Kornhauser, P. L. Lowrey, J. D. McDonald, W. F. Dove, L. P. Pinto, F. W. Turek, J. S. Takahashi. 1994. Mutagenesis and mapping of a mouse gene, Clock, essential for circadian behavior. *Science* 264:719–725

Vitatema, M. H., D. P. King, A.-M. Chang, J. M. Kornhauser, P. L. Lowrey, J. D. McDonald, W. F. Dove, L. P. Pinto, F. W. Turek, J. S. Takahashi. 1994. Mutagenesis and mapping of a mouse gene, Clock, essential for circadian behavior. *Science* 264:719–725

Vogelbaum, M. A., M. Menaker. 1992. Temporal chimeras produced by hypothalamic transplants. *J Neurosci.* 12:3619–3627

Vosshall, L. B., J. L. Price, A. Sehgal, L. Saez, M. W. Young. 1994. Block in nuclear localization of period protein by a second clock mutation, timeless. *Science* 263:1606–1609

Wehr, T. A., N. E. Rosenthal. 1989. Seasonality and affective illness. *Am. J Psychiatry* 146:829–839

Yu, Q., A. C. Jacquier, Y. Citri, M. Hamblen, J. C. Hall, M. Rosbash. 1987. Molecular mapping of point mutations in the period gene that stop or speed up biological clocks in Drosophila melanogaster. *Proc. Natl. Acad. Sci. USA* 84:784–788

Zeng, H., Z. Qian, M. P. Myers, M. Rosbash. 1996. A light-entrainment mechanism for the Drosophila circadian clock. *Nature* 380:129–135

Zerr, D. M., J. C. Hall, M. Rosbash, K. K. Siwicki. 1990. Circadian fluctuations of period protein immunoreactivity in the CNS and the visual system of Drosophila. *J Neurosci.* 10:2749–2762

Zipursky, S. L., G. M. Rubin. 1994. Determination of neuronal cell fate: Lessons from the R7 neuron of Drosophila. *Annu. Rev. Neurosci.* 17:373–397

1988. *Reproduction, Nutrition and développement*. Paris, Institut National de la Recherche Agronomique, pp Albertsson-Wikland, K. and S. Rosberg. 1988. Analyses of 24-hour growth hormone profiles in children: Relation to growth. *J Clin Endocrinol Metab* 67:

Aldrich, M. S. 1994. Parkinsonism In: Principles and Practice of Sleep Medicine. M H Kryger, T Roth and W C Dement Eds., Philadelphia, W. B. Saunders Co., 783–789.

Arendt, J. 1995. *Melatonin and the Mammalian Pineal Gland*. London, Chapman & Hall, pp 331.

Aschoff, J. 1992. Day-night variations in the cardiovascular system. Historical and other notes by an outsider. In: *Temporal Variations of the Cardiovascular System*. Schmidt/Engel/Blümchen Eds., Berlin Heidelberg, Springer-Verlag, 3–14.

Benca, R. M. 1994. Mood disorders. In: *Principles and Practice of Sleep Medicine*. M H Kryger, T Roth and W C Dement Eds., Philadelphia, W. B. Saunders Co., 899–913.

Benca, R. M. and R. C. Casper. 1994. Sleep in eating disorders. In: *Principles and Practice of Sleep Medicine*. M H Kryger, T Roth and W C Dement Eds., Philadelphia, W. B. Saunders Co., 927–933.

Bliwise, D. L. 1994. Dementia. In: *Principles and Practice of Sleep Medicine*. M H Kryger, T Roth and W C Dement Eds., Philadelphia, W. B. Saunders Co., 790–800.

Borbély, A. A. 1994. Sleep homeostasis and models of sleep regulatoin. In: *Principles and Practice of Sleep Medicine*. M H Kryger, T Roth and W C Dement Eds., Philadelphia, W. B. Saunders Co., 309–320.

Calvo, J. R., M. Rafii-El-Idrissi, D. Pozo and J. M. Guerrero. 1995. Immunomodulatory role of melatonin: Specific binding sites in human and rodent lymphoid cells. *J Pineal Res* 18:119–126.

Card, J. P. and R. Y. Moore. 1991. The organization of visual circuits influencing the circadian activity of suprachiasmatic nucleus. In: *Suprachiasmatic Nucleus: The Mind's Clock*. DC Klein, R Y Moore and S M Reppert Eds., New York, Oxford University Press, 51–76.

Cohen, M. C. and J. E. Muller. 1992. Onset of acute myocardial infarction—circadian variation and triggers. *Cardiovascular Res.* 26:831–838.

Colantonio, D., P. Pasqualetti, R. Casale, P. Desiati, G. Giandomenico and G. Natali. 1989. Atrial natriuretic peptide—renin—aldosterone system in cirrhosis of the liver: Circadian study. *Life Sciences* 45:631–635.

Constantinescu, C. S. 1995. Melanin, Melatonin, melanocyte-stimulating hormone, and the susceptibility to autoimmune demyelination: A rationale for light therapy in multiple sclerosis. *Med Hypotheses* 45:455–458.

de Graaf, C., P. Jas, K. van der Kooy and R. Leenen. 1993. Circadian rhythms of appetite at different stages of a weight loss programme. *Intl J Obesity* 17:521–526.

Decker, K., U. Disque-Kaiser, M. Schreckenberger and S. Reuss. 1995. Demonstration of retinal afferents in the RCS rat, with reference to the retinohypothalamic projection and suprachiasmatic nucleus. *Cell Tissue Res* 282:473–480.

Douglas, N. J. 1994. Control of ventilation during sleep. In: *Principles and Practice of Sleep Medicine*. M H Kryger, T Roth and W C Dement Eds., Philadelphia, W. B. Saunders Co., 204–211.

Edmunds Jr, L. N. 1988. *Cellular and Molecular Bases of Biological Clocks*. New York, Springer-Verlag, pp 497.

Garcia-Pagaán, J. C., F. Feu, A. Castells, A. Luca, H. R. C., F. Rivera, J. Bosch and J. Rodés. 1994. Circadian variations of portal pressure and variceal hemorrhage in patients with cirrhosis. *Hepatology* 19:595–601.

George, C. F. P. 1994. Cardiovascular disease and sleep. In: *Principles and Practice of Sleep Medicine*. M H Kryger, T Roth and W C Dement Eds., Philadelphia, W. B. Saunders Co., 835–846.

Gillis, A. M. and W. W. Flemons. 1994. Cardiac arrhythmias during sleep. In: Principles and Practice of Sleep Medicine. M H Kryger, T Roth and W C Dement Eds., Philadelphia, W. B. Saunders Co., 847–860.

Graeber, R. C. 1994. Jet lag and sleep disruption. In: *Principles and Practice of Sleep Medicine*. M H Kryger, T Roth and W C Dement Eds., Philadelphia, W. B. Saunders Co., 463–470.

Hallonquist, J. D., M. A. Goldberg and J. S. Brandes. 1986. Affective disorders and circadian rhythms. *Can. J. Psychiatry* 31:259–271.

Hartmann, E. 1994. Bruxism. In: *Principles and Practice of Sleep Medicine*. M H Kryger, T Roth and W C Dement Eds., Philadelphia, W. B. Saunders Co., 598–601.

Hineno, T., M. Mizobuchi, K. Hiratani, Y. Inami and Y. Kakimoto. 1992. Disappearance of circadian rhythms in Parkinson's disease model induced by 1-methyl4-phenyl-1,2,3,6-tetrahydropyridine in dogs. Brain Res. 580:92–99.

Hokken-Koelega, A. C. S., W. H. L. Hackeng, T. Stijnen, J. M. Wit, S. M. P. F. de Muinck Keizer-Schrama and S. L. S. Drop. 1990. Twenty-four-hour plasma growth hormone (GH) profiles, urinary GH excretion, and plasma insulin-like growth factor-I and -II levels in prepubertal children with chronic renal insufficiency and severe growth retardation. *J Clin Endocrinol Metab* 71:688–695.

Hyde, T. M., M. F. Egan, R. J. Brown, D. R. Weinberger and J. E. Kleinman. 1995. Diurnal variation in tardive dyskinesia. *Psychiatry Research* 56:53–57.

Jacobshagen, S. and C. H. Johnson. 1994. Circadian rhythms of gene expression in S chlamydomonas reinhardtii: circadian cycling of mRNA abundances of cab II, and possibly of B-tubulin and cytochrome c. *European J Cell BioL* 64:142–152.

Krueger, J. M. and M. L. Karnovsky. 1995. Sleep as a neuroimmune phenomenon: A brief historical perspective. *Adv Neuroimmunol.* 5:5–12.

Kryger, M. H., T. Roth and M. Carskadon. 1994. Circadian Rhythms in Humans: An overview. In: *Principles and Practice of Sleep Medicine*. M H Kryger, T Roth and W C Dement Eds., Philadelphia, W. B. Saunders Co., 301–308.

Kryger, M. H., T. Roth and W. C. Dement. 1994. *Principles and Practice of Sleep Medicine*. Philadelphia, W. B. Saunders Co., pp 1067.

Larsen, K. R., M. T. Dayton and J. G. Moore. 1991. Circadian rhythm in gastric mucosal blood flow in fasting rat stomach. *J surgical Res* 51:275–280.

Larsen, K. R., J. G. Moore, M. T. Dayton and Z. Yu. 1993. Circadian rhythm in aspirin (ASA)-induced injury to the stomach of the fasted rat. Digestive Diseases and *Sciences* 38:1435–1440.

Lausson, S., N. Segond, G. Milhaud and J. F. Staub. 1989. Circadian rhythms of calcitonin gene expression in the rat. *J Endocrinol* 122:527–534.

LaVail, M. M. 1976. Rod outer segment disk shedding in rat retina: Relationship to cyclic lighting. *Science* 194:1071–1074.

Lemmer, B. 1989. Temporal aspects of the effects of cardiovascular active drugs in humans. In: *Chronopharmacology—Cellular and Biochemical Interactions*. B Lemmer Eds., New York, Marcel Dekker, 525–541.

Loros, J. J., S. A. Denome and J. C. Dunlap. 1989. Molecular cloning of genes under control of the circadian clock in Neurospora. *Science* 243:385–388.

Lugaresi, E. and P. Montagna. 1994. Fatal familial insomnia: A new prion disease. In: *Principles and Practice ofSleep Medicine*. M H Kryger, T Roth and W C Dement Eds., Philadelphia, W. B. Saunders Co., 547–548.

Mann, N. P., R. Haddow, L. Stokes, S. Goodley and N. Rutter. 1986. Effect of night and day on preterm infants in a newborn nursery: Randomised trial. *British Med J* 293:1265–1267.

Maron, B. J., J. Kogan, M. A. Proschan, G. M. Hecht and W. C. Roberts. 1994. Circadian variability in the occurrence of sudden cardiac death in ps with hypertrophic cardiomyopathy. *JACC* 23:1405–1409.

Meijer, J. H. 1991. Integration of visual information by the suprachiasmatic nucleus. In: Suprachiasmatic Nucleus: *The Mind's Clock*. D C Klein, RY Moore and S M Reppert Eds., New York, Oxford University Press, 107–119.

Millar, A. J. and S. A. Kay. 1991. Circadian control of cab gene transcription and mRNA accumulation of arabidopsis. The Plant Cell 3:541–550.

Mirmiran, M., J. H. Kok and J. G. Koppe. 1990. Emergence of circadian rhythms in early human development. In: *Sleep*. J Home Eds., Bochum, Pontenagel Press, 26–28.

Monk, T. H. 1990. Shiftworker performance. *Occupational Medicine* 5:183–198.

Monk, T. H. 1994. Shift work. In: *Principles and Practice of Sleep Medicine*. M H Kryger, T Roth and W C Dement Eds., Philadelphia, W. B. Saunders Co., 471–476.

Monk, T. H., J. E. Fookson, M. Moline, L. and C. P. Pollak. 1985. Diurnal variation in mood and performance in a time-isolated environment. *Chronobiol Int.* 2:185–193.

Monk, T. H., E. D. Weitzman, J. E. Fookson and M. L. Moline. 1984. Circadian rhythms in human performance efficiency under free-running conditions. *Chronobiologia* 11:343–354.

Ohta, T. and S. Endo. 1985. Chronobiological comparison of sleep-wake rhythm between chronic schizophrenia and normal control. *Folia Psychiat Neurol Jpn* 39:489–498.

Orem, J. 1994. Respiratory neurons and sleep. In: *Principles and Practice of sleep Medicine*. M H Kryger, T Roth and W C Dement Eds., Philadelphia, W. B. Saunders Co., 177–193.

Orr, W. C. 1994. Gastrointestinal physiology. In: *Principles and Practice of sleep Medicine*. M H Kryger, T Roth and W C Dement Eds., Philadelphia, W. B. Saunders Co., 252–259.

Penev, P. D., P. C. Zee and F. W. Turek. 1997. Serotonin in the spotlight. *Nature* 385:123.

Poirel, C. 1991. Circadian chronobiology of epilepsy: Murine models of seizure susceptibility and theoretical perspectives for neurology. *Chronobiologia* 18:49–69.

Reiter, R. J. and B. K. Follett. 1980. *Progress in Reproductive Biology: Seasonal Reproduction in Higher Vertebrates*. Switzerland, S. Karger, pp Richter, C. P. 1979. *Biological Clocks in Medicine and Psychiatry*. Springfield, Ill., Charles C. Thomas Publisher, pp 111.

Roehrs, T. and T. Roth. 1994. Chronic insomnias associated with circadian rhythm disorders. In: *Principles and Practice of sleep Medicine*. M H Kryger, T Roth and W C Dement Eds., Philadelphia, W. B. Saunders Co., 477481.

Roth, T., T. A. Roehrs, M. A. Carskadon and W. C. Dement. 1994. Daytime sleepiness and alertness. In: *Principles and Practice of sleep Medicine*. M H Kryger, T Roth and W C Dement Eds., Philadelphia, W. B. Saunders Co., 40–49.

Rusak, B. and I. Zucker. 1975. Biological rhythms and animal behavior. *Ann. Rev. Psychol.* 26:137–171.

Sack, R. L., A. J. Lewy, M. L. Blood, L. D. Keith and H. Nakagawa. 1992. Circadian rhythm abnormalities in totally blind people: Incidence and clinical significance. *J Clin Endocrinol Metab* 75:127–134.

Sano, H., H. Hayashi, M. Makino, H. Tadezawa, M. Hirai, H. Saito and S. Ebihara. 1995. Effects of suprachiasmatic lesions on circadian rhythms of blood pressure, heart rate and locomotor activity in the rat. *Jpn Circ J* 59:565–573.

Sapolsky, R. M. 1992. *Stress, The Aging Brain, and the Mechanisms of Neuron Death*. Cambridge, Mass., The MIT Press, pp Smith, L., S. Folkard and C. J. M. Poole. 1994. Increased injuries on night shift. *Lancet* 344:1137–1139.

Spallone, V., L. Bernardi, L. Ricordi, P. Solda, M. R. Maiello, A. Calciati, S. Gambardella, P. Fratino and G. Menzinger. 1993. Relationship between the circadian rhythms of blood pressure and sympathovagal balance in diabetic autonomic neuropathy. *Diabetes* 42:1745–1752.

Taylor, W. C. 1989. Transcriptional regulation by a circadian rhythm. *The Plant Cell* 1:259–264.

Terman, M. 1994. Light treatment. In: *Principles and Practice of Sleep Medicine*. M H Kryger, T Roth and W C Dement Eds., Philadelphia, W. B. Saunders Co., 1012–1029.

Tornatzky, W. and K. A. Miczek. 1993. Long-term impairment of autonomic circadian rhythms after brief intermittent social stress. *Physiol Behav.* 53:983–993.

Turek, F. W. 1994. Circadian rhythms. In: *Recent Progress in Hormone Research*. W Bardin Eds., New York, Academic Press, 43–90.

Turek, F. W., P. Penev, Y. Zhang, O. Van Reeth, J. S. Takahashi and P. Zee. 1995. Alterations in circadian system in advanced age. In: *Ciba Foundation Symposium No 183: Circadian Clocks and Their Adjustment*. J Waterhouse Eds., London, Pitman Press, 212–234.

Turek, F. W. and E. Van Cauter. 1994. Rhythms in Reproduction. In: *Physiology of Reproduction*. E Knobil and J Neill Eds., New York, Raven Press, 487–540.

Turek, F. W. and O. Van Reeth. 1996. Circadian Rhythms. In: *Handbook of Physiology: Chapter 4—Environmental Physiology*. M J Fregly and C M Blatteis Eds., Oxford, Oxford University Press, 1329–1360.

US Congress, O. o. T. A. September, 1991. *Biological Rhythms: Implicationsfor the Worker*. Washington, US Government Printing Office, pp Van Cauter, E. and F. W. Turek. 1986. Depression: a disorder of timekeeping? *Perspect. Biol. Med.* 29:510–519.

Van Cauter, E. and F. W. Turek. 1995. Endocrine and other biological rhythms. In: *Endocrinology*. L J DeGroot Eds., Philadelphia, W. B. Saunders, 2487–2548.

Van Reeth, O., J. Sturis, M. M. Bryne, J. D. Blackman, M. L Hermiite-Baleriaux, R. Leproult, C. Oliner, S. Refetoff, F. W. Turek and E. Van Cauter. 1994. Nocturnal exercise phase-delays the circadian rhythms of melatonin and thyrotropin secretion in normal men. *Am. J Physiol.* 266:E964–E974.

Walker, C. A., C. M. Winget and K. F. A. Soliman. 1981. *Chronopharmacology and Chronotherapeutics*. Tallahassee, Fla., Florida A&M University Foundation, pp 417.

Wehr, T. A. and F. K. Goodwin. 1983. *Circadian rhythms in psychiatry*. Pacific Grove, Calif., Boxwood, pp Wehr, T. A., D. Sack, N. Rosenthal, W. Duncan and J. C. Gillin. 1983. Circadian rhythm disturbances in manic-depressive illness. *Federation Proc.* 42:2809–2814.

Wehr, T. A., A. Wirz-Justice and F. K. Goodwin. 1979. Phase advance of the circadian sleep-wake cycle as an antidepressant. *Science* 206:710–713.

Weltzin, T. E., L. K. G. Hsu, C. Pollice and W. H. Kaye. 1991. Feeding patterns in bulimia nervosa. *Biol, Psychiatry* 30:1093–110.

Wetterberg, L. 1994. Light and biological rhythms. *J Internal Medicine* 235:5–19.

Young, R. W. 1980. The chemistry of the retina: function, renewal, rhythms, and the nucelus. *Neurochemistry* 1:123–142.

What is claimed:

1. A polypeptide made by a process comprising transforming a suitable host cell with an expression vector, growing the host cell under conditions wherein the polypeptide is expressed, and isolating the polypeptide therefrom, wherein the expression vector comprises a polynucleotide which encodes a mammalian CLOCK polypeptide.

2. An isolated and purified mammalian CLOCK polypeptide.

3. The polypeptide of claim 2, being a human CLOCK polypeptide.

4. The polypeptide of claim 3, comprising the amino acid sequence of SEQ ID NO:55 from residue number 35 to residue number 846.

5. The polypeptide of claim 3, comprising an amino acid sequence selected from the group consisting of SEQ ID NO: 55 from amino acid residue number 35 to amino acid residue number 846, SEQ ID NO: 55 from amino acid residue number 11 to amino acid residue number 846, SEQ ID NO: 55 from amino acid residue number 10 to amino acid residue number 846, SEQ ID NO:55 from amino acid residue number 2 to amino acid residue number 846, and SEQ ID NO: 55.

6. A pharmaceutical composition comprising the polypeptide of claim 2, together with a physiologically acceptable diluent.

* * * * *

UNITED STATES PATENT AND TRADEMARK OFFICE
CERTIFICATE OF CORRECTION

PATENT NO. : 6,291,429 B1
DATED : September 18, 2001
INVENTOR(S) : Joseph S. Takahashi et al.

It is certified that error appears in the above-identified patent and that said Letters Patent is hereby corrected as shown below:

<u>Title page,</u>
Item [75], Inventors, please correct the spelling of the first named inventor to read:
-- Joseph S. Takahashi --

Item [12], should read:
-- Takahashi et al. --

Signed and Sealed this

First Day of July, 2003

JAMES E. ROGAN
*Director of the United States Patent and Trademark Office*

SEQUENCE LISTING

<160> NUMBER OF SEQ ID NOS: 55

<210> SEQ ID NO 1
<211> LENGTH: 7498
<212> TYPE: DNA
<213> ORGANISM: Mus musculus -continued

<400> SEQUENCE: 1

```
ggggaggagc gcggcggtag cggtgaattt tgagggtgg gtcggggcg cgcactcgcc        60
gccctggtg ctgccggctc ccggagccgt ggcgtgtccc tgctgtcgcc gctcggctgt      120
cgcgagccgc cgcgggcaga gtcccgggcg ggggagggag gaagccggag cctcaggcac     180
gtgaaagaaa agcacaagaa gaaacttta caggcgttgt tgattggact agggcaacga     240
ttcccaaaat caccagcaag agttctgatg gtcagtcaca cagaagacgg ccttgcgtct    300
gtgggtgttg gagactccat tctaaagata taaaagtga aagaggagaa gtacaaatgt    360
ctaccacaag acgaaaacat aatgtgttat ggtgtttacc gtaagctgta gtaaaatgag   420
ctcaattgtt gacagagatg acagtagtat ttttgatgga ttggtggaag aagatgacaa  480
ggacaaagca aaagagtat ctagaaacaa atcagaaaag aaacgtagag atcagttcaa    540
tgtcctcatt aaggagctgg ggtctatgct tcctggtaac gcgagaaaga tggacaagtc  600
tactgttcta cagaagagca ttgattttt gcgcaaacat aaagagacca ctgcacagtc  660
agatgctagt gagattcgac aggactggaa acccacattc cttagtaatg aagagttta   720
acagttaatg ttagaggctc ttgatggttt ttttttagcg atcatgacag atggaagtat  780
aatatatgta tctgagagtg taacttcgtt acttgaacat ttaccatctg atcttgtgga  840
tcaaagtata tttaattta tcccagaggg agaacattca gaggtttata agatactctc   900
tactcatctg ctggaaagtg actcattaac ccctgagtac ttaaaatcaa aaatcagtt   960
agaattctgt tgtcacatgc ttcgaggaac aatagaccca aaggagccat ccacctatga 1020
atatgtgaga tttataggaa atttaaatc tttaaccagt gtatcaactt caacacacaa  1080
tggtttgaa ggaactatac aacgcacaca taggccttct tatgaagata gagtttgttt 1140
tgtagctact gtcagattag ctacacctca gttcatcaag gaaatgtgta ctgttgaaga 1200
accaaatgaa gagtttacat ctagacacag tttagaatgg aagtttctat ttttagatca 1260
cagggcacca ccaataatag gctatttgcc atttgaagtc ttgggaacat caggctatga 1320
ttactatcat gtggatgacc tagaaaatct ggcaaaatgt cacgagcact taatgcaata 1380
tggaaaaggc aaatcgtgtt actatagatt cctgaccaaa ggccagcagt ggatatggct 1440
tcagactcat tattatatta cttaccatca gtggaattca aggccagagt tcattgtttg 1500
tactcacact gtagtaagtt atgcagaagt tagggctgaa agacggcgag aacttggcat 1560
tgaagagtct cttcctgaga cagctgctga caaaagccaa gattctgggt ctgacaatcg 1620
tatcaacaca gtgagtctca aggaagcact ggaaaggttt gatcacagcc caactccttc 1680
tgcctcctct agaagctcac gaaagtcatc tcacaccgca gtctcagacc cttcctccac 1740
accgacaaag atccctactg atactagcac tcctcccaga cagcatttgc cagctcatga 1800
aaagatgaca cagcggaggt cgtccttcag cagtcagtcc ataaactccc agtcagttgg 1860
tccatcatta acacagccag cgatgtctca agctgcaaat ttaccaattc cacaaggcat 1920
gtcacagttt cagttttcag ctcagttagg agccatgcag catctaaaag accagctaga 1980
gcagcggaca cggatgatag aggcaaatat tcatcggcag caagaagaac taaggaaaat 2040
tcaagagcaa cttcagatgg tccatggtca agggctacag atgttttgc agcaatcaaa 2100
ccctggattg aattttggtt ctgttcaact ttcctctgga aattctaata tccagcagct 2160
cacacctgta aatatgcaag gccaggttgt ccctgctaac caggttcaga gtggacatat 2220
cagcacaggc cagcacatga tacagcaaca gactttacaa agtacatcaa ctcagcagag 2280
```

-continued

```
tcaacagagt gtaatgagtg gacacagtca gcagacgtct cttccaagtc agacaccgag    2340
cactctcaca gccccactgt acaatacgat ggtgatttcc cagcctgcag ctgggagcat    2400
ggtccagatt ccatccagta tgccacagaa cagtacccag agtgctacag tcactacgtt    2460
cactcaggac agacagataa gattttctca aggtcagcaa cttgtgacca aattagtgac    2520
tgctcctgta gcttgtgggg ccgtcatggt accaagtacc atgcttatgg gtcaggtggt    2580
gactgcctat cctaccttcg ccacacaaca gcagcaggca cagacattat cggtaacaca    2640
acagcagcag cagcagcagc agcagccacc acagcaacag caacaacaac agcagagttc    2700
ccaggaacag cagcttcctt cagttcagca gccagctcag gcccagctgg gccagccacc    2760
acagcagttc ttacagacat ctaggttgct ccacgggaat ccttcgacac agctcatcct    2820
ctctgctgcc tttccactac aacagagcac tttccctcct tcgcaccacc agcaacacca    2880
gcctcagcag caacagcagc ttcctcggca caggactgac agcctgactg acccttccaa    2940
ggtccagcca cagtagcaca cacacttcct ctctgacatg cgagaggaag gggatggcca    3000
gaaagaatcg ctcagttggc atgcggtcag aagttgaaca gtttcacgag ggtggtcttg    3060
agtgttcagt cccttgatga gacggtaggg aagtgctgcc cagtgcttca gatgtccatt    3120
aaataccagc cagtgggaaa tggtcatagg gacacagcca attctgacag tttctttgcc    3180
caggtatttt ttgatagaaa gagtatattg ccaaatgcta acaagctcag ctatcaacca    3240
gatctttact gaatccgaag agcactaaca gtgttggtag ctttagtggg tctgtgcctg    3300
catcaaatat tacagagggc acaccactgc caggggtttg cttagaatgc catgaagata    3360
gtccagtagt taatagtccc cacccccaaac tcctctccct gttcagacaa tgatggaacc    3420
gtgatgactt tgagaatgtt gtgcaggttt gaattcactg tgtacagatg ctgtagtgtc    3480
tctgtgtctg gatggaggag agaaagccac tttgatacag aaagcattat ctgtccctca    3540
caggtatgag tgcatttcat taggtttgac accatgtaca aactgataac aacctctctt    3600
ttttcatttt gtttacaaca cagtagtgtt ctcgttactt ttccagggca caagtctttt    3660
tgtccgtgct ttggctgtga tgtcacagtt tgttcagtga ggtaacaatg tgctgctggg    3720
aatggatttt tttaaggtta aattattgct acatttccac ttactcagaa atatccctta    3780
tttcattatt tttcaattat gtttgagaga attgcactgc tttattattt tagatggttg    3840
gttgagagtt taatcacata ttttgatata tttcatagtt ggaatattta tgtaaatggt    3900
tttcaacaag cctgaaagta atttcaagaa tgtttcagtt gtaagagtaa agtttgcaca    3960
caaaacattt taggcacttt tttaacattc tcagaggtgg aatttaac ttttaggatt    4020
tgttggaatc ttttattat ctttaaaaat ttcaatgctt cttttagtca gaaatgattc    4080
agggttattt gagggaaaa aacccatagt gccttgattt taattcaggt gataactcac    4140
catcttgaat tcattgtctg gtttcagtag cagttttgaa accttagtac atttttagca    4200
gcagtgtcat tctcaagtcc ccatgaggac tgctgcgtct cttggctgc ctgacagcgt    4260
cacagctggg aatgggatcc caaaatcgtt tcctgtttgc atcttcctct aaagctaagt    4320
aactctttta ggaattacca gtaaatactt gctcagagac aagggacaag ttgtctttaa    4380
ttttcattgc agcactagaa taatgtaact cacatgcttt ttaaacatta agatttcatt    4440
tggcaatatc attctctaca ggtaataaac tccaacaaag ctacatacat tttaaaaggc    4500
attttttag attttatggt actaataatg agtttttcaa ttaaagaaca aaagatcagt    4560
aggatataga atatcaagta ttactgagaa aagggaggat aagtgtggca cattagaatt    4620
gacctaaaaa ggaaagtatg tgatggtgag gtgctaaact ggtttcagca gtgcagataa    4680
```

```
cctaaggcag agttgctaga tcagggcttg gggaactcgg agtcagctat ctgtctctag    4740
ctttgctctc atcatcagta agtgtgtctt tgttttcctg tttacctgac tgcaattaag    4800
ttagcaagtt agtgataaaa agaaaacaac caaagaaaat tggtacctac tcttctgcgt    4860
aagaagtgtg tctagatacc agtcagtaac tcacatatca cagaagttct tctagctgac    4920
attcatacga ataccagaaa tagttgtgag aatacacatt tatgcaagtt tgtgcacacg    4980
tgacgaaatc aatgtaagtc gagcacccac attgcttttc tcccttccac attgccttct    5040
tctctttggc cattccatgt cctcggagtc ggagctgtgc ctcgtttatc tttttgcatc    5100
acatagcgat aagaatttag ctacaggaga tacaacatgc tagttatgta atgcctgctg    5160
ttcttcacag ttcatctccc tgcttaaaag tagcagttga taagaaactc tagctgctaa    5220
ggctgctgtc cacacggaga tgcatgctgg gcaacagttg tcagcactag ctgcctctta    5280
gctccttaat tcttggttcc tttggatggc aaactgtctt tgtctgctcc ccacacgact    5340
ccagtattct gaagaaagtt catcttttgc ctgttcattt ctgtagccaa agctgactga    5400
aaccccaaat ctaaatcatg aaaagatacc aaaagaaac acttctcagc ttcttagaaa     5460
ccttaacttc tcttgctgta tttcatggat ttgattttct ttgaaatttt tgattctggg    5520
cagcgccttt taattaagaa attgttagga tgaaggtcaa acaggttctc attgccctgc    5580
aggtaccttg ctctggactg cttctgtatg gggtgacttg gggttgctga acacacagga    5640
ttagaacagt aaacacaaag ctgcccttga ggctggcgtt aaaccagagc tcaatattg     5700 aaaatatcaa gtcctctttc cttccttaga gacgagactg tgagaggaaa gcaactgtgg    5760
taggtgggct tgcttgcaca tgagcaccaa gaccattccc caagctctat cctcagggta    5820
gcatttagag tgctgtgttc tgctgtcaca tagacatggc ttagggatgt agcactaata    5880
aaagaatgcc cgtgcttttg aatagttgtg atagcaaact ctaggctaac tagcaagtgt    5940
ttgaattctg tgtgctgtat agtagttggt cattgcctta aagcagtctc ttggaagttg    6000
ggagcactga agcagtccaa ccatatatgg gcatcacgtt gagggagatg agccttgttc    6060
aagccttaga aaggaccctt agtctacaca ggtagattct tttcacttgg atattactgt    6120
gtttaaaatg tttccactat gttgaggcag tttttttaaag tggaacacag ataggatttt    6180
tagtatttct ttttttgttt ctttggtgat taaaggtttg ttggtagaca tttgtgtaaa    6240
agttgttcaa gcctatcatc tttccagtac ttgtggtcct gttcttagta ccagagtcca    6300
caatggaaag tgtaaacact ggatattaat attgctgagg gtgcatagcc aggtgtgagc    6360
tgactggaac ttctcagtgg tgaagaaaca gcacaacggc acttgccatt tcatagtga    6420 ttgcataaag agaccttcta agtttgtctg gattgagtga acactcttct aagaggagct    6480
tctcaagtaa atgcaaagga aaagagttga ctatttttat agcatattta atatatttgt    6540
atataactat gagtgtagta ggaacccctcc acatgcctcc cacttttcta attccctccc    6600
cttctgccgt agccctagtc cagcctcatc cgcatgggta atgtgcctac tgtcagccta    6660
cctaccaaaa gatagtgctg ctgctttctg agacaggtga gatcagactc tcatgcctgg    6720
ggatccttat gggaggaata gcacacactt agaacaacat accacagttt aagagcatca    6780
ttttgaaagg taataagcac tttattgcaa ttattcattt agataaagtt tgtatcttag    6840
gcattaaccg ttttttaaagg atccctaatc atcacttagg tgaaatgata aacgacacat    6900
ttctgagaaa tgttcaggtc cagtgaaccg tagcaggttt atgggaatga tttcaaggta    6960
gccaaataaa ctctgacttt tgttttgaat gtggtggagt caggagattg tagatgtgta    7020
```

-continued

```
gtttgattta aacactattg taaacctatc ttgcctattg tgtggacacc aaaagagacc    7080
aatgagcctg tttatttca gaggtctagg aatatgcatc tgtctgagta gatatacaga    7140
actaatctat aaacggttgg tagtaatatt ttaggataca gtaacttaaa gaattattga    7200
gtgttttaaa tgtgccctga aatgttggca tgtcatttca gcgttcccat ttgagttgct    7260
cttgtaatat ttttgcacaa aaaggactga gaaaagactg ctttggttga agaaaactat    7320
aatttggtct tatttaatg tctcctgtgg aaacactgga ggtaaatttg ttggcatagt    7380
tactaattca ggatatttaa aacagtgttg aacagctcat cagaaattaa gcaaacttat    7440
atatttaaaa attaaaaatc ttttttttcca tgtgactgaa aaaaaaaaaa aaaaaaa     7498
```

<210> SEQ ID NO 2
<211> LENGTH: 855
<212> TYPE: PRT
<213> ORGANISM: Mus musculus

<400> SEQUENCE: 2

```
Met Val Phe Thr Val Ser Cys Ser Lys Met Ser Ser Ile Val Asp Arg
 1               5                  10                  15

Asp Asp Ser Ser Ile Phe Asp Gly Leu Val Glu Glu Asp Lys Asp
                20                  25                  30

Lys Ala Lys Arg Val Ser Arg Asn Lys Ser Glu Lys Lys Arg Arg Asp
        35                  40                  45

Gln Phe Asn Val Leu Ile Lys Glu Leu Gly Ser Met Leu Pro Gly Asn
    50                  55                  60

Ala Arg Lys Met Asp Lys Ser Thr Val Leu Gln Lys Ser Ile Asp Phe
65                  70                  75                  80

Leu Arg Lys His Lys Glu Thr Thr Ala Gln Ser Asp Ala Ser Glu Ile
                85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
        115                 120                 125

Gly Ser Ile Ile Tyr Val Ser Glu Ser Val Thr Ser Leu Leu Glu His
    130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Arg Phe Ile Gly Asn Phe Lys Ser Leu Thr Ser
    210                 215                 220

Val Ser Thr Ser Thr His Asn Gly Phe Glu Gly Thr Ile Gln Arg Thr
225                 230                 235                 240

His Arg Pro Ser Tyr Glu Asp Arg Val Cys Phe Val Ala Thr Val Arg
                245                 250                 255

Leu Ala Thr Pro Gln Phe Ile Lys Glu Met Cys Thr Val Glu Glu Pro
            260                 265                 270

Asn Glu Glu Phe Thr Ser Arg His Ser Leu Glu Trp Lys Phe Leu Phe
        275                 280                 285

Leu Asp His Arg Ala Pro Pro Ile Ile Gly Tyr Leu Pro Phe Glu Val
```

-continued

```
            290                 295                 300
Leu Gly Thr Ser Gly Tyr Asp Tyr Tyr His Val Asp Asp Leu Glu Asn
305                 310                 315                 320
Leu Ala Lys Cys His Glu His Leu Met Gln Tyr Gly Lys Gly Lys Ser
                325                 330                 335
Cys Tyr Tyr Arg Phe Leu Thr Lys Gly Gln Gln Trp Ile Trp Leu Gln
                340                 345                 350
Thr His Tyr Tyr Ile Thr Tyr His Gln Trp Asn Ser Arg Pro Glu Phe
                355                 360                 365
Ile Val Cys Thr His Thr Val Val Ser Tyr Ala Glu Val Arg Ala Glu
                370                 375                 380
Arg Arg Arg Glu Leu Gly Ile Glu Glu Ser Leu Pro Glu Thr Ala Ala
385                 390                 395                 400
Asp Lys Ser Gln Asp Ser Gly Ser Asp Asn Arg Ile Asn Thr Val Ser
                405                 410                 415
Leu Lys Glu Ala Leu Glu Arg Phe Asp His Ser Pro Thr Pro Ser Ala
                420                 425                 430
Ser Ser Arg Ser Ser Arg Lys Ser Ser His Thr Ala Val Ser Asp Pro
                435                 440                 445
Ser Ser Thr Pro Thr Lys Ile Pro Thr Asp Thr Ser Thr Pro Pro Arg
450                 455                 460
Gln His Leu Pro Ala His Glu Lys Met Thr Gln Arg Arg Ser Ser Phe
465                 470                 475                 480
Ser Ser Gln Ser Ile Asn Ser Gln Ser Val Gly Pro Ser Leu Thr Gln
                485                 490                 495
Pro Ala Met Ser Gln Ala Ala Asn Leu Pro Ile Pro Gln Gly Met Ser
                500                 505                 510
Gln Phe Gln Phe Ser Ala Gln Leu Gly Ala Met Gln His Leu Lys Asp
                515                 520                 525
Gln Leu Glu Gln Arg Thr Arg Met Ile Glu Ala Asn Ile His Arg Gln
                530                 535                 540
Gln Glu Glu Leu Arg Lys Ile Gln Glu Gln Leu Gln Met Val His Gly
545                 550                 555                 560
Gln Gly Leu Gln Met Phe Leu Gln Gln Ser Asn Pro Gly Leu Asn Phe
                565                 570                 575
Gly Ser Val Gln Leu Ser Ser Gly Asn Ser Asn Ile Gln Gln Leu Thr
                580                 585                 590
Pro Val Asn Met Gln Gly Gln Val Val Pro Ala Asn Gln Val Gln Ser
                595                 600                 605
Gly His Ile Ser Thr Gly Gln His Met Ile Gln Gln Thr Leu Gln
                610                 615                 620
Ser Thr Ser Thr Gln Gln Ser Gln Gln Ser Val Met Ser Gly His Ser
625                 630                 635                 640
Gln Gln Thr Ser Leu Pro Ser Gln Thr Pro Ser Thr Leu Thr Ala Pro
                645                 650                 655
Leu Tyr Asn Thr Met Val Ile Ser Gln Pro Ala Ala Gly Ser Met Val
                660                 665                 670
Gln Ile Pro Ser Ser Met Pro Gln Asn Ser Thr Gln Ser Ala Thr Val
                675                 680                 685
Thr Thr Phe Thr Gln Asp Arg Gln Ile Arg Phe Ser Gln Gly Gln Gln
                690                 695                 700
Leu Val Thr Lys Leu Val Thr Ala Pro Val Ala Cys Gly Ala Val Met
705                 710                 715                 720
```

```
Val Pro Ser Thr Met Leu Met Gly Gln Val Val Thr Ala Tyr Pro Thr
                725                 730                 735

Phe Ala Thr Gln Gln Gln Gln Ala Gln Thr Leu Ser Val Thr Gln Gln
            740                 745                 750

Gln Gln Gln Gln Gln Gln Gln Pro Pro Gln Gln Gln Gln Gln Gln Gln
        755                 760                 765

Gln Ser Ser Gln Glu Gln Gln Leu Pro Ser Val Gln Gln Pro Ala Gln
        770                 775                 780

Ala Gln Leu Gly Gln Pro Pro Gln Gln Phe Leu Gln Thr Ser Arg Leu
785                 790                 795                 800

Leu His Gly Asn Pro Ser Thr Gln Leu Ile Leu Ser Ala Ala Phe Pro
                805                 810                 815

Leu Gln Gln Ser Thr Phe Pro Pro Ser His His Gln His Gln His Pro
            820                 825                 830

Gln Gln Gln Gln Leu Pro Arg His Arg Thr Asp Ser Leu Thr Asp
        835                 840                 845

Pro Ser Lys Val Gln Pro Gln
    850                 855

<210> SEQ ID NO 3
<211> LENGTH: 70
<212> TYPE: DNA
<213> ORGANISM: Mus musculus

<400> SEQUENCE: 3
gctggagaga ggaaaccccg gacggcgaga gcgcgaagga aatctggccg ccgccgcgca        60
cgcgctcccg                                                              70

<210> SEQ ID NO 4
<211> LENGTH: 18
<212> TYPE: DNA
<213> ORGANISM: Mus musculus

<400> SEQUENCE: 4
gcgctcccgg tgagtgcg                                                     18

<210> SEQ ID NO 5
<211> LENGTH: 18
<212> TYPE: DNA
<213> ORGANISM: Mus musculus

<400> SEQUENCE: 5
tcaggcacgg tgaggacg                                                     18

<210> SEQ ID NO 6
<211> LENGTH: 18
<212> TYPE: DNA
<213> ORGANISM: Mus musculus

<400> SEQUENCE: 6
accagcaagg taatttcc                                                     18

<210> SEQ ID NO 7
<211> LENGTH: 18
<212> TYPE: DNA
<213> ORGANISM: Mus musculus

<400> SEQUENCE: 7
gtgaaagagg taaaggcg                                                     18
```

```
<210> SEQ ID NO 8
<211> LENGTH: 18
<212> TYPE: DNA
<213> ORGANISM: Mus musculus

<400> SEQUENCE: 8
tgttgacagg tatgtttt                                                18

<210> SEQ ID NO 9
<211> LENGTH: 18
<212> TYPE: DNA
<213> ORGANISM: Mus musculus

<400> SEQUENCE: 9
agcaaaaagg tagttagc                                                18

<210> SEQ ID NO 10
<211> LENGTH: 18
<212> TYPE: DNA
<213> ORGANISM: Mus musculus

<400> SEQUENCE: 10
aacataaagg taaagtgc                                                18

<210> SEQ ID NO 11
<211> LENGTH: 18
<212> TYPE: DNA
<213> ORGANISM: Mus musculus

<400> SEQUENCE: 11
atgttagagg tatgttca                                                18

<210> SEQ ID NO 12
<211> LENGTH: 18
<212> TYPE: DNA
<213> ORGANISM: Mus musculus

<400> SEQUENCE: 12
catttaccag taagtatg                                                18

<210> SEQ ID NO 13
<211> LENGTH: 18
<212> TYPE: DNA
<213> ORGANISM: Mus musculus

<400> SEQUENCE: 13
acttaaaatg taagtagg                                                18

<210> SEQ ID NO 14
<211> LENGTH: 18
<212> TYPE: DNA
<213> ORGANISM: Mus musculus

<400> SEQUENCE: 14
taaccagtgg taagttaa                                                18

<210> SEQ ID NO 15
<211> LENGTH: 18
<212> TYPE: DNA
<213> ORGANISM: Mus musculus

<400> SEQUENCE: 15
ttcatcaagg tatgcttc                                                18
```

-continued

<210> SEQ ID NO 16
<211> LENGTH: 18
<212> TYPE: DNA
<213> ORGANISM: Mus musculus

<400> SEQUENCE: 16
agatcacagg taacatta                                               18

<210> SEQ ID NO 17
<211> LENGTH: 18
<212> TYPE: DNA
<213> ORGANISM: Mus musculus

<400> SEQUENCE: 17
acgagcactg taagtagc                                               18

<210> SEQ ID NO 18
<211> LENGTH: 18
<212> TYPE: DNA
<213> ORGANISM: Mus musculus

<400> SEQUENCE: 18
tgtagtaagg taataact                                               18

<210> SEQ ID NO 19
<211> LENGTH: 18
<212> TYPE: DNA
<213> ORGANISM: Mus musculus

<400> SEQUENCE: 19
gctgacaaag tatgtttc                                               18

<210> SEQ ID NO 20
<211> LENGTH: 18
<212> TYPE: DNA
<213> ORGANISM: Mus musculus

<400> SEQUENCE: 20
acccttcctg tgagtgcc                                               18

<210> SEQ ID NO 21
<211> LENGTH: 18
<212> TYPE: DNA
<213> ORGANISM: Mus musculus

<400> SEQUENCE: 21
agcagtcagg tacgcctt                                               18

<210> SEQ ID NO 22
<211> LENGTH: 18
<212> TYPE: DNA
<213> ORGANISM: Mus musculus

<400> SEQUENCE: 22
atgtcacagg tatttttg                                               18

<210> SEQ ID NO 23
<211> LENGTH: 18
<212> TYPE: DNA
<213> ORGANISM: Mus musculus

<400> SEQUENCE: 23

-continued gggctacagg taacttat                                         18

<210> SEQ ID NO 24
<211> LENGTH: 18
<212> TYPE: DNA
<213> ORGANISM: Mus musculus

<400> SEQUENCE: 24
tcaactcagg taattgac                                         18

<210> SEQ ID NO 25
<211> LENGTH: 18
<212> TYPE: DNA
<213> ORGANISM: Mus musculus

<400> SEQUENCE: 25
acagataagg tagttgtc                                         18

<210> SEQ ID NO 26
<211> LENGTH: 18
<212> TYPE: DNA
<213> ORGANISM: Mus musculus

<400> SEQUENCE: 26
ttcttacagg taacccccc                                        18

<210> SEQ ID NO 27
<211> LENGTH: 29
<212> TYPE: DNA
<213> ORGANISM: Mus musculus

<400> SEQUENCE: 27
tctggtgttt tctattgcag tgaaagaaa                             29

<210> SEQ ID NO 28
<211> LENGTH: 29
<212> TYPE: DNA
<213> ORGANISM: Mus musculus

<400> SEQUENCE: 28
cttttgtttt tttaaaacag agttctgat                             29

<210> SEQ ID NO 29
<211> LENGTH: 29
<212> TYPE: DNA
<213> ORGANISM: Mus musculus

<400> SEQUENCE: 29
atgttttctt ttctcacaag gagaagtac                             29

<210> SEQ ID NO 30
<211> LENGTH: 29
<212> TYPE: DNA
<213> ORGANISM: Mus musculus

<400> SEQUENCE: 30
ctctgtcttt tctcttgtag agatgacag                             29

<210> SEQ ID NO 31
<211> LENGTH: 29
<212> TYPE: DNA
<213> ORGANISM: Mus musculus

<400> SEQUENCE: 31

-continued

```
taatttcttt ttcttcatag agtatctag                                          29

<210> SEQ ID NO 32
<211> LENGTH: 29
<212> TYPE: DNA
<213> ORGANISM: Mus musculus

<400> SEQUENCE: 32
acgtgtcaat ctgtttacag agaccactg                                          29

<210> SEQ ID NO 33
<211> LENGTH: 29
<212> TYPE: DNA
<213> ORGANISM: Mus musculus

<400> SEQUENCE: 33
accattatgt ttaatttcag gctcttgat                                          29

<210> SEQ ID NO 34
<211> LENGTH: 29
<212> TYPE: DNA
<213> ORGANISM: Mus musculus

<400> SEQUENCE: 34
tttttttttt tattttcag tctgatctt                                           29

<210> SEQ ID NO 35
<211> LENGTH: 29
<212> TYPE: DNA
<213> ORGANISM: Mus musculus

<400> SEQUENCE: 35 cttttatca cttattccag caaaaaatc                                           29

<210> SEQ ID NO 36
<211> LENGTH: 29
<212> TYPE: DNA
<213> ORGANISM: Mus musculus

<400> SEQUENCE: 36
atgtctcctt gctgttttag tatcaactt                                          29

<210> SEQ ID NO 37
<211> LENGTH: 29
<212> TYPE: DNA
<213> ORGANISM: Mus musculus

<400> SEQUENCE: 37
acttgttaat ttgtttgtag gaaatgtgt                                          29

<210> SEQ ID NO 38
<211> LENGTH: 29
<212> TYPE: DNA
<213> ORGANISM: Mus musculus

<400> SEQUENCE: 38
attattactg tataatttag ggcaccacc                                          29

<210> SEQ ID NO 39
<211> LENGTH: 29
<212> TYPE: DNA
<213> ORGANISM: Mus musculus
```

<400> SEQUENCE: 39
ttttattttt ttatttttag taatgcaat                                              29

<210> SEQ ID NO 40
<211> LENGTH: 29
<212> TYPE: DNA
<213> ORGANISM: Mus musculus

<400> SEQUENCE: 40
ttggttcttt ccatttgtag ttattgcag                                              29

<210> SEQ ID NO 41
<211> LENGTH: 29
<212> TYPE: DNA
<213> ORGANISM: Mus musculus

<400> SEQUENCE: 41
tgttcctctt atctccttag agccaagat                                              29

<210> SEQ ID NO 42
<211> LENGTH: 29
<212> TYPE: DNA
<213> ORGANISM: Mus musculus

<400> SEQUENCE: 42
tctctgttga ctgtctttag ccacaccga                                              29

<210> SEQ ID NO 43
<211> LENGTH: 29
<212> TYPE: DNA
<213> ORGANISM: Mus musculus

<400> SEQUENCE: 43 atctttatt ttgcttctag tccataaac                                               29

<210> SEQ ID NO 44
<211> LENGTH: 29
<212> TYPE: DNA
<213> ORGANISM: Mus musculus

<400> SEQUENCE: 44
ctttccatgt gctgcttcag tttcagttt                                              29

<210> SEQ ID NO 45
<211> LENGTH: 29
<212> TYPE: DNA
<213> ORGANISM: Mus musculus

<400> SEQUENCE: 45
tgtgatcttt gttttcaaag atgttttg                                               29

<210> SEQ ID NO 46
<211> LENGTH: 29
<212> TYPE: DNA
<213> ORGANISM: Mus musculus

<400> SEQUENCE: 46
ttccatacga tcttttctag cagagtcaa                                              29

<210> SEQ ID NO 47
<211> LENGTH: 29
<212> TYPE: DNA
<213> ORGANISM: Mus musculus -continued

<400> SEQUENCE: 47
tattttgttt tctctcacag attttctca                29

<210> SEQ ID NO 48
<211> LENGTH: 29
<212> TYPE: DNA
<213> ORGANISM: Mus musculus

<400> SEQUENCE: 48
atcatccttt ttgtttttag acatctagg                29

<210> SEQ ID NO 49
<211> LENGTH: 18
<212> TYPE: DNA
<213> ORGANISM: Mus musculus

<400> SEQUENCE: 49
gggctacagg taacttat                            18

<210> SEQ ID NO 50
<211> LENGTH: 18
<212> TYPE: DNA
<213> ORGANISM: Mus musculus

<400> SEQUENCE: 50
gggctacagg ttacttat                            18

<210> SEQ ID NO 51
<211> LENGTH: 747
<212> TYPE: PRT
<213> ORGANISM: Mus musculus

<400> SEQUENCE: 51

Met Asp Glu Asp Glu Lys Asp Arg Ala Lys Arg Ala Ser Arg Asn Lys
  1               5                  10                  15

Ser Glu Lys Lys Arg Arg Asp Gln Phe Asn Val Leu Ile Lys Glu Leu
             20                  25                  30

Ser Ser Met Leu Pro Gly Asn Ile Arg Lys Met Asp Lys Ile Thr Val
         35                  40                  45

Leu Glu Lys Val Ile Gly Phe Leu Gln Lys His Asn Glu Val Ser Ala
     50                  55                  60

Gln Thr Glu Ile Cys Asp Ile Gln Gln Asp Trp Lys Pro Ser Phe Leu
 65                  70                  75                  80

Ser Asn Glu Glu Phe Thr Gln Leu Met Leu Glu Ala Leu Asp Gly Phe
                 85                  90                  95

Ile Ala Val Thr Thr Asp Gly Ser Ile Ile Tyr Val Ser Asp Ser Ile
            100                 105                 110

Thr Pro Leu Leu Gly His Leu Pro Ser Asp Val Met Asp Gln Asn Leu
        115                 120                 125

Leu Asn Phe Leu Pro Glu Gln Glu His Ser Glu Val Tyr Lys Ile Leu
    130                 135                 140

Ser Ser His Met Leu Val Thr Asp Ser Pro Ser Pro Glu Tyr Leu Lys
145                 150                 155                 160

Ser Asp Asn Asp Leu Glu Phe Tyr Cys His Leu Leu Arg Gly Ser Leu
                165                 170                 175

Asn Pro Lys Glu Phe Pro Thr Tyr Glu Tyr Ile Lys Phe Val Gly Asn
            180                 185                 190

```
Phe Arg Ser Tyr Asn Asn Val Pro Ser Pro Ser Cys Asn Gly Phe Asp
            195                 200                 205
Asn Thr Leu Ser Arg Pro Cys Arg Val Pro Leu Gly Lys Val Cys Phe
            210                 215                 220
Ile Ala Thr Val Arg Leu Ala Thr Pro Gln Phe Leu Lys Glu Met Cys
225                 230                 235                 240
Val Asp Glu Pro Leu Glu Glu Phe Thr Ser Arg His Ser Leu Glu Trp
            245                 250                 255
Lys Phe Leu Phe Leu Asp His Arg Ala Pro Pro Ile Ile Gly Tyr Leu
            260                 265                 270
Pro Phe Glu Val Leu Gly Thr Ser Gly Tyr Asp Tyr His Ile Asp
            275                 280                 285
Asp Leu Glu Leu Leu Ala Arg Cys His Gln His Leu Met Gln Phe Gly
            290                 295                 300
Lys Gly Lys Ser Cys Cys Tyr Arg Phe Leu Thr Lys Gly Gln Gln Trp
305                 310                 315                 320
Ile Trp Leu Gln Thr His Tyr Tyr Ile Thr Tyr His Gln Trp Asn Ser
            325                 330                 335
Lys Pro Glu Phe Ile Val Cys Thr His Ser Val Val Ser Tyr Ala Asp
            340                 345                 350
Val Arg Val Glu Arg Arg Gln Glu Leu Ala Leu Glu Asp Pro Pro Glu
            355                 360                 365
Ala His Ser Ala Lys Lys Asp Ser Ser Leu Glu Pro Arg Gln Phe Asn
            370                 375                 380
Ala Leu Asp Gly Ala Ser Gly Leu Ser Pro Ser Pro Ser Ala Ser Ser
385                 390                 395                 400
Arg Ser Ser His Lys Ser Ser His Thr Ala Met Ser Glu Pro Ile Ser
            405                 410                 415
Thr Pro Thr Lys Leu Met Ala Glu Ser Thr Ala Leu Pro Arg Ala Thr
            420                 425                 430
Leu Pro Gln Glu Leu Pro Val Gly Leu Ser Gln Ala Ala Thr Met Pro
            435                 440                 445
Leu Ser Ser Cys Asp Leu Thr Gln Gln Leu Leu Gln Pro Gln Thr
450                 455                 460
Leu Gln Ser Pro Ala Pro Gln Phe Ser Ala Gln Phe Ser Met Phe Gln
465                 470                 475                 480
Thr Ile Lys Asp Gln Leu Glu Gln Arg Thr Arg Ile Leu Gln Ala Asn
            485                 490                 495
Ile Arg Trp Gln Gln Glu Glu Leu His Lys Ile Gln Glu Gln Leu Cys
            500                 505                 510
Leu Val Gln Asp Ser Asn Val Gln Met Phe Leu Gln Gln Pro Ala Val
            515                 520                 525
Ser Leu Ser Phe Ser Ser Ile Gln Arg Pro Ala Gln Gln Leu Gln
            530                 535                 540
Gln Arg Ala Ala Gln Pro Gln Leu Val Gln Leu Gln Gly Gln Ile Ser
545                 550                 555                 560
Thr Gln Val Thr Gln His Leu Leu Arg Glu Ser Ser Val Ile Ser Gln
            565                 570                 575
Gly Pro Lys Pro Met Arg Ser Ser Gln Leu Ser Gly Arg Ser Ser Ser
            580                 585                 590
Leu Ser Pro Phe Ser Ser Thr Leu Pro Pro Leu Leu Thr Thr Pro Ala
            595                 600                 605
Ser Thr Pro Gln Asp Ser Gln Cys Gln Pro Ser Pro Asp Phe His Asp
```

```
            610                 615                 620
Arg Gln Leu Arg Leu Leu Ser Gln Pro Ile Gln Pro Met Met Pro
625                 630                 635                 640

Gly Ser Cys Asp Ala Arg Gln Pro Ser Glu Val Ser Arg Thr Gly Arg
                645                 650                 655

Gln Val Lys Tyr Ala Gln Ser Gln Phe Pro Asp His Pro Asn Ser Ser
                660                 665                 670

Pro Val Leu Leu Met Gly Gln Ala Val Leu His Pro Ser Phe Pro Ala
                675                 680                 685

Ser Pro Ser Pro Leu Gln Pro Ala Gln Ala Gln Gln Pro Pro Pro
        690                 695                 700

Gln Ala Pro Thr Ser Leu His Ser Glu Gln Asp Ser Leu Leu Leu Ser
705                 710                 715                 720

Thr Phe Ser Gln Gln Pro Gly Thr Leu Gly Tyr Gln Gln Pro Gln Pro
                725                 730                 735

Arg Pro Arg Arg Val Ser Leu Ser Glu Ser Pro
                740                 745
```

<210> SEQ ID NO 52
<211> LENGTH: 824
<212> TYPE: PRT
<213> ORGANISM: Mus musculus

<400> SEQUENCE: 52

```
Met Asp Glu Asp Glu Lys Asp Arg Ala Lys Arg Ala Ser Arg Asn Lys
1               5                   10                  15

Ser Glu Lys Lys Arg Arg Asp Gln Phe Asn Val Leu Ile Lys Glu Leu
                20                  25                  30

Ser Ser Met Leu Pro Gly Asn Ile Arg Lys Met Asp Lys Ile Thr Val
            35                  40                  45

Leu Glu Lys Val Ile Gly Phe Leu Gln Lys His Asn Glu Val Ser Ala
        50                  55                  60

Gln Thr Glu Ile Cys Asp Ile Gln Gln Asp Trp Lys Pro Ser Phe Leu
65                  70                  75                  80

Ser Asn Glu Glu Phe Thr Gln Leu Met Leu Glu Ala Leu Asp Gly Phe
                85                  90                  95

Ile Ile Ala Val Thr Thr Asp Gly Ser Ile Ile Tyr Val Ser Asp Ser
                100                 105                 110

Ile Thr Pro Leu Leu Gly His Leu Pro Ser Asp Val Met Asp Gln Asn
            115                 120                 125

Leu Leu Asn Phe Leu Pro Glu Gln Glu His Ser Glu Val Tyr Lys Ile
130                 135                 140

Leu Ser Ser His Met Leu Val Thr Asp Ser Pro Ser Pro Glu Tyr Leu
145                 150                 155                 160

Lys Ser Asp Ser Asp Leu Glu Phe Tyr Cys His Leu Leu Arg Gly Ser
                165                 170                 175

Leu Asn Pro Lys Glu Phe Pro Thr Tyr Glu Tyr Ile Lys Phe Val Gly
                180                 185                 190

Asn Phe Arg Ser Tyr Asn Asn Val Pro Ser Pro Ser Cys Asn Gly Phe
            195                 200                 205

Asp Asn Thr Leu Ser Arg Pro Cys Arg Val Pro Leu Gly Lys Glu Val
        210                 215                 220

Cys Phe Ile Ala Thr Val Arg Leu Ala Thr Pro Gln Phe Leu Lys Glu
225                 230                 235                 240
```

-continued

```
Met Cys Ile Val Asp Glu Pro Leu Glu Phe Thr Ser Arg His Ser
                245                 250                 255

Leu Glu Trp Lys Phe Leu Phe Leu Asp His Arg Ala Pro Pro Ile Ile
            260                 265                 270

Gly Tyr Leu Pro Phe Glu Val Leu Gly Thr Ser Gly Tyr Asp Tyr Tyr
                275                 280                 285

His Ile Asp Asp Leu Glu Leu Leu Ala Arg Cys His Gln His Leu Met
    290                 295                 300

Gln Phe Gly Ile Gly Lys Ser Cys Cys Tyr Arg Phe Leu Thr Lys Gly
305                 310                 315                 320

Gln Gln Trp Ile Trp Leu Gln Thr His Tyr Tyr Ile Thr Tyr His Gln
                325                 330                 335

Trp Asn Ser Lys Pro Glu Phe Ile Val Cys Thr His Ser Val Val Ser
            340                 345                 350

Tyr Ala Asp Val Arg Val Glu Arg Arg Gln Glu Leu Ala Leu Glu Asp
                355                 360                 365

Pro Pro Ser Glu Ala Leu His Ser Ser Ala Leu Lys Asp Lys Gly Ser
        370                 375                 380

Ser Leu Glu Pro Arg Gln His Phe Asn Ala Leu Asp Val Gly Ala Ser
385                 390                 395                 400

Gly Leu Asn Thr Ser His Ser Pro Ser Ala Ser Ser Arg Ser Ser His
                405                 410                 415

Lys Ser Ser His Thr Ala Met Ser Glu Pro Ile Ser Thr Pro Thr Lys
            420                 425                 430

Leu Met Ala Glu Ala Ser Thr Pro Ala Leu Pro Arg Ser Ala Thr Leu
        435                 440                 445

Pro Gln Glu Leu Pro Val Pro Gly Leu Ser Gln Ala Ala Thr Met Pro
    450                 455                 460

Ala Pro Leu Pro Ser Pro Leu Ser Cys Asp Leu Thr Gln Gln Leu Leu
465                 470                 475                 480

Pro Gln Thr Val Leu Gln Ser Thr Pro Ala Pro Met Ala Gln Phe Ser
                485                 490                 495

Ala Gln Phe Ser Met Phe Gln Thr Ile Lys Asp Gln Leu Glu Gln Arg
            500                 505                 510

Thr Arg Ile Leu Gln Ala Asn Ile Arg Trp Gln Gln Glu Glu Leu His
        515                 520                 525

Lys Ile Gln Glu Gln Leu Cys Leu Val Gln Asp Ser Asn Val Gln Met
    530                 535                 540

Phe Leu Gln Gln Pro Ala Val Ser Leu Ser Phe Ser Ser Ile Gln Arg
545                 550                 555                 560

Pro Glu Ala Gln Gln Leu Gln Gln Arg Ser Ala Ala Val Thr Gln
                565                 570                 575

Pro Gln Leu Gly Ala Gly Pro Gln Leu Pro Gly Gln Ile Ser Ser Ala
            580                 585                 590

Gln Val Thr Ser Gln His Leu Leu Arg Glu Ser Ser Val Ile Ser Thr
        595                 600                 605

Gln Gly Pro Lys Pro Met Arg Ser Ser Gln Leu Met Gln Ser Ser Gly
    610                 615                 620

Arg Ser Gly Ser Ser Leu Val Ser Pro Phe Ser Ser Ala Thr Ala Ala
625                 630                 635                 640

Leu Pro Pro Ser Leu Asn Leu Thr Thr Pro Ala Ser Thr Ser Gln Asp
                645                 650                 655

Ala Ser Gln Cys Gln Pro Ser Pro Asp Phe Ser His Asp Arg Gln Leu
```

```
                     660                 665                 670
Arg Leu Leu Leu Ser Gln Pro Ile Gln Pro Met Met Pro Gly Ser Cys
            675                 680                 685

Asp Ala Arg Gln Pro Ser Glu Val Ser Arg Thr Gly Arg Gln Val Lys
        690                 695                 700

Tyr Ala Gln Ser Gln Thr Val Phe Gln Asn Pro Asp Ala His Pro Ala
705                 710                 715                 720

Asn Ser Ser Ser Ala Pro Met Pro Val Leu Leu Met Gly Gln Ala Val
                725                 730                 735

Leu His Pro Ser Phe Pro Ala Ser Gln Pro Ser Pro Leu Gln Pro Ala
            740                 745                 750

Gln Ala Arg Gln Gln Pro Gln His Tyr Leu Gln Val Gln Ala Pro
        755                 760                 765

Thr Ser Leu His Ser Glu Gln Gln Asp Ser Leu Leu Leu Ser Thr Tyr
        770                 775                 780

Ser Gln Gln Pro Gly Thr Leu Gly Tyr Pro Gln Pro Pro Ala Gln
785                 790                 795                 800

Pro Gln Pro Leu Arg Pro Pro Arg Val Ser Ser Leu Ser Glu Ser
                805                 810                 815

Ser Gly Leu Gln Gln Pro Pro Arg
            820

<210> SEQ ID NO 53
<211> LENGTH: 816
<212> TYPE: PRT
<213> ORGANISM: Mus musculus

<400> SEQUENCE: 53

Met Asp Glu Asp Glu Lys Asp Arg Ala Lys Arg Ala Ser Arg Asn Lys
  1               5                  10                  15

Ser Glu Lys Lys Arg Arg Asp Gln Phe Asn Val Leu Ile Lys Glu Leu
                20                  25                  30

Ser Ser Met Leu Pro Gly Asn Ile Arg Lys Met Asp Lys Ile Thr Val
            35                  40                  45

Leu Glu Lys Val Ile Gly Phe Leu Gln Lys His Asn Glu Val Ser Ala
        50                  55                  60

Gln Thr Glu Ile Cys Asp Ile Gln Gln Asp Trp Lys Pro Ser Phe Leu
 65                  70                  75                  80

Ser Asn Glu Glu Phe Thr Gln Leu Met Leu Glu Ala Leu Asp Gly Phe
                 85                  90                  95

Val Ile Val Val Thr Thr Asp Gly Ser Ile Ile Tyr Val Ser Asp Ser
                100                 105                 110

Thr Thr Pro Leu Leu Gly His Leu Pro Ala Asp Val Met Asp Gln Asn
            115                 120                 125

Leu Leu Asn Phe Leu Pro Glu Gln Glu His Ser Glu Val Tyr Lys Ile
        130                 135                 140

Leu Ser Ser His Met Leu Val Thr Asp Ser Pro Ser Pro Glu Phe Leu
145                 150                 155                 160

Lys Ser Asp Asn Asp Leu Glu Phe Tyr Cys His Leu Leu Arg Gly Ser
                165                 170                 175

Leu Asn Pro Lys Glu Phe Pro Thr Tyr Glu Tyr Ile Lys Phe Val Gly
            180                 185                 190

Asn Phe Arg Ser Tyr Asn Asn Val Pro Ser Pro Ser Cys Asn Gly Phe
        195                 200                 205
```

-continued

```
Asp Asn Thr Leu Ser Arg Pro Cys His Val Pro Leu Gly Lys Asp Val
    210                 215                 220

Cys Phe Ile Ala Thr Val Arg Leu Ala Thr Pro Gln Phe Leu Lys Glu
225                 230                 235                 240

Met Cys Val Ala Asp Glu Pro Leu Glu Glu Phe Thr Ser Arg His Ser
                245                 250                 255

Leu Glu Trp Lys Phe Leu Phe Leu Asp His Arg Ala Pro Pro Ile Ile
            260                 265                 270

Gly Tyr Leu Pro Phe Glu Val Leu Gly Thr Ser Gly Tyr Asn Tyr Tyr
        275                 280                 285

His Ile Asp Asp Leu Glu Leu Leu Ala Arg Cys His Gln His Leu Met
    290                 295                 300

Gln Phe Gly Lys Gly Lys Ser Cys Cys Tyr Arg Phe Leu Thr Lys Gly
305                 310                 315                 320

Gln Gln Trp Ile Trp Leu Gln Thr His Tyr Tyr Ile Thr Tyr His Gln
                325                 330                 335

Trp Asn Ser Lys Pro Glu Phe Ile Val Cys Thr His Ser Val Val Ser
            340                 345                 350

Tyr Ala Asp Val Arg Val Glu Arg Arg Gln Glu Leu Ala Leu Glu Asp
        355                 360                 365

Pro Pro Thr Glu Ala Met His Pro Ser Ala Val Lys Glu Lys Asp Ser
    370                 375                 380

Ser Leu Glu Pro Pro Gln Pro Phe Asn Ala Leu Asp Met Gly Ala Ser
385                 390                 395                 400

Gly Leu Pro Ser Ser Pro Ser Pro Ser Ala Ser Ser Arg Ser Ser His
                405                 410                 415

Lys Ser Ser His Thr Ala Met Ser Glu Pro Ile Ser Thr Pro Thr Lys
            420                 425                 430

Leu Met Ala Glu Asn Ser Thr Thr Ala Leu Pro Arg Pro Ala Thr Leu
        435                 440                 445

Pro Gln Glu Leu Pro Val Gln Gly Leu Ser Gln Ala Ala Thr Met Pro
    450                 455                 460

Thr Ala Leu His Ser Ser Ala Ser Cys Asp Leu Thr Lys Gln Leu Leu
465                 470                 475                 480

Leu Gln Ser Leu Pro Gln Thr Gly Leu Gln Ser Pro Pro Ala Pro Val
                485                 490                 495

Thr Gln Phe Ser Ala Gln Phe Ser Met Phe Gln Thr Ile Lys Asp Gln
            500                 505                 510

Leu Glu Gln Arg Thr Arg Ile Leu Gln Ala Asn Ile Arg Trp Gln Gln
        515                 520                 525

Glu Glu Leu His Lys Ile Gln Glu Leu Cys Leu Val Gln Asp Ser
    530                 535                 540

Asn Val Gln Met Phe Leu Gln Gln Pro Ala Val Ser Leu Ser Phe Ser
545                 550                 555                 560

Ser Ile Gln Arg Pro Ala Ala Gln Gln Leu Gln Gln Arg Pro Ala
                565                 570                 575

Ala Pro Ser Gln Pro Gln Leu Val Val Asn Thr Pro Leu Gln Gly Gln
            580                 585                 590

Ile Thr Ser Thr Gln Val Thr Asn Gln His Leu Leu Arg Glu Ser Asn
        595                 600                 605

Val Ile Ser Ala Gln Gly Pro Lys Pro Met Arg Ser Ser Gln Leu Leu
    610                 615                 620

Pro Ala Ser Gly Arg Ser Leu Ser Ser Leu Pro Ser Gln Phe Ser Ser
```

| | | | | | | | | | | |
|---|---|---|---|---|---|---|---|---|---|---|
|625| | | | |630| | | |635| |640|
|Thr|Ala|Ser|Val|Leu|Pro|Pro|Gly|Leu|Ser|Leu|Thr|Thr|Ile|Ala|Pro|
| | | | |645| | | | | |650| | | |655| |

Thr Ala Ser Val Leu Pro Pro Gly Leu Ser Leu Thr Thr Ile Ala Pro
                    645                 650                 655

Thr Pro Gln Asp Asp Ser Gln Cys Gln Pro Ser Pro Asp Phe Gly His
            660                 665                 670

Asp Arg Gln Leu Arg Leu Leu Leu Ser Gln Pro Ile Gln Pro Met Met
        675                 680                 685

Pro Gly Ser Cys Asp Ala Arg Gln Pro Ser Glu Val Ser Arg Thr Gly
    690                 695                 700

Arg Gln Val Lys Tyr Ala Gln Ser Gln Val Met Phe Pro Ser Pro Asp
705                 710                 715                 720

Ser His Pro Thr Asn Ser Ser Ala Ser Thr Pro Val Leu Leu Met Gly
            725                 730                 735

Gln Ala Val Leu His Pro Ser Phe Pro Ala Ser Arg Pro Ser Pro Leu
            740                 745                 750

Gln Pro Ala Gln Ala Gln Gln Pro Pro Tyr Leu Gln Ala Pro
        755                 760                 765

Thr Ser Leu His Ser Glu Gln Pro Asp Ser Leu Leu Ser Thr Phe
    770                 775                 780

Ser Gln Gln Pro Gly Thr Leu Gly Tyr Ala Ala Thr Gln Ser Thr Pro
785                 790                 795                 800

Pro Gln Pro Pro Arg Pro Ser Arg Arg Val Ser Arg Leu Ser Glu Ser
            805                 810                 815

<210> SEQ ID NO 54
<211> LENGTH: 3545
<212> TYPE: DNA
<213> ORGANISM: Homo sapiens

<400> SEQUENCE: 54

```
catgcctcag gatactcctc aatagccatc gctgtagtat atccaaagac aaccatcatt      60
cccccccccc ggcccctgg agcgagagcg cgaaggaaat ctggccgccg ccgccgcgag     120
cgctcccgaa ttttttacttg ttcctgcaaa gctgctggag ctcagaagct gattctatca    180
cattgtaaga tgcctttgga taattctaca gtcctcttaa atgaatcttt gaacttggca    240
agtctcacta gataccttca atcatcattt tgagctcaaa gaattctgag acttatggtt    300
ggtcatatag aagagtacct tgaacctata gtttcctgaa gatcagtttt aaaagatcca    360
aggagtacaa aaggagaagt acaaatgtct actacaagac gaaaacgtag tatgttatgt    420
tgtttaccgt aagctgtagt aaaatgagct cgattgttga cagagatgac agtagtattt    480
ttgatgggtt ggtggaagaa gatgacaagg acaaagcgaa aagagtatct agaaacaaat    540
ctgaaaagaa acgtagagat caatttaatg ttctcattaa agaactggga tccatgcttc    600
ctggtaatgc tagaaagatg gacaaatcta ctgttctgca gaaaagcatt gatttttac     660
gaaaacataa agaatcact gcacagtcag atgctagtga aattcgacag gactggaaac     720
ctacattcct tagtaatgaa gagtttacac aattaatgtt agaggctctt gatggttttt    780
ttttagcaat catgacagat ggaagcataa tatatgtgtc tgagagtgta acttcattac    840
ttgaacattt accatctgat cttgtggatc aaagtatatt taatttttatc ccagaagggg    900
aacattcaga ggtttataaa atactctcta ctcatctgct ggaaagtgat tcattaaccc    960
cagaatattt aaaatcaaaa aatcagttag aattctgttg tcacatgctg cgaggaacaa   1020
tagacccaaa ggagccatct acctatgaat atgtaaaatt tataggaaat ttcaaatctt   1080
```

-continued

```
taaacagtgt atcctcttca gcacacaatg gttttgaagg aactatacaa cgcacacata   1140
ggccatctta tgaagataga gtttgttttg tagctactgt caggttagct acacctcagt   1200
tcatcaagga aatgtgcact gttgaagaac ccaatgaaga gtttacatct agacatagtt   1260
tagaatggaa gtttctgttt ctagatcaca gggcaccacc cataataggg tatttgccat   1320
ttgaagttct gggaacatca ggctatgatt actatcatgt ggatgaccta gaaaatttgg   1380
caaaatgtca tgagcactta atgcaatatg ggaaaggcaa atcatgttat tataggttcc   1440
tgactaaggg gcaacagtgg atttggcttc agactcatta ttatatcact taccatcagt   1500
ggaattcaag gccagagttt attgtttgta ctcacactgt agtaagttat gcagaagtta   1560
gggctgaaag acgacgagaa cttggcattg aagagtctct tcctgagaca gctgctgaca   1620
aaagccaaga ttctgggtca gataatcgta taaacacagt cagtctcaag gaagcattgg   1680
aaaggtttga tcacagccca accccttctg cctcttctcg gagttcaaga aaatcatctc   1740
acacggccgt ctcagaccct tcctcaacac caaccaagat cccgacggat acgagcactc   1800
cacccaggca gcatttacca gctcatgaga agatggtgca aagaaggtca tcatttagta   1860
gtcagtccat aaattcccag tctgttggtt catcattaac acagccagtg atgtctcaag   1920
ctacaaattt accaattcca caaggcatgt cccagtttca gttttcagct caattaggag   1980
ccatgcaaca tctgaaagac caattggaac aacggacacg catgatagaa gcaaatattc   2040
atcggcaaca agaagaacta agaaaaattc aagaacaact tcagatggtc catggtcagg   2100
ggctgcagat gttttttgcaa caatcaaatc ctgggttgaa ttttggttcc gttcaacttt   2160
cttctggaaa ttcatctaac atccagcaac ttgcacctat aaatatgcaa ggccaagttg   2220
ttcctactaa ccagattcaa agtggaatga atactgtaca cattggcaca actcagcaca   2280
tgatacaaca acagacttta cagagtacat caactcagag tcaacaaaat gtactgagtg   2340
ggcacagtca gcaaacatct ctacccagtc agacacagag cactcttaca gccccactgt   2400
ataacactat ggtgatttct cagcctgcag ccggaagcat ggtccagatt ccatctagta   2460
tgccacaaaa cagcacccag agtgctgcag taactacatt cactcaggac aggcagataa   2520
gattttctca aggtcaacaa cttgtgacca aattagtgac tgctcctgta gcttgtgggg   2580
cagtcatggt acctagtact atgcttatgg gccaggtggt gactgcatat cctacttttg   2640
ctacacaaca gcaacagtca cagacattgt cagtaacgca gcagcagcag cagcagagct   2700
cccaggagca gcagctcact tcagttcagc aaccatctca ggctcagctg acccagccac   2760
cgcaacaatt tttacagact tctaggttgc tccatgggaa tccctcaact caactcattc   2820
tctctgctgc atttcctcta caacagagca ccttccctca gtcacatcac cagcaacatc   2880
agtctcagca acagcagcaa ctcagccggc acaggactga cagcttgccc gaccccttcca  2940
aggttcaacc acagtagcac acgtgcttcc tctcttgaca tcaagggagg aaggggatgg   3000
cccattaaga gttactcaga tgacctgagg aaaggaggga agttccagc agtttcatga    3060
gatgcagtat tgagtgttct agttcctgga attagttggc agagaaaatg ctgcctagtg   3120
ctacagatgt acattaaata ccagccagca ggaggtgatc ataggggcac agccagttct   3180
gacagtgttt taggtgcctg gatattttt gatggaaaaa gaatatattg ccaaatatta    3240
agaagctcag ctatgaaatg acctccaggg aatcagaaag gcactaatga tgttagtaac   3300
ttttagtggt tctgtgcctc ttatcaagtg ttacagagga cataccactg ccatgtcagg   3360
ggtttgctta cagtgatgcc atgaagacag tccagtagac ttggtagcga ccccctcccc   3420
caacccctct cccttttcag ataatgatgg aacagtaatt actttcagaa tgttgtgtgg   3480
```

```
gttcaaattc tctatgtaca gatgatgtaa aaatatgtat atgtctagat aaaggagag    3540 aaagc                                                               3545
```

<210> SEQ ID NO 55
<211> LENGTH: 846
<212> TYPE: PRT
<213> ORGANISM: Homo sapiens

<400> SEQUENCE: 55

```
Met Leu Phe Thr Val Ser Cys Ser Lys Met Ser Ser Ile Val Asp Arg
  1               5                  10                  15

Asp Asp Ser Ser Ile Phe Asp Gly Leu Val Glu Glu Asp Asp Lys Asp
                 20                  25                  30

Lys Ala Lys Arg Val Ser Arg Asn Lys Ser Glu Lys Lys Arg Arg Asp
             35                  40                  45

Gln Phe Asn Val Leu Ile Lys Glu Leu Gly Ser Met Leu Pro Gly Asn
         50                  55                  60

Ala Arg Lys Met Asp Lys Ser Thr Val Leu Gln Lys Ser Ile Asp Phe
 65                  70                  75                  80

Leu Arg Lys His Lys Glu Ile Thr Ala Gln Ser Asp Ala Ser Glu Ile
                 85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
        115                 120                 125

Gly Ser Ile Ile Tyr Val Ser Glu Ser Val Thr Ser Leu Leu Glu His
130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Lys Phe Ile Gly Asn Phe Lys Ser Leu Asn Ser
    210                 215                 220

Val Ser Ser Ser Ala His Asn Gly Phe Glu Gly Thr Ile Gln Arg Thr
225                 230                 235                 240

His Arg Pro Ser Tyr Glu Asp Arg Val Cys Phe Val Ala Thr Val Arg
                245                 250                 255

Leu Ala Thr Pro Gln Phe Ile Lys Glu Met Cys Thr Val Glu Glu Pro
            260                 265                 270

Asn Glu Glu Phe Thr Ser Arg His Ser Leu Glu Trp Lys Phe Leu Phe
        275                 280                 285

Leu Asp His Arg Ala Pro Pro Ile Ile Gly Tyr Leu Pro Phe Glu Val
    290                 295                 300

Leu Gly Thr Ser Gly Tyr Asp Tyr Tyr His Val Asp Asp Leu Glu Asn
305                 310                 315                 320

Leu Ala Lys Cys His Glu His Leu Met Gln Tyr Gly Lys Gly Lys Ser
                325                 330                 335

Cys Tyr Tyr Arg Phe Leu Thr Lys Gly Gln Gln Trp Ile Trp Leu Gln
            340                 345                 350
```

-continued

```
Thr His Tyr Tyr Ile Thr Tyr His Gln Trp Asn Ser Arg Pro Glu Phe
        355                 360                 365

Ile Val Cys Thr His Thr Val Ser Tyr Ala Glu Val Arg Ala Glu
        370                 375             380

Arg Arg Arg Glu Leu Gly Ile Glu Glu Ser Leu Pro Glu Thr Ala Ala
385                 390                 395                 400

Asp Lys Ser Gln Asp Ser Gly Ser Asp Asn Arg Ile Asn Thr Val Ser
                405                 410                 415

Leu Lys Glu Ala Leu Glu Arg Phe Asp His Ser Pro Thr Pro Ser Ala
            420                 425                 430

Ser Ser Arg Ser Ser Arg Lys Ser Ser His Thr Ala Val Ser Asp Pro
        435                 440                 445

Ser Ser Thr Pro Thr Lys Ile Pro Thr Asp Thr Ser Thr Pro Pro Arg
    450                 455                 460

Gln His Leu Pro Ala His Glu Lys Met Val Gln Arg Arg Ser Ser Phe
465                 470                 475                 480

Ser Ser Gln Ser Ile Asn Ser Gln Ser Val Gly Ser Ser Leu Thr Gln
                485                 490                 495

Pro Val Met Ser Gln Ala Thr Asn Leu Pro Ile Pro Gln Gly Met Ser
            500                 505                 510

Gln Phe Gln Phe Ser Ala Gln Leu Gly Ala Met Gln His Leu Lys Asp
        515                 520                 525

Gln Leu Glu Gln Arg Thr Arg Met Ile Glu Ala Asn Ile His Arg Gln
    530                 535                 540

Gln Glu Glu Leu Arg Lys Ile Gln Glu Gln Leu Gln Met Val His Gly
545                 550                 555                 560

Gln Gly Leu Gln Met Phe Leu Gln Gln Ser Asn Pro Gly Leu Asn Phe
                565                 570                 575

Gly Ser Val Gln Leu Ser Ser Gly Asn Ser Ser Asn Ile Gln Gln Leu
            580                 585                 590

Ala Pro Ile Asn Met Gln Gly Gln Val Val Pro Thr Asn Gln Ile Gln
        595                 600                 605

Ser Gly Met Asn Thr Gly His Ile Gly Thr Thr Gln His Met Ile Gln
    610                 615                 620

Gln Gln Thr Leu Gln Ser Thr Ser Thr Gln Ser Gln Gln Asn Val Leu
625                 630                 635                 640

Ser Gly His Ser Gln Gln Thr Ser Leu Pro Ser Gln Thr Gln Ser Thr
                645                 650                 655

Leu Thr Ala Pro Leu Tyr Asn Thr Met Val Ile Ser Gln Pro Ala Ala
            660                 665                 670

Gly Ser Met Val Gln Ile Pro Ser Ser Met Pro Gln Asn Ser Thr Gln
        675                 680                 685

Ser Ala Ala Val Thr Thr Phe Thr Gln Asp Arg Gln Ile Arg Phe Ser
    690                 695                 700

Gln Gly Gln Gln Leu Val Thr Lys Leu Val Thr Ala Pro Val Ala Cys
705                 710                 715                 720

Gly Ala Val Met Val Pro Ser Thr Met Leu Met Gly Gln Val Val Thr
                725                 730                 735

Ala Tyr Pro Thr Phe Ala Thr Gln Gln Gln Ser Gln Thr Leu Ser
            740                 745                 750

Val Thr Gln Gln Gln Gln Gln Ser Ser Gln Glu Gln Gln Leu Thr
        755                 760                 765

Ser Val Gln Gln Pro Ser Gln Ala Gln Leu Thr Gln Pro Pro Gln Gln
```

-continued

```
                    770                 775                 780
Phe Leu Gln Thr Ser Arg Leu Leu His Gly Asn Pro Ser Thr Gln Leu
785                 790                 795                 800

Ile Leu Ser Ala Ala Phe Pro Leu Gln Gln Ser Thr Phe Pro Gln Ser
                805                 810                 815

His His Gln Gln His Gln Ser Gln Gln Gln Gln Leu Ser Arg His
                820                 825                 830

Arg Thr Asp Ser Leu Pro Asp Pro Ser Lys Val Gln Pro Gln
            835                 840                 845
```